(12) United States Patent
Koide et al.

(10) Patent No.: US 12,049,483 B2
(45) Date of Patent: Jul. 30, 2024

(54) SELECTIVE AND NONCOVALENT INHIBITORS OF ONCOGENIC RAS MUTANTS

(71) Applicant: New York University, New York, NY (US)

(72) Inventors: Shohei Koide, New York, NY (US); Kai Wen Teng, Flushing, NY (US); Akiko Koide, New York, NY (US); Takamitsu Hattori, West New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 17/543,464

(22) Filed: Dec. 6, 2021

(65) Prior Publication Data

US 2022/0177531 A1    Jun. 9, 2022

Related U.S. Application Data

(60) Provisional application No. 63/121,903, filed on Dec. 5, 2020.

(51) Int. Cl.
*C07K 14/47* (2006.01)
*A61K 38/00* (2006.01)
*A61P 35/00* (2006.01)

(52) U.S. Cl.
CPC .......... *C07K 14/4702* (2013.01); *A61P 35/00* (2018.01); *A61K 38/00* (2013.01); *C07B 2200/13* (2013.01)

(58) Field of Classification Search
None
See application file for complete search history.

(56) References Cited

U.S. PATENT DOCUMENTS 9,512,199 B2 * 12/2016 Loew ................ C07K 14/78

FOREIGN PATENT DOCUMENTS

WO    WO 2014/206336    * 12/2014

OTHER PUBLICATIONS

GeneBank (Ras GTPase activating protein ira2 [*Peltula* sp. TS41687], Nov. 7, 2022) (Year: 2022).*
By Sot et al. (PNAS, Jan. 2, 2013;110(1):111-6) (Year: 2013).*

* cited by examiner

*Primary Examiner* — Sergio Coffa
(74) *Attorney, Agent, or Firm* — Hodgson Russ LLP

(57) ABSTRACT

Provided are proteins or peptides, which may be referred to as monobodies. Fusion proteins and proteolysis targeting chimeras (PROTACs) comprising the proteins or peptides are also provided. Also provided are compositions of the proteins or peptides of the present disclosure, as well as compositions of fusion proteins and compositions of PROTACs. Methods of treating an individual in need of treatment are also provided. The methods may be to treat an individual suffering from or suspected of having KRAS(G12V), KRAS(G12S), KRAS(G12A) and/or KRAS(G12C)-associated cancers. A method may be for inhibiting ERK activation and/or proliferation of KRAS(G12V), KRAS(G12S), KRAS(G12A) and/or KRAS(G12C)-associated cancers.

23 Claims, 24 Drawing Sheets
Specification includes a Sequence Listing.

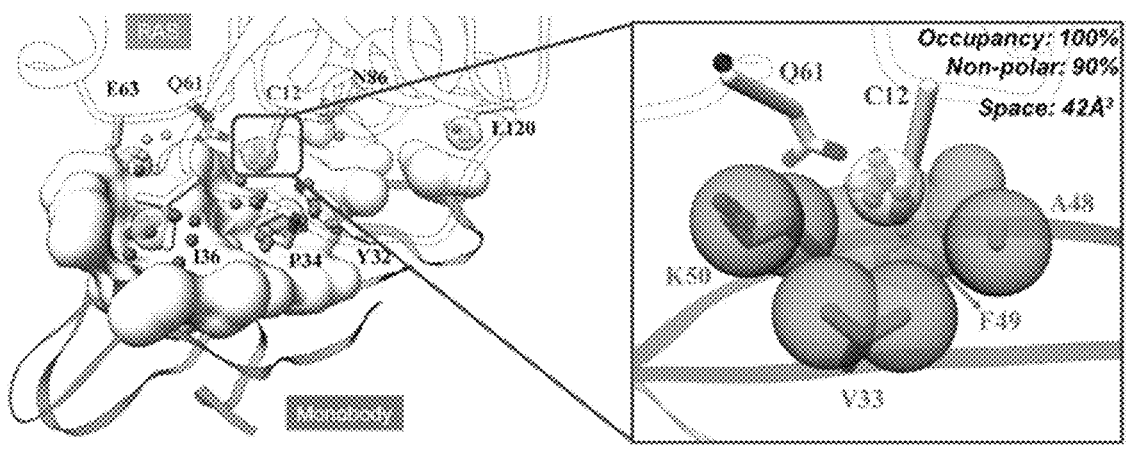

| RAS mutant | MD length | Avg. Distance[a] | Avg. RMSD[b] | Loop_RMSD[c] | Loop_dist[d] | Complex stability | Experimental |
|---|---|---|---|---|---|---|---|
| G12C | 250ns | 5.1±0.4 | 3.2±0.6 | 2.0±0.6 | 3.1±0.5 | Stable | Binding |
| G12V | 250ns | 5.3±0.4 | 2.3±0.2 | 1.7±0.5 | 3.0±0.3 | Stable | Binding |
| G12wt | 250ns | 8.4±1.3 | 6.8±2.2 | 4.4±1.6 | 5.4±1.7 | Unstable | No binding |
| G12D | 250ns | 7.2±1.5 | 7.7±3.4 | 5.5±2.8 | 5.9±2.6 | Unstable | No binding |
| G13D | 250ns | 9.0±1.0 | 7.9±2.4 | 5.3±1.7 | 6.5±1.9 | Unstable | No binding |
| Q61L | 250ns | 9.5±1.1 | 11.7±2.1 | 7.1±1.8 | 8.2±1.8 | Unstable | No binding |

[a] Average distance between #12 residue in RAS and V33/A48/K50 in monobody
[b] Average RMSD of monobody during MD simulation (complex aligned based on RAS)
[c] Average RMSD of Loop(G44/A45/F46) of monobody during MD simulation (complex aligned based on RAS)
[d] Average distance between K117 (Ras) and G44 (Monobody)

Figure 9

SEQUENCE LISTING

```
<160> NUMBER OF SEQ ID NOS: 28

<210> SEQ ID NO 1
<211> LENGTH: 95
<212> TYPE: PRT
<213> ORGANISM: Artificial Sequence
<220> FEATURE:
<223> OTHER INFORMATION: 12VC1

<400> SEQUENCE: 1

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Phe Phe Tyr
            20                  25                  30

Val Ile Thr Tyr Gly Glu Thr Gly His Gly Val Gly Ala Phe Gln Ala
        35                  40                  45

Phe Lys Val Pro Gly Ser Lys Ser Thr Ala Thr Ile Ser Gly Leu Lys
```

```
                    50                  55                  60
Pro Gly Val Asp Tyr Thr Ile Thr Val Tyr Ala Arg Gly Tyr Ser Lys
 65                  70                  75                  80

Gln Gly Pro Tyr Lys Pro Ser Pro Ile Ser Ile Asn Tyr Arg Thr
                    85                  90                  95

<210> SEQ ID NO 2
<211> LENGTH: 95
<212> TYPE: PRT
<213> ORGANISM: Artificial Sequence
<220> FEATURE:
<223> OTHER INFORMATION: Synthetic peptide

<400> SEQUENCE: 2

Val Ser Ser Val Pro Thr Glu Leu Glu Val Val Ala Ala Thr Pro Thr
 1               5                  10                  15

Ser Leu Leu Ile Ser Trp Asp Ala Pro Ala Val Thr Val Phe Phe Tyr
                    20                  25                  30

Val Ile Thr Tyr Gly Glu Thr Gly His Gly Val Gly Ala Phe Gln Ala
                    35                  40                  45

Phe Lys Val Pro Gly Ser Arg Ser Thr Ala Thr Ile Ser Gly Leu Glu
                    50                  55                  60

Pro Gly Val Asp Tyr Thr Ile Thr Val Tyr Ala Arg Gly Tyr Ser Lys
 65                  70                  75                  80

Gln Gly Pro Tyr Lys Pro Ser Pro Ile Ser Ile Asn Tyr Arg Thr
                    85                  90                  95

<210> SEQ ID NO 3
<211> LENGTH: 95
<212> TYPE: PRT
<213> ORGANISM: Artificial Sequence
<220> FEATURE:
<223> OTHER INFORMATION: Synthetic peptide

<400> SEQUENCE: 3

Val Ser Ser Val Pro Thr Glu Leu Glu Val Val Ala Ala Thr Pro Thr
 1               5                  10                  15

Ser Leu Leu Ile Ser Trp Asp Ala Pro Ala Val Thr Val Phe Phe Tyr
                    20                  25                  30

Val Ile Thr Tyr Gly Glu Thr Gly His Gly Val Gly Ala Phe Gln Ala
                    35                  40                  45

Phe Ala Val Pro Gly Ser Arg Ser Thr Ala Thr Ile Ser Gly Leu Glu
                    50                  55                  60

Pro Gly Val Asp Tyr Thr Ile Thr Val Tyr Ala Arg Gly Tyr Ser Lys
 65                  70                  75                  80

Gln Gly Pro Tyr Lys Pro Ser Pro Ile Ser Ile Asn Tyr Arg Thr
                    85                  90                  95

<210> SEQ ID NO 4
<211> LENGTH: 95
<212> TYPE: PRT
<213> ORGANISM: Artificial Sequence
<220> FEATURE:
<223> OTHER INFORMATION: Synthetic peptide

<400> SEQUENCE: 4

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Phe Phe Tyr
                    20                  25                  30
```

Ile Ile Ala Tyr Gly Glu Thr Gly His Gly Val Gly Ala Phe Gln Ala
                35                  40                  45

Phe Arg Val Pro Gly Ser Lys Ser Thr Ala Thr Ile Ser Gly Leu Lys
        50                  55                  60

Pro Gly Val Asp Tyr Thr Ile Thr Val Tyr Ala Arg Gly Tyr Ser Lys
65                  70                  75                  80

Gln Gly Pro Tyr Lys Pro Ser Pro Ile Ser Ile Asn Tyr Arg Thr
                85                  90                  95

<210> SEQ ID NO 5
<211> LENGTH: 95
<212> TYPE: PRT
<213> ORGANISM: Artificial Sequence
<220> FEATURE:
<223> OTHER INFORMATION: Synthetic peptide

<400> SEQUENCE: 5

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Ala Phe Tyr
                20                  25                  30

Val Ile Thr Tyr Gly Glu Thr Gly His Gly Val Gly Ala Phe Gln Ala
                35                  40                  45

Phe Lys Val Pro Gly Ser Lys Ser Thr Ala Thr Ile Ser Gly Leu Lys
        50                  55                  60

Pro Gly Val Asp Tyr Thr Ile Thr Val Tyr Ala Arg Gly Tyr Ser Lys
65                  70                  75                  80

Gln Gly Pro Tyr Lys Pro Ser Pro Ile Ser Ile Asn Tyr Arg Thr
                85                  90                  95

<210> SEQ ID NO 6
<211> LENGTH: 95
<212> TYPE: PRT
<213> ORGANISM: Artificial Sequence
<220> FEATURE:
<223> OTHER INFORMATION: Synthetic peptide

<400> SEQUENCE: 6

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Phe Ala Tyr
                20                  25                  30

Val Ile Thr Tyr Gly Glu Thr Gly His Gly Val Gly Ala Phe Gln Ala
                35                  40                  45

Phe Lys Val Pro Gly Ser Lys Ser Thr Ala Thr Ile Ser Gly Leu Lys
        50                  55                  60

Pro Gly Val Asp Tyr Thr Ile Thr Val Tyr Ala Arg Gly Tyr Ser Lys
65                  70                  75                  80

Gln Gly Pro Tyr Lys Pro Ser Pro Ile Ser Ile Asn Tyr Arg Thr
                85                  90                  95

<210> SEQ ID NO 7
<211> LENGTH: 95
<212> TYPE: PRT
<213> ORGANISM: Artificial Sequence
<220> FEATURE:
<223> OTHER INFORMATION: Synthetic peptide

<400> SEQUENCE: 7

-continued

Val Ser Ser Val Pro Thr Lys Leu Glu Val Ala Ala Thr Pro Thr
1               5                   10                  15

Ser Leu Leu Ile Ser Trp Asp Ala Pro Ala Val Thr Val Phe Phe Tyr
            20                  25                  30

Ala Ile Thr Tyr Gly Glu Thr Gly His Gly Val Gly Ala Phe Gln Ala
        35                  40                  45

Phe Lys Val Pro Gly Ser Lys Ser Thr Ala Thr Ile Ser Gly Leu Lys
    50                  55                  60

Pro Gly Val Asp Tyr Thr Ile Thr Val Tyr Ala Arg Gly Tyr Ser Lys
65                  70                  75                  80

Gln Gly Pro Tyr Lys Pro Ser Pro Ile Ser Ile Asn Tyr Arg Thr
            85                  90                  95

<210> SEQ ID NO 8
<211> LENGTH: 95
<212> TYPE: PRT
<213> ORGANISM: Artificial Sequence
<220> FEATURE:
<223> OTHER INFORMATION: Synthetic peptide

<400> SEQUENCE: 8

Val Ser Ser Val Pro Thr Lys Leu Glu Val Ala Ala Thr Pro Thr
1               5                   10                  15

Ser Leu Leu Ile Ser Trp Asp Ala Pro Ala Val Thr Val Phe Phe Tyr
            20                  25                  30

Val Ile Ala Tyr Gly Glu Thr Gly His Gly Val Gly Ala Phe Gln Ala
        35                  40                  45

Phe Lys Val Pro Gly Ser Lys Ser Thr Ala Thr Ile Ser Gly Leu Lys
    50                  55                  60

Pro Gly Val Asp Tyr Thr Ile Thr Val Tyr Ala Arg Gly Tyr Ser Lys
65                  70                  75                  80

Gln Gly Pro Tyr Lys Pro Ser Pro Ile Ser Ile Asn Tyr Arg Thr
            85                  90                  95

<210> SEQ ID NO 9
<211> LENGTH: 95
<212> TYPE: PRT
<213> ORGANISM: Artificial Sequence
<220> FEATURE:
<223> OTHER INFORMATION: Synthetic peptide

<400> SEQUENCE: 9

Val Ser Ser Val Pro Thr Lys Leu Glu Val Ala Ala Thr Pro Thr
1               5                   10                  15

Ser Leu Leu Ile Ser Trp Asp Ala Pro Ala Val Thr Val Phe Phe Tyr
            20                  25                  30

Val Ile Thr Tyr Gly Glu Thr Gly His Gly Ala Gly Ala Phe Gln Ala
        35                  40                  45

Phe Lys Val Pro Gly Ser Lys Ser Thr Ala Thr Ile Ser Gly Leu Lys
    50                  55                  60

Pro Gly Val Asp Tyr Thr Ile Thr Val Tyr Ala Arg Gly Tyr Ser Lys
65                  70                  75                  80

Gln Gly Pro Tyr Lys Pro Ser Pro Ile Ser Ile Asn Tyr Arg Thr
            85                  90                  95

<210> SEQ ID NO 10
<211> LENGTH: 95
<212> TYPE: PRT
<213> ORGANISM: Artificial Sequence -continued
<220> FEATURE:
<223> OTHER INFORMATION: Synthetic peptide

<400> SEQUENCE: 10

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Phe Phe Tyr
            20                  25                  30

Val Ile Thr Tyr Gly Glu Thr Gly His Gly Val Gly Ala Ala Gln Ala
        35                  40                  45

Phe Lys Val Pro Gly Ser Lys Ser Thr Ala Thr Ile Ser Gly Leu Lys
    50                  55                  60

Pro Gly Val Asp Tyr Thr Ile Thr Val Tyr Ala Arg Gly Tyr Ser Lys
65                  70                  75                  80

Gln Gly Pro Tyr Lys Pro Ser Pro Ile Ser Ile Asn Tyr Arg Thr
                85                  90                  95

<210> SEQ ID NO 11
<211> LENGTH: 95
<212> TYPE: PRT
<213> ORGANISM: Artificial Sequence
<220> FEATURE:
<223> OTHER INFORMATION: Synthetic peptide

<400> SEQUENCE: 11

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Phe Phe Tyr
            20                  25                  30

Val Ile Thr Tyr Gly Glu Thr Gly His Gly Val Gly Ala Phe Ala Ala
        35                  40                  45

Phe Lys Val Pro Gly Ser Lys Ser Thr Ala Thr Ile Ser Gly Leu Lys
    50                  55                  60

Pro Gly Val Asp Tyr Thr Ile Thr Val Tyr Ala Arg Gly Tyr Ser Lys
65                  70                  75                  80

Gln Gly Pro Tyr Lys Pro Ser Pro Ile Ser Ile Asn Tyr Arg Thr
                85                  90                  95

<210> SEQ ID NO 12
<211> LENGTH: 95
<212> TYPE: PRT
<213> ORGANISM: Artificial Sequence
<220> FEATURE:
<223> OTHER INFORMATION: Synthetic peptide

<400> SEQUENCE: 12

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Phe Phe Tyr
            20                  25                  30

Val Ile Thr Tyr Gly Glu Thr Gly His Gly Val Gly Ala Phe Gln Ala
        35                  40                  45

Ala Lys Val Pro Gly Ser Lys Ser Thr Ala Thr Ile Ser Gly Leu Lys
    50                  55                  60

Pro Gly Val Asp Tyr Thr Ile Thr Val Tyr Ala Arg Gly Tyr Ser Lys
65                  70                  75                  80

Gln Gly Pro Tyr Lys Pro Ser Pro Ile Ser Ile Asn Tyr Arg Thr
                85                  90                  95

```
<210> SEQ ID NO 13
<211> LENGTH: 95
<212> TYPE: PRT
<213> ORGANISM: Artificial Sequence
<220> FEATURE:
<223> OTHER INFORMATION: Synthetic peptide

<400> SEQUENCE: 13

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Phe Phe Tyr
                20                  25                  30

Val Ile Thr Tyr Gly Glu Thr Gly His Gly Val Gly Ala Phe Gln Ala
            35                  40                  45

Phe Ala Val Pro Gly Ser Lys Ser Thr Ala Thr Ile Ser Gly Leu Lys
        50                  55                  60

Pro Gly Val Asp Tyr Thr Ile Thr Val Tyr Ala Arg Gly Tyr Ser Lys
65                  70                  75                  80

Gln Gly Pro Tyr Lys Pro Ser Pro Ile Ser Ile Asn Tyr Arg Thr
                85                  90                  95

<210> SEQ ID NO 14
<211> LENGTH: 95
<212> TYPE: PRT
<213> ORGANISM: Artificial Sequence
<220> FEATURE:
<223> OTHER INFORMATION: Synthetic peptide

<400> SEQUENCE: 14

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Phe Phe Tyr
                20                  25                  30

Val Ile Thr Tyr Gly Glu Thr Gly His Gly Val Gly Ala Phe Gln Ala
            35                  40                  45

Phe Lys Val Ala Gly Ser Lys Ser Thr Ala Thr Ile Ser Gly Leu Lys
        50                  55                  60

Pro Gly Val Asp Tyr Thr Ile Thr Val Tyr Ala Arg Gly Tyr Ser Lys
65                  70                  75                  80

Gln Gly Pro Tyr Lys Pro Ser Pro Ile Ser Ile Asn Tyr Arg Thr
                85                  90                  95

<210> SEQ ID NO 15
<211> LENGTH: 95
<212> TYPE: PRT
<213> ORGANISM: Artificial Sequence
<220> FEATURE:
<223> OTHER INFORMATION: Synthetic peptide

<400> SEQUENCE: 15

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Phe Phe Tyr
                20                  25                  30

Val Ile Thr Tyr Gly Glu Thr Gly His Gly Val Gly Ala Phe Gln Ala
            35                  40                  45

Phe Lys Val Pro Ala Ser Lys Ser Thr Ala Thr Ile Ser Gly Leu Lys
        50                  55                  60

Pro Gly Val Asp Tyr Thr Ile Thr Val Tyr Ala Arg Gly Tyr Ser Lys
```

Gln Gly Pro Tyr Lys Pro Ser Pro Ile Ser Ile Asn Tyr Arg Thr
            85                  90                  95

<210> SEQ ID NO 16
<211> LENGTH: 95
<212> TYPE: PRT
<213> ORGANISM: Artificial Sequence
<220> FEATURE:
<223> OTHER INFORMATION: Synthetic peptide

<400> SEQUENCE: 16

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Phe Phe Tyr
            20                  25                  30

Val Ile Thr Tyr Gly Glu Thr Gly His Gly Val Gly Ala Phe Gln Ala
        35                  40                  45

Phe Lys Val Pro Gly Ser Lys Ser Thr Ala Thr Ile Ser Gly Leu Lys
    50                  55                  60

Pro Gly Val Asp Tyr Thr Ile Thr Val Tyr Ala Arg Ala Tyr Ser Lys
65                  70                  75                  80

Gln Gly Pro Tyr Lys Pro Ser Pro Ile Ser Ile Asn Tyr Arg Thr
            85                  90                  95

<210> SEQ ID NO 17
<211> LENGTH: 95
<212> TYPE: PRT
<213> ORGANISM: Artificial Sequence
<220> FEATURE:
<223> OTHER INFORMATION: Synthetic peptide

<400> SEQUENCE: 17

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Phe Phe Tyr
            20                  25                  30

Val Ile Thr Tyr Gly Glu Thr Gly His Gly Val Gly Ala Phe Gln Ala
        35                  40                  45

Phe Lys Val Pro Gly Ser Lys Ser Thr Ala Thr Ile Ser Gly Leu Lys
    50                  55                  60

Pro Gly Val Asp Tyr Thr Ile Thr Val Tyr Ala Arg Gly Ala Ser Lys
65                  70                  75                  80

Gln Gly Pro Tyr Lys Pro Ser Pro Ile Ser Ile Asn Tyr Arg Thr
            85                  90                  95

<210> SEQ ID NO 18
<211> LENGTH: 94
<212> TYPE: PRT
<213> ORGANISM: Artificial Sequence
<220> FEATURE:
<223> OTHER INFORMATION: Synthetic peptide

<400> SEQUENCE: 18

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Phe Phe Tyr
            20                  25                  30

Val Ile Thr Tyr Gly Glu Thr Gly His Gly Val Gly Ala Phe Gln Ala
        35                  40                  45

Phe Lys Val Pro Gly Ser Lys Ser Thr Ala Thr Ile Ser Gly Leu Lys
        50                  55                  60

Pro Gly Val Asp Tyr Thr Ile Thr Val Tyr Ala Arg Gly Tyr Ser Lys
 65                  70                  75                  80

Gln Gly Ala Tyr Lys Pro Ser Pro Ile Ser Ile Asn Tyr Arg
                85                  90

<210> SEQ ID NO 19
<211> LENGTH: 95
<212> TYPE: PRT
<213> ORGANISM: Artificial Sequence
<220> FEATURE:
<223> OTHER INFORMATION: Synthetic peptide

<400> SEQUENCE: 19

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Phe Phe Tyr
                20                  25                  30

Val Ile Thr Tyr Gly Glu Thr Gly His Gly Val Gly Ala Phe Gln Ala
            35                  40                  45

Phe Lys Val Pro Gly Ser Lys Ser Thr Ala Thr Ile Ser Gly Leu Lys
        50                  55                  60

Pro Gly Val Asp Tyr Thr Ile Thr Val Tyr Ala Arg Gly Tyr Ser Lys
 65                  70                  75                  80

Gln Gly Pro Ala Lys Pro Ser Pro Ile Ser Ile Asn Tyr Arg Thr
                85                  90                  95

<210> SEQ ID NO 20
<211> LENGTH: 95
<212> TYPE: PRT
<213> ORGANISM: Artificial Sequence
<220> FEATURE:
<223> OTHER INFORMATION: Synthetic peptide

<400> SEQUENCE: 20

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Phe Phe Tyr
                20                  25                  30

Val Ile Thr Tyr Gly Glu Thr Gly His Gly Val Gly Ala Phe Gln Ala
            35                  40                  45

Phe Lys Val Pro Gly Ser Lys Ser Thr Ala Thr Ile Ser Gly Leu Lys
        50                  55                  60

Pro Gly Val Asp Tyr Thr Ile Thr Val Tyr Ala Arg Gly Tyr Ser Lys
 65                  70                  75                  80

Gln Gly Pro Tyr Ala Pro Ser Pro Ile Ser Ile Asn Tyr Arg Thr
                85                  90                  95

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide

<400> SEQUENCE: 21

Leu Val Val Val Gly Ala Val Gly Val Gly Lys
 1               5                  10

```
<210> SEQ ID NO 22
<211> LENGTH: 11
<212> TYPE: PRT
<213> ORGANISM: Artificial Sequence
<220> FEATURE:
<223> OTHER INFORMATION: Synthetic peptide

<400> SEQUENCE: 22

Leu Val Val Val Gly Ala Gly Gly Val Gly Lys
1               5                   10

<210> SEQ ID NO 23
<211> LENGTH: 166
<212> TYPE: PRT
<213> ORGANISM: Homo sapiens

<400> SEQUENCE: 23

Met Thr Glu Tyr Lys Leu Val Val Val Gly Ala Cys Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His
                165

<210> SEQ ID NO 24
<211> LENGTH: 5
<212> TYPE: PRT
<213> ORGANISM: Artificial Sequence
<220> FEATURE:
<223> OTHER INFORMATION: Linker

<400> SEQUENCE: 24

Ser Ser Ser Ser Gly
1               5

<210> SEQ ID NO 25
<211> LENGTH: 9
<212> TYPE: PRT
<213> ORGANISM: Artificial Sequence
<220> FEATURE:
<223> OTHER INFORMATION: Linker

<400> SEQUENCE: 25

Tyr Pro Tyr Asp Val Pro Asp Tyr Ala
1               5
```

```
<210> SEQ ID NO 26
<211> LENGTH: 95
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(3)
<223> OTHER INFORMATION: Xaa is a hydrophilic amino acid residue
<220> FEATURE:
<221> NAME/KEY: MISC_FEATURE
<222> LOCATION: (7)..(7)
<223> OTHER INFORMATION: Xaa is a hydrophilic amino acid residue
<220> FEATURE:
<221> NAME/KEY: MISC_FEATURE
<222> LOCATION: (15)..(16)
<223> OTHER INFORMATION: Xaa is a hydrophilic amino acid residue
<220> FEATURE:
<221> NAME/KEY: MISC_FEATURE
<222> LOCATION: (30)..(30)
<223> OTHER INFORMATION: Xaa is a hydrophilic amino acid residue
<220> FEATURE:
<221> NAME/KEY: MISC_FEATURE
<222> LOCATION: (35)..(35)
<223> OTHER INFORMATION: Xaa is a hydrophilic amino acid residue
<220> FEATURE:
<221> NAME/KEY: MISC_FEATURE
<222> LOCATION: (47)..(47)
<223> OTHER INFORMATION: Xaa is a hydrophilic amino acid residue
<220> FEATURE:
<221> NAME/KEY: MISC_FEATURE
<222> LOCATION: (50)..(50)
<223> OTHER INFORMATION: Xaa is a hydrophilic amino acid residue
<220> FEATURE:
<221> NAME/KEY: MISC_FEATURE
<222> LOCATION: (52)..(55)
<223> OTHER INFORMATION: Xaa is a hydrophilic amino acid residue
<220> FEATURE:
<221> NAME/KEY: MISC_FEATURE
<222> LOCATION: (64)..(64)
<223> OTHER INFORMATION: Xaa is a hydrophilic amino acid residue
<220> FEATURE:
<221> NAME/KEY: MISC_FEATURE
<222> LOCATION: (77)..(78)
<223> OTHER INFORMATION: Xaa is a hydrophilic amino acid residue
<220> FEATURE:
<221> NAME/KEY: MISC_FEATURE
<222> LOCATION: (83)..(83)
<223> OTHER INFORMATION: Xaa is a hydrophilic amino acid residue
<220> FEATURE:
<221> NAME/KEY: MISC_FEATURE
<222> LOCATION: (85)..(85)
<223> OTHER INFORMATION: Xaa is a hydrophilic amino acid residue

<400> SEQUENCE: 26

Xaa Xaa Xaa Val Pro Thr Xaa Leu Glu Val Val Ala Ala Thr Xaa Xaa
1               5                   10                  15

Ser Leu Leu Ile Ser Trp Asp Ala Pro Ala Val Thr Val Xaa Phe Tyr
            20                  25                  30

Val Ile Xaa Tyr Gly Glu Thr Gly His Gly Val Gly Ala Phe Xaa Ala
        35                  40                  45

Phe Xaa Val Xaa Xaa Xaa Xaa Ser Thr Ala Thr Ile Ser Gly Leu Xaa
    50                  55                  60

Pro Gly Val Asp Tyr Thr Ile Thr Val Tyr Ala Arg Xaa Xaa Ser Lys
65                  70                  75                  80

Gln Gly Xaa Tyr Xaa Pro Ser Pro Ile Ser Ile Asn Tyr Arg Thr
                85                  90                  95

<210> SEQ ID NO 27
```

```
<211> LENGTH: 95
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (30)..(30)
<223> OTHER INFORMATION: Xaa is a hydrophilic amino acid residue
<220> FEATURE:
<221> NAME/KEY: MISC_FEATURE
<222> LOCATION: (35)..(35)
<223> OTHER INFORMATION: Xaa is a hydrophilic amino acid residue
<220> FEATURE:
<221> NAME/KEY: MISC_FEATURE
<222> LOCATION: (47)..(47)
<223> OTHER INFORMATION: Xaa is a hydrophilic amino acid residue
<220> FEATURE:
<221> NAME/KEY: MISC_FEATURE
<222> LOCATION: (50)..(50)
<223> OTHER INFORMATION: Xaa is a hydrophilic amino acid residue
<220> FEATURE:
<221> NAME/KEY: MISC_FEATURE
<222> LOCATION: (52)..(53)
<223> OTHER INFORMATION: Xaa is a hydrophilic amino acid residue
<220> FEATURE:
<221> NAME/KEY: MISC_FEATURE
<222> LOCATION: (77)..(78)
<223> OTHER INFORMATION: Xaa is a hydrophilic amino acid residue
<220> FEATURE:
<221> NAME/KEY: MISC_FEATURE
<222> LOCATION: (83)..(83)
<223> OTHER INFORMATION: Xaa is a hydrophilic amino acid residue
<220> FEATURE:
<221> NAME/KEY: MISC_FEATURE
<222> LOCATION: (85)..(85)
<223> OTHER INFORMATION: Xaa is a hydrophilic amino acid residue

<400> SEQUENCE: 27

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Xaa Phe Tyr
            20                  25                  30

Val Ile Xaa Tyr Gly Glu Thr Gly His Gly Val Gly Ala Phe Xaa Ala
        35                  40                  45

Phe Xaa Val Xaa Xaa Ser Lys Ser Thr Ala Thr Ile Ser Gly Leu Lys
    50                  55                  60

Pro Gly Val Asp Tyr Thr Ile Thr Val Tyr Ala Arg Xaa Xaa Ser Lys
65                  70                  75                  80

Gln Gly Xaa Tyr Xaa Pro Ser Pro Ile Ser Ile Asn Tyr Arg Thr
                85                  90                  95

<210> SEQ ID NO 28
<211> LENGTH: 95
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(3)
<223> OTHER INFORMATION: Xaa is a hydrophilic amino acid
<220> FEATURE:
<221> NAME/KEY: MISC_FEATURE
<222> LOCATION: (7)..(7)
<223> OTHER INFORMATION: Xaa is a hydrophilic amino acid
<220> FEATURE:
<221> NAME/KEY: MISC_FEATURE
<222> LOCATION: (15)..(16)
<223> OTHER INFORMATION: Xaa is a hydrophilic amino acid
<220> FEATURE:
<221> NAME/KEY: MISC_FEATURE
```

```
<222> LOCATION: (54)..(55)
<223> OTHER INFORMATION: Xaa is a hydrophilic amino acid
<220> FEATURE:
<221> NAME/KEY: MISC_FEATURE
<222> LOCATION: (64)..(64)
<223> OTHER INFORMATION: Xaa is a hydrophilic amino acid

<400> SEQUENCE: 28

Xaa Xaa Xaa Val Pro Thr Xaa Leu Glu Val Val Ala Ala Thr Xaa Xaa
1               5                   10                  15

Ser Leu Leu Ile Ser Trp Asp Ala Pro Ala Val Thr Val Phe Phe Tyr
            20                  25                  30

Val Ile Thr Tyr Gly Glu Thr Gly His Gly Val Gly Ala Phe Gln Ala
        35                  40                  45

Phe Lys Val Pro Gly Xaa Xaa Ser Thr Ala Thr Ile Ser Gly Leu Xaa
    50                  55                  60

Pro Gly Val Asp Tyr Thr Ile Thr Val Tyr Ala Arg Gly Tyr Ser Lys
65              70                  75                  80

Gln Gly Pro Tyr Lys Pro Ser Pro Ile Ser Ile Asn Tyr Arg Thr
            85                  90                  95
```

SELECTIVE AND NONCOVALENT INHIBITORS OF ONCOGENIC RAS MUTANTS

CROSS REFERENCE TO RELATED APPLICATIONS

This application claims priority to U.S. Provisional Application No. 63/121,903, filed on Dec. 5, 2020, the disclosure of which is incorporated herein by reference.

STATEMENT REGARDING FEDERALLY SPONSORED RESEARCH

This invention was made with government support under grant nos. CA212608, CA194864, and CA201717 awarded by the National Institutes of Health. The government has certain rights in the invention.

BACKGROUND OF THE DISCLOSURE

Activating mutants of RAS are found in more than 25% of all human cancers, and to date direct targeting of RAS in the clinic has been limited to KRAS(G12C) through allele-specific covalent inhibitors. The majority of the oncogenic RAS mutants do not possess a unique reactive group suitable for targeting with covalent inhibitors, and hence how to develop selective, non-covalent warheads that are broadly applicable to RAS mutants, and how to turn such warheads into effective therapeutic strategies remain major unanswered questions in RAS drug discovery.

Recent clinical trials of G12C allele-specific inhibitors revealed high dose tolerance and effective tumor reduction in certain patients, supporting selective targeting of RAS mutants as a viable therapeutic strategy against RAS-driven cancer. By contrast, despite extensive effort, potent and selective inhibitors against other RAS mutants are still lacking, suggesting that developing such inhibitors requires a different approach. Covalent inhibitors bind to an area under the switch II region, called S-II pocket, that is present in the GDP-bound state and form covalent linkage to Cys12. These G12C-selective inhibitors are effective, because KRAS(G12C) cycles intrinsically between the active, GTP-bound form and the inactive GDP-bound form and the compounds lock KRAS(G12C) in the inactive state. Most mutants, such as KRAS(G12V), have slow intrinsic nucleotide exchange rates and thus remain in the active state for an extended period, which predicts challenges in achieving efficacy by trapping them in the GDP-bound form. Thus, targeting the GTP-bound state should be the preferred approach for many RAS mutants. However, there have been no reports of small molecules that selectively bind to a RAS mutant in the GTP-bound state. For proof-of-concept purposes, many binding proteins targeting to the GTP-bound state of RAS mutants have been developed, but they are either not selective for mutants (over wild-type (WT) KRAS) or not effective in inhibiting RAS-mediated signaling in cells. Their lack of efficacy might reflect their inability to effectively compete against multiple RAS-binding effectors. Alternatively, these molecules may have insufficient selectivity to effectively engage in RAS mutants in cells where potentially excess concentrations of wild-type RAS isoforms serve as a sink for low-specificity inhibitors.

There is currently a need for an inhibitor with high selectivity and affinity.

SUMMARY OF THE DISCLOSURE

The present disclosure provides proteins or peptides, which may be referred to as monobodies. Fusion proteins and proteolysis targeting chimeras (PROTACs) comprising the proteins or peptides are also provided. Also provided are compositions comprising proteins or peptides of the present disclosure, as well as fusion proteins and PROTACs.

Methods of treating an individual in need of treatment are also provided. The methods may be to treat an individual suffering from or suspected of having KRAS(G12V), KRAS (G12S), KRAS(G12A) and/or KRAS(G12C)-associated cancers. A method may be for inhibiting ERK activation and/or proliferation of KRAS(G12V), KRAS(G12S), KRAS (G12A) and/or KRAS(G12C)-associated cancers. A method may be for reducing levels of endogenous RAS mutants. A method may also be for crystallizing a protein. A method may be for determining one or more potential drug(s) for treatment of KRAS(G12V), KRAS(G12S), KRAS(G12A) and/or KRAS(G12C)-associated cancers. A method may be for pulling down active RAS mutants.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
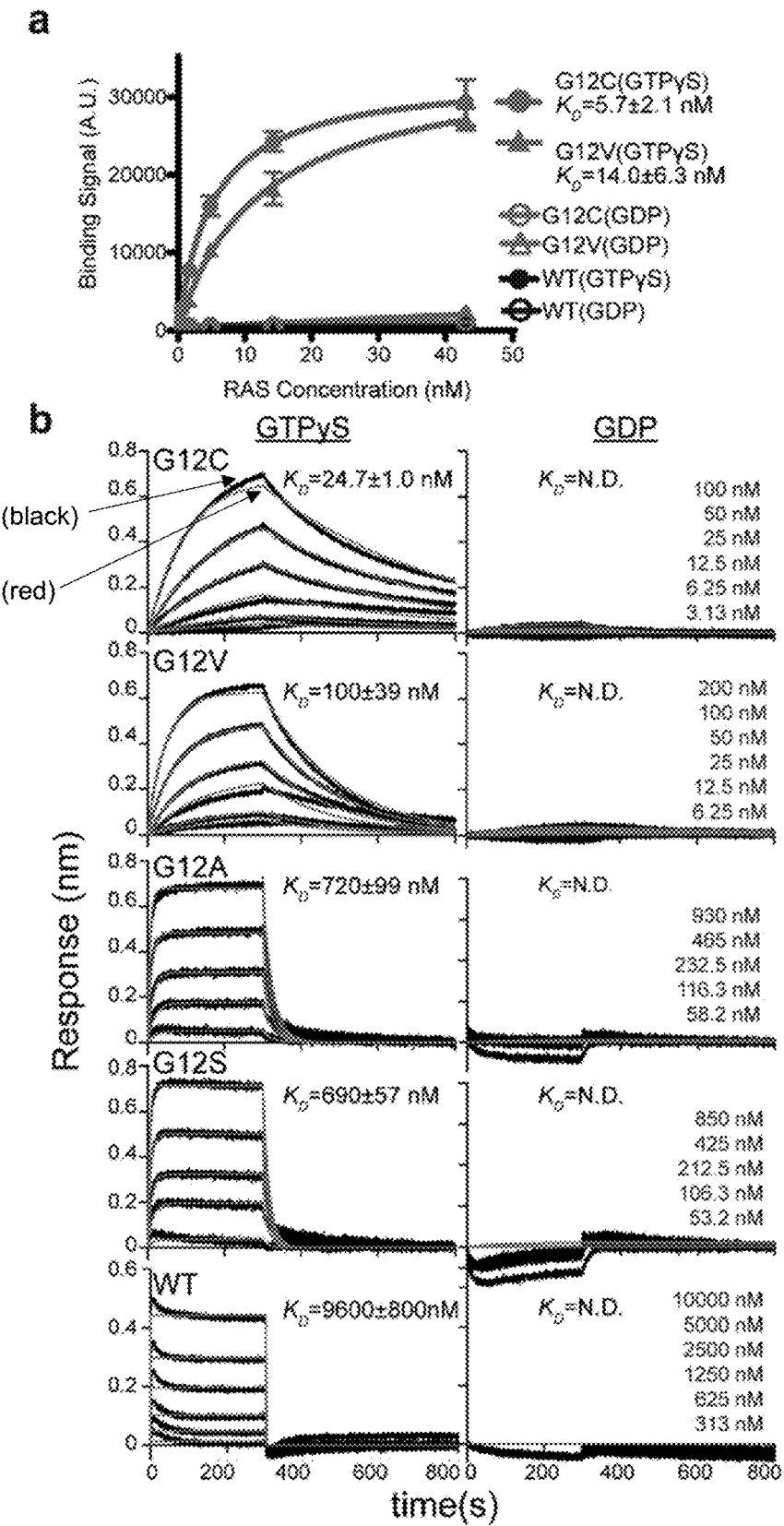
FIG. 1. Monobody 12VC1 is selective to G12 mutants of RAS harboring a small side chain. a, Binding titration of 12VC1 against purified RAS mutants. Binding of 12VC1 in a yeast display format against biotinylated KRAS(G12C), (G12V), and (WT) in either GTPγS or GDP-bound form labeled with neutravidin-Dylight 650 were measured with flow cytometry. Binding signals in arbitrary units (A.U.) are the median fluorescence intensity of the fluorescent population in the 75-95$^{th}$ percentile of the Dylight 650 detection channel. The apparent $K_D$ values shown are calculated by fitting the data points to the 1:1 binding model. Binding of GTPγS-bound WT and GDP-bound G12C, G12V, and WT were too weak to yield meaningful $K_D$. Errors in apparent $K_D$ and plotted data points are the standard deviation (s.d.), n=3, technical replicates. b, BLI sensorgrams of 12VC1 binding against different KRAS mutants and WT in GTPγS or GDP-loaded state. The experimental BLI traces (black) for G12C and G12V in the GTPγS-bound state were globally fitted (red) using the 1:1 binding kinetic model. Steady state global analysis was performed for KRAS G12A, G12S and WT. The $K_D$ values shown are the mean±s.d. from n=3, technical replicates. N.D., not determined due to too weak binding. c, Colocalization of mCherry fused 12VC1 (pseudo-color purple) with EGFP fused K-RAS(WT) and mutants (pseudo-color green). Scale bar denotes 10 μm. d, Pull-down assay with biotinylated 12VC1 and GST-RBD of lysates of cell lines containing KRAS(G12C) and (G12V) and (WT) with and without ARS1620 and EGF treatments. Captured proteins were probed using immunoblotting with a pan-RAS antibody. e, Affinity purified-mass spectrometry (AP-MS) analysis using 12VC1 as a capture reagent. SAINT score analysis and fold enrichment of each proteins that were uniquely present in the affinity purified sample of KRAS(G12V) harboring cell line (PATU8902) over non-KRAS mutant cell line (A375) were plotted. The data showed that 12VC1 captured overwhelmingly more KRAS (G12V) from PATU8902 than from A375. Red dot represents SAINT score and fold enrichment of KRAS(G12V). Dashed line signifies the cutoff for 5% false detection rate (FDR).
Figure 1:
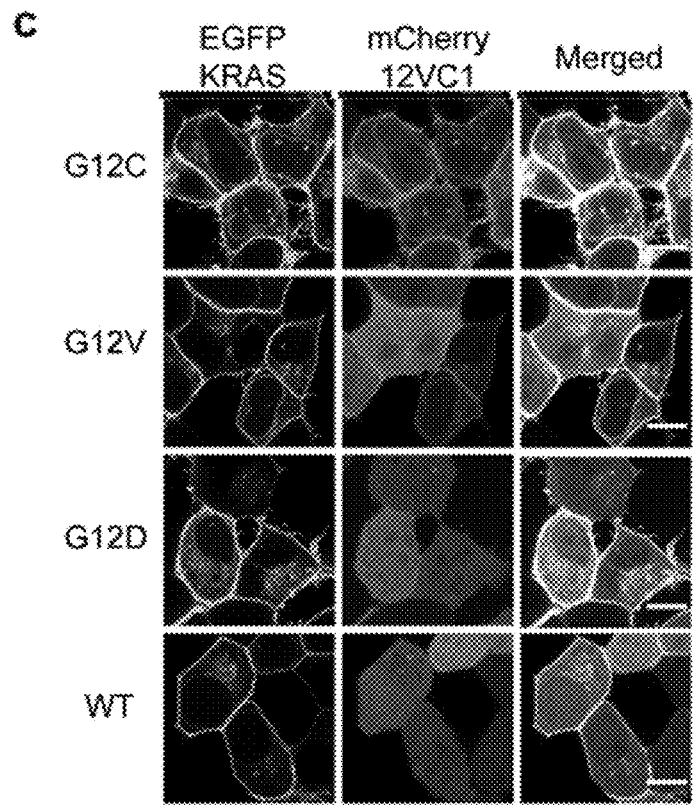
Figure 1:
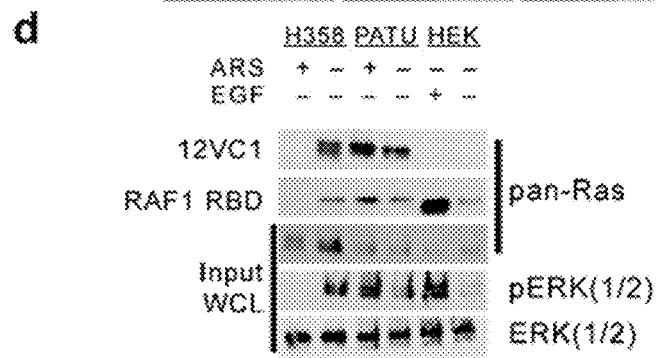
Figure 1:
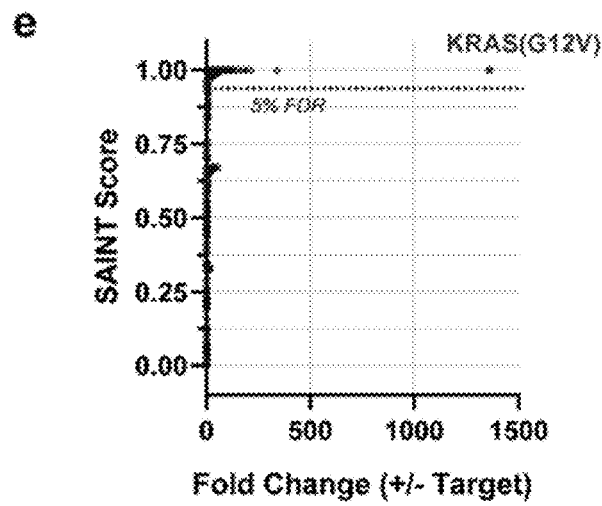

Although claimed subject matter will be described in terms of certain embodiments, other embodiments, including embodiments that do not provide all of the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

As used herein, the terms "including," "containing," and "comprising" are used in their open, non-limiting sense.

As used in this disclosure, the singular forms include the plural forms and vice versa unless the context clearly indicates otherwise.

The articles "a" and "an" are used in this disclosure to refer to one or more than one (i.e., to at least one) of the grammatical object of the article. By way of example, "an element" means one element or more than one element.

As used herein, unless otherwise stated or indicated, "s" refers to second(s), "min" refers to minute(s), and "h" refers to hour(s).

To provide a more concise description, some of the quantitative expressions given herein are not qualified with the term "about." It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. In an example, about refers to ±1%, ±2%, ±3%, ±4%, ±5%. ±6%, ±7%, ±8%, ±9%, ±10%, ±15%, or ±20%

The term "treatment" as used herein refers to reduction or delay in one or more symptoms or features associated with the presence of the particular condition being treated Treatment does not necessarily mean complete cure and does not preclude relapse, but may be used in connection with any such relapse.

The term "therapeutically effective amount" as used herein is the amount sufficient to achieve, in a single or multiple doses, the intended purpose of treatment. The exact amount desired or required will vary depending on the mode of administration, patient specifics and the like. Appropriate effective amounts can be determined by one of ordinary skill in the art (such as a clinician) with the benefit of the present disclosure.

The present disclosure also provides sequences that have homology with the protein or peptides sequences (including antibody sequences) described herein. In various examples, the homologous sequences have at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity with a protein or peptide sequence of the present disclosure.

The present disclosure provides proteins or peptides, which may be referred to as monobodies. Fusion proteins and proteolysis targeting chimeras (PROTACs) comprising the proteins or peptides are also provided. Also provided are compositions comprising proteins or peptides of the present disclosure, as well as fusion proteins and PROTACs. Methods of treating an individual in need of treatment are also provided. The methods may be to treat an individual suffering from or suspected of having KRAS(G12V), KRAS (G12S), KRAS(G12A) and/or KRAS(G12C)-associated cancers. A method may be for inhibiting ERK activation and/or proliferation of KRAS(G12V), KRAS(G12S), KRAS (G12A) and/or KRAS(G12C)-associated cancers. A method may be for reducing levels of endogenous RAS mutants. A method may also be for crystallizing a protein. A method may be for determining one or more potential drug(s) for treatment of KRAS(G12V), KRAS(G12S), KRAS(G12A) and/or KRAS(G12C)-associated cancers. A method may be for pulling down active RAS mutants.

In an aspect, the present disclosure provides proteins or peptides, which may be referred to as monobodies. The proteins or peptides may have the following sequence or comprise the following sequence or a comprise a truncated variant of the following sequence:
XXXVPTXLEVVAATXXSLLISWDAPAVTVXFYVIXY-GETGHGVGAFXAFXVXXXXS TATISGLXPGVDYTI-TVYARXXSKQGXYXPSPISINYRT (SEQ ID NO:26), where each X is an amino acid residue. X may be a canonical or non-canonical amino acid, such as, for example, a hydrophilic amino acid (e.g., a hydrophilic canonical amino acid or a hydrophilic non-canonical amino acid). In various examples, up to the first four residues at the N-terminus or C-terminus may be removed.

In various examples, the residues in bold are present in a protein or peptide of the present disclosure:

(SEQ ID NO: 26)
XXXVPTXLEVVAATXXSLLISWDAPAVTVXFYVIXYGETGHGVGAFXAFX

VXXXXS TATISGLXPGVDYTITVYARXXSKQGXYXPSPISINYRT.

In various examples, a peptide or protein may have the following sequence or comprise the following sequence or comprise a truncated variant of the following sequence:
VSSVPTKLEVVAATPTSLLISWDAPAVTVXFYVIXY-GETGHGVGAFXAFXVXXSKST ATISGLKPGVDYT-ITVYARXXSKQGXYXPSPISINYRT (SEQ ID NO:27), where each X is an amino acid residue, such as, for example, a hydrophilic amino acid (e.g., a hydrophilic canonical amino acid or a hydrophilic non-canonical amino acid). Each X may be the same or different. In various examples, up to the first four residues at the N-terminus or C-terminus may be removed.

In various other examples, a peptide or protein may have the following sequence or comprise the following sequence or comprise a truncated variant of the following sequence:
XXXVPTXLEVVAATXXSLLISWDAPAVTVFFYVITY-GETGHGVGAFQAFKVPGXXS TATISGLXPGVDY-TITVYARGYSKQGPYKPSPISINYRT (SEQ ID NO:28), where X is an amino acid residue, such as, for example, a hydrophilic amino acid (e.g., a hydrophilic canonical amino acid or a hydrophilic non-canonical amino acid). In various examples, up to the first four residues at the N-terminus or C-terminus may be removed. Each X may be the same or different.

In an aspect, a peptide or protein may have the following sequence or a truncated variant thereof or comprise the following sequence or comprise a truncated variant of the following sequence:
VSSVPTKLEVVAATPTSLLISWDAPAVTVFFYVITY-GETGHGVGAFQAFKVPGSKST ATISGLKPGVDYTI-TVYARGYSKQGPYKPSPISINYRT (12VC1) (SEQ ID NO:1); or a sequence with at least 75% homology, at least 80% homology, at least 85% homology, at least 90% homology, or at least 95% homology to 12VC1. SEQ ID NOs:26-28 represent variants of SEQ ID NO:1, where "X" represents amino acids of SEQ ID NO:1 that can be substituted (e.g., substituted by a hydrophilic amino acid). In various examples, variants of SEQ ID NO:1 have substitutions at the positions labeled X in SEQ ID NOs:26-28. In various examples, one or more (e.g., 1, 2, 3, 4, 5, or more) of the X residues in SEQ ID NOs: 26-28 differ from the corresponding amino acid residues in SEQ ID NO:1 (e.g., with alanine, or serine or another hydrophilic amino acid residue)). In various examples, all of the X residues in SEQ ID NOs: 26-28 differ from the corresponding amino acid residues in SEQ ID NO:1 (i.e., they have been substituted (e.g., with alanine, or serine or another hydrophilic amino acid residue)). Each X may be the same or different. For example, the hydrophilic amino acid residue is a canonical amino acid residue or a non-canonical amino acid residue. Examples of hydrophilic amino acids include, but are not limited to, arginine, glutamine, asparagine, threonine, tyrosine, and serine. In various examples, when a protein or peptide of the present disclosure has or comprises the following sequence or comprises a truncated variant of the following sequence: VSSVPTKLEVVAATPTSLLISWDAPAVTVFFYVITY-GETGHGVGAFQAFKVPGSKST ATISGLKPGVDYTI-TVYARGYSKQGPYKPSPISINYRT (12VC1) (SEQ ID NO:1), the bold residues are present (e.g., the same) in any variant sequence.

The proteins or peptides may be provided as a multivalent display or disposed (e.g., displayed) on a scaffold forming a multivalent display. Various examples of scaffolds include, but are not limited to, beads, resins, or membranes (e.g., cell membranes). In various examples, a protein or peptide may be provided on a yeast display. The one or more proteins or peptides may be the same or different.

In various examples, proteins or peptides of the present disclosure are non-covalently bound or covalently conjugated to one or more other proteins or peptides of the present disclosure. The one or more proteins or peptides may be the same or different. The resulting conjugate or oligomer may be a dimer, trimer, or the like.

In various examples, proteins or peptides of the present disclosure may be fused to a larger protein or peptide. Examples of larger proteins or peptides include, but are not limited to GFP, GFP variants, yeast Aga2, epitope tags, and the like.

In various examples, a peptide of the present disclosure has the following sequence or comprises any one of the following sequences or is a truncated variant of any one of the following sequences or is a variant (e.g., homolog) of any one of the following:

(SEQ ID NO: 1)
VSSVPTKLEVVAATPTSLLISWDAPAVTVFFYVITYGETGHGVGAFQAF

KVPGSKSTATISGLKPGVDYTITVYARGYSKQGPYKPSPISINYRT;

```
                                            (SEQ ID NO: 2)
VSSVPTELEVVAATPTSLLISWDAPAVTVFFYVITYGETGHGVGAFQAF

KVPGSRSTATISGLEPGVDYTITVYARGYSKQGPYKPSPISINYRT;

(SEQ ID NO: 3)
VSSVPTELEVVAATPTSLLISWDAPAVTVFFYVITYGETGHGVGAFQAF

AVPGSRSTATISGLEPGVDYTITVYARGYSKQGPYKPSPISINYRT;

(SEQ ID NO: 4)
VSSVPTKLEVVAATPTSLLISWDAPAVTVFFYIIAYGETGHGVGAFQAF

RVPGSKSTATISGLKPGVDYTITVYARGYSKQGPYKPSPISINYRT (12VC3);

(SEQ ID NO: 5)
VSSVPTKLEVVAATPTSLLISWDAPAVTVAFYVITYGETGHGVGAFQAF

KVPGSKSTATISGLKPGVDYTITVYARGYSKQGPYKPSPISINYRT;

(SEQ ID NO: 6)
VSSVPTKLEVVAATPTSLLISWDAPAVTVFAYVITYGETGHGVGAFQAF

KVPGSKSTATISGLKPGVDYTITVYARGYSKQGPYKPSPISINYRT;

(SEQ ID NO: 7)
VSSVPTKLEVVAATPTSLLISWDAPAVTVFFYAITYGETGHGVGAFQAF

KVPGSKSTATISGLKPGVDYTITVYARGYSKQGPYKPSPISINYRT;

(SEQ ID NO: 8)
VSSVPTKLEVVAATPTSLLISWDAPAVTVFFYVIAYGETGHGVGAFQAF

KVPGSKSTATISGLKPGVDYTITVYARGYSKQGPYKPSPISINYRT;

(SEQ ID NO: 9)
VSSVPTKLEVVAATPTSLLISWDAPAVTVFFYVITYGETGHGAGAFQAF

KVPGSKSTATISGLKPGVDYTITVYARGYSKQGPYKPSPISINYRT;

(SEQ ID NO: 10)
VSSVPTKLEVVAATPTSLLISWDAPAVTVFFYVITYGETGHGVGAAQAF

KVPGSKSTATISGLKPGVDYTITVYARGYSKQGPYKPSPISINYRT;

(SEQ ID NO: 11)
VSSVPTKLEVVAATPTSLLISWDAPAVTVFFYVITYGETGHGVGAFAAF

KVPGSKSTATISGLKPGVDYTITVYARGYSKQGPYKPSPISINYRT;

(SEQ ID NO: 12)
VSSVPTKLEVVAATPTSLLISWDAPAVTVFFYVITYGETGHGVGAFQAA

KVPGSKSTATISGLKPGVDYTITVYARGYSKQGPYKPSPISINYRT;

(SEQ ID NO: 13)
VSSVPTKLEVVAATPTSLLISWDAPAVTVFFYVITYGETGHGVGAFQAF

AVPGSKSTATISGLKPGVDYTITVYARGYSKQGPYKPSPISINYRT;

(SEQ ID NO: 14)
VSSVPTKLEVVAATPTSLLISWDAPAVTVFFYVITYGETGHGVGAFQAF

KVAGSKSTATISGLKPGVDYTITVYARGYSKQGPYKPSPISINYRT;

(SEQ ID NO: 15)
VSSVPTKLEVVAATPTSLLISWDAPAVTVFFYVITYGETGHGVGAFQAF

KVPASKSTATISGLKPGVDYTITVYARGYSKQGPYKPSPISINYRT;

(SEQ ID NO: 16)
VSSVPTKLEVVAATPTSLLISWDAPAVTVFFYVITYGETGHGVGAFQAF

KVPGSKSTATISGLKPGVDYTITVYARAYSKQGPYKPSPISINYRT;

(SEQ ID NO: 17)
VSSVPTKLEVVAATPTSLLISWDAPAVTVFFYVITYGETGHGVGAFQAF

KVPGSKSTATISGLKPGVDYTITVYARGASKQGPYKPSPISINYRT;

(SEQ ID NO: 18)
VSSVPTKLEVVAATPTSLLISWDAPAVTVFFYVITYGETGHGVGAFQAF

KVPGSKSTATISGLKPGVDYTITVYARGYSKQGAYKPSPISINYR;

(SEQ ID NO: 19)
VSSVPTKLEVVAATPTSLLISWDAPAVTVFFYVITYGETGHGVGAFQAF

KVPGSKSTATISGLKPGVDYTITVYARGYSKQGPAKPSPISINYRT;

or (SEQ ID NO: 20)
VSSVPTKLEVVAATPTSLLISWDAPAVTVFFYVITYGETGHGVGAFQAF

KVPGSKSTATISGLKPGVDYTITVYARGYSKQGPYAPSPISINYRT.
```

Examples of variants of SEQ ID NO:1 include, but are not limited to, SEQ ID NOs:2-20. SEQ ID NO:1 or variant may be a portion of a larger protein or attached to another compound or may be a truncated variant thereof. In various examples, the bolded residues do not change in any variants of the following sequences or a peptide or protein comprising any one of the following sequences or a truncated variant of any one of the following sequences:

```
                                            (SEQ ID NO: 1)
VSSVPTKLEVVAATPTSLLISWDAPAVTVFFYVITYGETGHGVGAFQAFK

VPGSKSTATISGLKPGVDYTITVYARGYSKQGPYKPSPISINYRT;

(SEQ ID NO: 2)
VSSVPTELEVVAATPTSLLISWDAPAVTVFFYVITYGETGHGVGAFQAFK

VPGSRSTATISGLEPGVDYTITVYARGYSKQGPYKPSPISINYRT;

(SEQ ID NO: 3)
VSSVPTELEVVAATPTSLLISWDAPAVTVFFYVITYGETGHGVGAFQAFA

VPGSRSTATISGLEPGVDYTITVYARGYSKQGPYKPSPISINYRT;

(SEQ ID NO: 4)
VSSVPTKLEVVAATPTSLLISWDAPAVTVFFYIIAYGETGHGVGAFQAFR

VPGSKSTATISGLKPGVDYTITVYARGYSKQGPYKPSPISINYRT (12VC3);

(SEQ ID NO: 5)
VSSVPTKLEVVAATPTSLLISWDAPAVTVAFYVITYGETGHGVGAFQAFK

VPGSKSTATISGLKPGVDYTITVYARGYSKQGPYKPSPISINYRT;

(SEQ ID NO: 6)
VSSVPTKLEVVAATPTSLLISWDAPAVTVFAYVITYGETGHGVGAFQAFK

VPGSKSTATISGLKPGVDYTITVYARGYSKQGPYKPSPISINYRT;

(SEQ ID NO: 7)
VSSVPTKLEVVAATPTSLLISWDAPAVTVFFYAITYGETGHGVGAFQAFK

VPGSKSTATISGLKPGVDYTITVYARGYSKQGPYKPSPISINYRT;

(SEQ ID NO: 8)
VSSVPTKLEVVAATPTSLLISWDAPAVTVFFYVIAYGETGHGVGAFQAFK

VPGSKSTATISGLKPGVDYTITVYARGYSKQGPYKPSPISINYRT;

(SEQ ID NO: 9)
VSSVPTKLEVVAATPTSLLISWDAPAVTVFFYVITYGETGHGAGAFQAFK

VPGSKSTATISGLKPGVDYTITVYARGYSKQGPYKPSPISINYRT;

(SEQ ID NO: 10)
VSSVPTKLEVVAATPTSLLISWDAPAVTVFFYVITYGETGHGVGAAQAFK

VPGSKSTATISGLKPGVDYTITVYARGYSKQGPYKPSPISINYRT;
```

```
                                                  (SEQ ID NO: 11)
VSSVPTKLEVVAATPTSLLISWDAPAVTVFFYVITYGETGHGVGAFAAFK

VPGSKSTATISGLKPGVDYTITVYARGYSKQGPYKPSPISINYRT;

(SEQ ID NO: 12)
VSSVPTKLEVVAATPTSLLISWDAPAVTVFFYVITYGETGHGVGAFQAAK

VPGSKSTATISGLKPGVDYTITVYARGYSKQGPYKPSPISINYRT;

(SEQ ID NO: 13)
VSSVPTKLEVVAATPTSLLISWDAPAVTVFFYVITYGETGHGVGAFQAFA

VPGSKSTATISGLKPGVDYTITVYARGYSKQGPYKPSPISINYRT;

(SEQ ID NO: 14)
VSSVPTKLEVVAATPTSLLISWDAPAVTVFFYVITYGETGHGVGAFQAFK

VAGSKSTATISGLKPGVDYTITVYARGYSKQGPYKPSPISINYRT;

(SEQ ID NO: 15)
VSSVPTKLEVVAATPTSLLISWDAPAVTVFFYVITYGETGHGVGAFQAFK

VPASKSTATISGLKPGVDYTITVYARGYSKQGPYKPSPISINYRT;

(SEQ ID NO: 16)
VSSVPTKLEVVAATPTSLLISWDAPAVTVFFYVITYGETGHGVGAFQAFK

VPGSKSTATISGLKPGVDYTITVYARAYSKQGPYKPSPISINYRT;

(SEQ ID NO: 17)
VSSVPTKLEVVAATPTSLLISWDAPAVTVFFYVITYGETGHGVGAFQAFK

VPGSKSTATISGLKPGVDYTITVYARGASKQGPYKPSPISINYRT;

(SEQ ID NO: 18)
VSSVPTKLEVVAATPTSLLISWDAPAVTVFFYVITYGETGHGVGAFQAFK

VPGSKSTATISGLKPGVDYTITVYARGYSKQGAYKPSPISINYR;

(SEQ ID NO: 19)
VSSVPTKLEVVAATPTSLLISWDAPAVTVFFYVITYGETGHGVGAFQAFK

VPGSKSTATISGLKPGVDYTITVYARGYSKQGPAKPSPISINYRT;
or (SEQ ID NO: 20)
VSSVPTKLEVVAATPTSLLISWDAPAVTVFFYVITYGETGHGVGAFQAFK

VPGSKSTATISGLKPGVDYTITVYARGYSKQGPYAPSPISINYRT.
```

A protein or peptide of the present disclosure may be modified at various locations on the protein or peptide. For example, a protein or peptide may be modified at a sidechain of one or more amino acid residue(s), the C-terminus, the N-terminus, or a combination thereof. For example, Cys residues may be modified site specifically using a reagent that is reactive with a Cys residue (e.g., maleimide). Examples of modification include, but are not limited to, PEGylation, biotinylation, conjugation of dyes, conjugation of E3 ligase ligands, small molecules (e.g., small molecule drugs), and the like, and combinations thereof. In various examples, lysines, series, glutamic acids, and the N-terminus of a protein or peptide may be modified such that the binding interface is not disrupted.

The peptides or proteins can be synthesized via methods known in the art (e.g., recombinant expression or solid phase peptide synthesis (SPPS)). Depending on the vector utilized, any of a number of suitable transcription and translation elements, including constitutive and inducible promoters, transcription enhancer elements, transcription terminators, etcetera, may be used in the expression vector. Such construction of expression vectors and the expression of genes in transfected cells can involve the use of molecular cloning techniques (for example, in vitro recombinant DNA techniques, synthetic techniques, and in vivo recombination/genetic recombination), bacterial systems for the expression of vectors, yeast systems with constitutive or inducible promoters, insect systems, prokaryotic and eukaryotic systems using transfection or co-transfections of DNA vectors, transgenic animals using for example viral infection, and embryonic stem cells. Methods and procedures for using and applying such vectors are widespread in publications and are known or easily obtainable by persons of ordinary skill in the art. Both Boc and Fmoc SPPS chemistries may be used.

In an aspect, the present disclosure provides a fusion protein or PROTAC comprising a protein or peptide of the present disclosure.

A fusion protein or PROTAC may comprise an E3 ligase subunit or fragment of an E3 subunit. Examples of an E3 ligase are Von Hippel-Lindau tumor suppressor (VHL), cereblon (CRBN), mouse double minute 2 (MDM2), cellular inhibitor of apoptosis (cIAP), and speckle-type POZ protein (SPOP). Various other E3 ligases are known in the art. Examples of fusion partners include the UBOX domain of the CHIP E3 ligase. Small molecules include VHL ligand, pomalidomide (CRBN ligand), Bestatin (cIAP ligand), Nutlin-3a (MDM2 ligand), and the like. Examples of peptides that target E3 ligase include, but are not limited to, HIF-1alpha (VHL directing peptide).

In an aspect, the present disclosure provides compositions comprising proteins, peptides, fusion proteins, and/or PROTACs of the present disclosure. The compositions further comprise one or more pharmaceutically acceptable carriers.

A composition may comprise additional components. For example, the composition comprises a buffer solution suitable for administration to an individual (e.g., a mammal such as, for example, a human or a non-human). An individual may be a subject. The buffer solution may be a pharmaceutically acceptable carrier.

A composition may include one or more standard pharmaceutically acceptable carrier(s). Non-limiting examples of compositions include solutions, suspensions, emulsions, solid injectable compositions that are dissolved or suspended in a solvent before use, and the like. Injections may be prepared by dissolving, suspending, or emulsifying one or more of the active ingredient(s) in a diluent. Non-limiting examples of diluents include distilled water for injection, physiological saline, vegetable oil, alcohol, and the like, and combinations thereof. Further, injections may contain stabilizers, solubilizers, suspending agents, emulsifiers, soothing agents, buffers, preservatives, and the like. Injections may be sterilized in the final formulation step or prepared by sterile procedure. The composition may also be formulated into a sterile solid preparation, for example, by freeze-drying, and can be used after sterilized or dissolved in sterile injectable water or other sterile diluent(s) immediately before use. Non-limiting examples of pharmaceutically acceptable carriers can be found in: *Remington: The Science and Practice of Pharmacy* (2012) 22nd Edition, Philadelphia, PA Lippincott Williams & Wilkins.

Acceptable carriers, excipients, or stabilizers are nontoxic to recipients at the dosages and concentrations employed, and include, but are not limited to, buffers such as, for example, phosphate, citrate, histidine and other organic acids; antioxidants including, but not limited to, ascorbic acid and methionine; preservatives (such as, for example, octadecyldimethylbenzyl ammonium chloride; hexamethonium chloride; benzalkonium chloride, benzethonium chloride; phenol, butyl or benzyl alcohol; alkyl parabens such as, for example, methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids, such as, for example, glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, polyethylene glycol (PEG) and the like. In an embodiment, the pharmaceutical composition may comprise buffer components and stabilizers, including, but not limited to, sucrose, polysorbate 20, NaCl, KCl, sodium acetate, sodium phosphate, arginine, lysine, trehalose, glycerol, and maltose.

In an aspect, the present disclosure provides a method for treating an individual having or suspected of having KRAS (G12V), KRAS(G12S), KRAS(G12A) and/or KRAS (G12C)-associated cancers. Also provided are methods of reducing levels of endogenous RAS mutants and/or inhibiting ERK activation and/or proliferation of KRAS(G12V), KRAS(G12S), KRAS(G12A), and/or KRAS(G12C)-associated cancers.

Examples of KRAS(G12V), KRAS(G12S), KRAS (G12A) and/or KRAS(G12C)-associated cancers include, but are not limited to, non-small cell lung cancer (NSCLC), colorectal cancer (CRC), pancreatic cancer (PDAC), uterine cancer, and gastric cancer.

A method for treating an individual having or suspected of having KRAS(G12V), KRAS(G12S), KRAS(G12A) and/or KRAS(G12C)-associated cancers and/or reducing levels of endogenous RAS mutants may comprise: administering to a subject who has been diagnosed with or is suspected of having KRAS(G12V)- and/or KRAS(G12C)-associated cancers a therapeutically effective amount of: i) a protein or peptide of the present disclosure, and optionally a carrier protein; ii) an mRNA capable of encoding a protein or peptide of the present disclosure; iii) a DNA capable of encoding a protein or peptide of the present disclosure; iv) a microorganism (e.g., virus or bacteria) that carries the gene for a protein or peptide of the present disclosure; v) a fusion protein or PROTAC of the present disclosure; vi) a composition of the present disclosure vii) an mRNA capable of encoding a fusion protein or PROTAC comprising a protein or peptide of the present disclosure; viii) a DNA capable of encoding a fusion protein or PROTAC comprising a protein or peptide of the present disclosure; or ix) a microorganism that carries the gene for a fusion protein or PROTAC comprising a protein or peptide of the present disclosure.

A protein or peptide of the present disclosure may be administered to an individual by various means. For example, the peptides can be administered directly or within a pharmaceutical agent or in combination with other delivery agents. Alternatively, in another embodiment, an expression vector can be used. Including, but not limited to, to a variety of viral-based vector systems, non-limiting examples of which include, adenoviral vectors and adenoviral-associated vectors and oncolytic vectors. In another embodiment, mRNA encoding a protein or peptide of the present disclosure or DNA encoding a protein or peptide of the present disclosure may be administered to an individual in need of treatment. A protein or peptide may be delivered on its own or with a carrier protein.

A method for treating an individual having or suspected of having KRAS(G12V), KRAS(G12S), KRAS(G12A) and/or KRAS(G12C)-associated cancers may be carried out in combination with one or more known therapy(ies), including, but not limited to, surgery, radiation therapy, chemotherapy, photodynamic therapy, and/or immunotherapy.

The proteins or peptides may be administered by various means. Administration of the proteins or peptides (including as compositions) as described herein can be carried out using any suitable route of administration known in the art. For example, the compositions may be administered via intravenous, intramuscular, intraperitoneal, intracerobrospinal, subcutaneous, intra-articular, intrasynovial, oral, or topical. The compositions may be administered parenterally or enterically. The compositions may be introduced as a single administration or as multiple administrations or may be introduced in a continuous manner over a period of time. For example, the administration(s) can be a pre-specified number of administrations or daily, weekly or monthly administrations, which may be continuous or intermittent, as may be clinically needed and/or therapeutically indicated.

In various examples, a subject in need of treatment is administered a therapeutically effective amount of a composition of the present disclosure. A dose of a therapeutically effective amount of a protein, peptide, fusion protein, or PROTAC of the present disclosure may have a concentration of 1 nM to 10 mM, including all 0.1 nM values and ranges therebetween.

The compositions may be administered to an individual or subject in need of treatment such as a human or a non-human animal. An individual in need of treatment may be a human. In other examples, the individual is a non-human mammal or other animal. Non-limiting examples of non-human mammals include cows, horses, pigs, mice, rats, rabbits, cats, dogs, or other agricultural mammals, pets, or service animals, and the like.

In an aspect, the present disclosure provides a method of crystallizing a protein. A method for crystallizing a protein comprises contacting the protein with a protein or peptide of the present disclosure, where the binding results in crystallization of the protein.

In an aspect, the present disclosure provides a method for determining one or more potential drug(s) for treatment of KRAS(G12V), KRAS(G12S), KRAS(G12A) and/or KRAS (G12C)-associated cancers.

A method may comprise structure guided design based on crystal structures of the protein or peptide-RAS mutant complexes; screening the compounds that displace the protein or peptide from RAS; and quantifying the amount of active RAS using the protein or peptide of the present disclosure after treatment with the compounds.

The steps of the method described in the various embodiments and examples disclosed herein are sufficient to carry out the methods of the present disclosure. Thus, in an embodiment, the method consists essentially of a combination of the steps of the methods disclosed herein. In another embodiment, the method consists of such steps.

The following Statements provide examples of the present disclosure:

Statement 1. A protein or peptide (which may be referred to a monobody) comprising: i) the following sequence: VSSVPTKLEVVAATPTSLLISWDAPAVTVFFYVI-TYGETGHGV GAFQAFKVPGSKSTATIS-GLKPGVDYTITVYARGYSKQGPYKPSPISINYRT (12VC1) (SEQ ID NO:1); or ii) a sequence with at least 75% homology, at least 80% homology, at least 85% homology, at least 90% homology, or at least 95% homology to 12VC1.

Statement 2. A protein or peptide according to Statement 1, wherein one or more of the proteins or peptides are disposed (e.g., displayed) on a bead or resin or membrane (e.g., cell membrane).

Statement 3. A protein or peptide according to Statement 1, wherein a yeast display is used to display one or more proteins or peptides of Statement 1.

Statement 4. A protein or peptide according to Statement 1, wherein the protein or peptide is non-covalently bound and/or covalently conjugated to one or more other proteins and peptides such that a dimer, trimer, or the like is formed. In various examples, combination of proteins or peptides are an oligomer.

Statement 5. A protein or peptide according to Statement 1, wherein the protein or peptide is fused to a larger protein or peptide.

Statement 6. A protein or peptide according to Statement 1, wherein the larger protein or peptide is GFP, a GFP variant, yeast Aga2, an epitope tag, and the like.

Statement 7. A protein or peptide (which may be referred to a monobody) according to any of the preceding claims, wherein the homological sequence is:

```
                                       (SEQ ID NO: 2)
VSSVPTELEVVAATPTSLLISWDAPAVTVFFYVITYGETGHGVGAFQAFK
VPGSRSTATISGLEPGVDYTITVYARGYSKQGPYKPSPISINYRT;

(SEQ ID NO: 3)
VSSVPTELEVVAATPTSLLISWDAPAVTVFFYVITYGETGHGVGAFQAFA
VPGSRSTATISGLEPGVDYTITVYARGYSKQGPYKPSPISINYRT;

(SEQ ID NO: 4)
VSSVPTKLEVVAATPTSLLISWDAPAVTVFFYIIAYGETGHGVGAFQAFR
VPGSKSTATISGLKPGVDYTITVYARGYSKQGPYKPSPISINYRT;

(SEQ ID NO: 5)
VSSVPTKLEVVAATPTSLLISWDAPAVTVAFYVITYGETGHGVGAFQAFK
VPGSKSTATISGLKPGVDYTITVYARGYSKQGPYKPSPISINYRT;

(SEQ ID NO: 6)
VSSVPTKLEVVAATPTSLLISWDAPAVTVFAYVITYGETGHGVGAFQAFK
VPGSKSTATISGLKPGVDYTITVYARGYSKQGPYKPSPISINYRT;

(SEQ ID NO: 7)
VSSVPTKLEVVAATPTSLLISWDAPAVTVFFYAITYGETGHGVGAFQAFK
VPGSKSTATISGLKPGVDYTITVYARGYSKQGPYKPSPISINYRT;

(SEQ ID NO: 8)
VSSVPTKLEVVAATPTSLLISWDAPAVTVFFYVIAYGETGHGVGAFQAFK
VPGSKSTATISGLKPGVDYTITVYARGYSKQGPYKPSPISINYRT;

(SEQ ID NO: 9)
VSSVPTKLEVVAATPTSLLISWDAPAVTVFFYVITYGETGHGAGAFQAFK
VPGSKSTATISGLKPGVDYTITVYARGYSKQGPYKPSPISINYRT;

(SEQ ID NO: 10)
VSSVPTKLEVVAATPTSLLISWDAPAVTVFFYVITYGETGHGVGAAQAFK
VPGSKSTATISGLKPGVDYTITVYARGYSKQGPYKPSPISINYRT;

(SEQ ID NO: 11)
VSSVPTKLEVVAATPTSLLISWDAPAVTVFFYVITYGETGHGVGAFAAFK
VPGSKSTATISGLKPGVDYTITVYARGYSKQGPYKPSPISINYRT;

(SEQ ID NO: 12)
VSSVPTKLEVVAATPTSLLISWDAPAVTVFFYVITYGETGHGVGAFQAAK
VPGSKSTATISGLKPGVDYTITVYARGYSKQGPYKPSPISINYRT;

(SEQ ID NO: 13)
VSSVPTKLEVVAATPTSLLISWDAPAVTVFFYVITYGETGHGVGAFQAFA
VPGSKSTATISGLKPGVDYTITVYARGYSKQGPYKPSPISINYRT;

(SEQ ID NO: 14)
VSSVPTKLEVVAATPTSLLISWDAPAVTVFFYVITYGETGHGVGAFQAFK
VAGSKSTATISGLKPGVDYTITVYARGYSKQGPYKPSPISINYRT;

(SEQ ID NO: 15)
VSSVPTKLEVVAATPTSLLISWDAPAVTVFFYVITYGETGHGVGAFQAFK
VPASKSTATISGLKPGVDYTITVYARGYSKQGPYKPSPISINYRT;

(SEQ ID NO: 16)
VSSVPTKLEVVAATPTSLLISWDAPAVTVFFYVITYGETGHGVGAFQAFK
VPGSKSTATISGLKPGVDYTITVYARAYSKQGPYKPSPISINYRT;

(SEQ ID NO: 17)
VSSVPTKLEVVAATPTSLLISWDAPAVTVFFYVITYGETGHGVGAFQAFK
VPGSKSTATISGLKPGVDYTITVYARGASKQGPYKPSPISINYRT;

(SEQ ID NO: 18)
VSSVPTKLEVVAATPTSLLISWDAPAVTVFFYVITYGETGHGVGAFQAFK
VPGSKSTATISGLKPGVDYTITVYARGYSKQGAYKPSPISINYR;

(SEQ ID NO: 19)
VSSVPTKLEVVAATPTSLLISWDAPAVTVFFYVITYGETGHGVGAFQAFK
VPGSKSTATISGLKPGVDYTITVYARGYSKQGPAKPSPISINYRT;
or
                                      (SEQ ID NO: 20)
VSSVPTKLEVVAATPTSLLISWDAPAVTVFFYVITYGETGHGVGAFQAFK
VPGSKSTATISGLKPGVDYTITVYARGYSKQGPYAPSPISINYRT.
```

Statement 8. A protein or peptide (which may be referred to a monobody) according to any one of the preceding claims, wherein the protein or peptide has the following sequence or comprises the following sequence:

```
                                       (SEQ ID NO: 2)
VSSVPTELEVVAATPTSLLISWDAPAVTVFFYVITYGETGHGVGAFQAFK
VPGSRSTATISGLEPGVDYTITVYARGYSKQGPYKPSPISINYRT;

(SEQ ID NO: 3)
VSSVPTELEVVAATPTSLLISWDAPAVTVFFYVITYGETGHGVGAFQAFA
VPGSRSTATISGLEPGVDYTITVYARGYSKQGPYKPSPISINYRT;

(SEQ ID NO: 4)
VSSVPTKLEVVAATPTSLLISWDAPAVTVFFYIIAYGETGHGVGAFQAFR
VPGSKSTATISGLKPGVDYTITVYARGYSKQGPYKPSPISINYRT;

(SEQ ID NO: 5)
VSSVPTKLEVVAATPTSLLISWDAPAVTVAFYVITYGETGHGVGAFQAFK
VPGSKSTATISGLKPGVDYTITVYARGYSKQGPYKPSPISINYRT;

(SEQ ID NO: 6)
VSSVPTKLEVVAATPTSLLISWDAPAVTVFAYVITYGETGHGVGAFQAFK
VPGSKSTATISGLKPGVDYTITVYARGYSKQGPYKPSPISINYRT;

(SEQ ID NO: 7)
VSSVPTKLEVVAATPTSLLISWDAPAVTVFFYAITYGETGHGVGAFQAFK
VPGSKSTATISGLKPGVDYTITVYARGYSKQGPYKPSPISINYRT;
```

-continued

```
                                                (SEQ ID NO: 8)
VSSVPTKLEVVAATPTSLLISWDAPAVTVFFYVIAYGETGHGVGAFQAFK

VPGSKSTATISGLKPGVDYTITVYARGYSKQGPYKPSPISINYRT;

(SEQ ID NO: 9)
VSSVPTKLEVVAATPTSLLISWDAPAVTVFFYVITYGETGHGAGAFQAFK

VPGSKSTATISGLKPGVDYTITVYARGYSKQGPYKPSPISINYRT;

(SEQ ID NO: 10)
VSSVPTKLEVVAATPTSLLISWDAPAVTVFFYVITYGETGHGVGAAQAFK

VPGSKSTATISGLKPGVDYTITVYARGYSKQGPYKPSPISINYRT;

(SEQ ID NO: 11)
VSSVPTKLEVVAATPTSLLISWDAPAVTVFFYVITYGETGHGVGAFAAFK

VPGSKSTATISGLKPGVDYTITVYARGYSKQGPYKPSPISINYRT;

(SEQ ID NO: 12)
VSSVPTKLEVVAATPTSLLISWDAPAVTVFFYVITYGETGHGVGAFQAAK

VPGSKSTATISGLKPGVDYTITVYARGYSKQGPYKPSPISINYRT;

(SEQ ID NO: 13)
VSSVPTKLEVVAATPTSLLISWDAPAVTVFFYVITYGETGHGVGAFQAFA

VPGSKSTATISGLKPGVDYTITVYARGYSKQGPYKPSPISINYRT;

(SEQ ID NO: 14)
VSSVPTKLEVVAATPTSLLISWDAPAVTVFFYVITYGETGHGVGAFQAFK

VAGSKSTATISGLKPGVDYTITVYARGYSKQGPYKPSPISINYRT;

(SEQ ID NO: 15)
VSSVPTKLEVVAATPTSLLISWDAPAVTVFFYVITYGETGHGVGAFQAFK

VPASKSTATISGLKPGVDYTITVYARGYSKQGPYKPSPISINYRT;

(SEQ ID NO: 16)
VSSVPTKLEVVAATPTSLLISWDAPAVTVFFYVITYGETGHGVGAFQAFK

VPGSKSTATISGLKPGVDYTITVYARAYSKQGPYKPSPISINYRT;

(SEQ ID NO: 17)
VSSVPTKLEVVAATPTSLLISWDAPAVTVFFYVITYGETGHGVGAFQAFK

VPGSKSTATISGLKPGVDYTITVYARGASKQGPYKPSPISINYRT;

(SEQ ID NO: 18)
VSSVPTKLEVVAATPTSLLISWDAPAVTVFFYVITYGETGHGVGAFQAFK

VPGSKSTATISGLKPGVDYTITVYARGYSKQGAYKPSPISINYR;

(SEQ ID NO: 19)
VSSVPTKLEVVAATPTSLLISWDAPAVTVFFYVITYGETGHGVGAFQAFK

VPGSKSTATISGLKPGVDYTITVYARGYSKQGPAKPSPISINYRT;
or
                                                (SEQ ID NO: 20)
VSSVPTKLEVVAATPTSLLISWDAPAVTVFFYVITYGETGHGVGAFQAFK

VPGSKSTATISGLKPGVDYTITVYARGYSKQGPYAPSPISINYRT.
```

Statement 9. A protein or peptide (which may be referred to a monobody) according to any one of the preceding Statements, wherein the protein or peptide is modified at a sidechain of one or more amino acid residue(s), the C-terminus, the N-terminus, or a combination thereof.

Statement 10. A fusion protein or proteolysis targeting chimera (PROTAC) comprising a protein or peptide according to any one of the preceding Statements.

Statement 11. A fusion protein or PROTAC according to Statement 10, further comprising an E3 ligase subunit or fragment of an E3 subunit.

Statement 12. A fusion protein or PROTAC according to Statement 11, wherein the E3 ligase is Von Hippel-Lindau tumor suppressor (VHL). Fusion partners for a fusion protein include UBOX domain of the CHIP E3 ligase. Possible small molecules that may be utilized include: VHL ligands, pomalidomide (CRBN ligand), Bestatin (cIAP ligand), Nutlin-3a (MDM2 ligand). Possible peptides that may be utilized include peptides that targets subunits of E3 ligase, e.g., HIF-1alpha (VHL directing peptide).

Statement 13. A composition comprising a protein or peptide according to any one of Statements 1-9 and a pharmaceutically acceptable carrier.

Statement 14. A composition comprising a fusion protein or PROTAC according to any one of Statements 10-12 and a pharmaceutically acceptable carrier.

Statement 15. A method for treating KRAS(G12V), KRAS(G12S), KRAS(G12A) and/or KRAS(G12C)-associated cancers comprising: administering to a subject who has been diagnosed with or is suspected of having KRAS(G12V), KRAS(G12S), KRAS(G12A) and/or KRAS(G12C)-associated cancers a therapeutically effective amount of:

i) a protein or peptide according to any one of Statements 1-9, and optionally a carrier protein; ii) an mRNA capable of encoding a protein or peptide according to any one of Statements 1-9; iii) a DNA capable of encoding a protein or peptide according to any one of Statements 1-9; iv) a microorganism (e.g., virus or bacteria) that carries the gene for a protein or peptide according to any one of Statements 1-9; v) a fusion protein or PROTAC according to any one of Statements 10-12; or vi) a composition according to Statement 13 or Statement 14, wherein the subject's cancer is treated.

Statement 16. A method for inhibiting ERK activation and/or proliferation of KRAS(G12V), KRAS(G12S), KRAS(G12A) and/or KRAS(G12C)-associated cancers comprising:

contacting one or more KRAS(G12V), KRAS(G12S), KRAS(G12A) and/or KRAS(G12C)-associated cancer cells with a therapeutically effective amount of i) a protein or peptide according to any one of Statements 1-9, and optionally a carrier protein; ii) an mRNA capable of encoding a protein or peptide according to any one of Statements 1-9; iii) a DNA capable of encoding a protein or peptide according to any one of Statements 1-9; iv) a microorganism (e.g., virus or bacteria) that carries the gene for a protein or peptide according to any one of Statements 1-9; v) a fusion protein or PROTAC according to any one of Statements 10-12; or vi) a composition according to Statement 13 or Statement 14, wherein ERK activation is and/or proliferation of KRAS(G12V), KRAS(G12S), KRAS(G12A), and/or KRAS(G12C)-associated cancers is inhibited.

Statement 17. A method for reducing levels of endogenous RAS mutants comprising: administering to a subject who has been diagnosed with or is suspected of having KRAS(G12V), KRAS(G12S), KRAS(G12A), and/or KRAS(G12C)-associated cancers a therapeutically effective amount of i) a protein or peptide according to any one of Statements 1-9, and optionally a carrier protein; ii) an mRNA capable of encoding a protein or peptide according to any one of Statements 1-9; iii) a DNA capable of encoding a protein or peptide according to any one of Statements 1-9; iv) a microorganism (e.g., virus or bacteria) that carries the gene for a protein or peptide according to any one of Statements 1-9; v) a fusion protein or PROTAC according to any one of Statements 10-12; or vi) a composition according to Statement 13 or Statement 14, wherein the levels of endogenous RAS mutant are reduced.

Statement 18. A method for crystallizing a protein comprising: contacting the protein with a protein or peptide according to any one of Statements 1-9, wherein binding of the protein to the protein or peptide according to any one of Statements 1-9 results in crystallization of the protein.

Statement 19. A method for determining one or more potential drug(s) for treatment of KRAS(G12V)- and/or KRAS(G12C)-associated cancers, comprising:
(1) designed compounds through structure-guided design based on the crystal structures of protein or peptide-RAS mutant (e.g., 12VC1-RAS mutant) complexes;
(2) screening for molecules that displace the monobody from RAS; and
(3) quantifying the amount of active RAS using the monobody after treatment with compounds.

Statement 20. A protein or peptide comprising or having:
i) the following sequence:
VSSVPTKLEVVAATPTSLLISWDAPAVTVFFYVITYGETGHGVGAFQAFKVPGSKSTATISGLKPGVDYTITVYARGYSKQGPYKPSPISINYRT (12VC1) (SEQ ID NO:1) or a truncated variant thereof; or ii) a variant with at least 80% homology to SEQ ID NO:1.

Statement 21. A protein or peptide according to claim Statement 21, where one or more of the proteins or peptides are disposed on a bead or resin or membrane or where a yeast display is used to display the one or more proteins or peptides or where the protein or peptide is non-covalently bound and/or covalently conjugated to one or more other proteins and peptides such that a dimer, trimer, or oligomer is formed.

Statement 22. A protein or peptide according to Statement 20 or 21, wherein the protein or peptide is fused to a larger protein or peptide.

Statement 23. A protein or peptide according to Statement 22, wherein the larger protein or peptide is GFP, a GFP variant, yeast Aga2, or an epitope tag.

Statement 24. The protein or peptide according to any one of Statements 20-23 1, wherein the variant is:

(SEQ ID NO: 2)
VSSVPTELEVVAATPTSLLISWDAPAVTVFFYVITYGETGHGVGAFQAFK

VPGSRSTATISGLEPGVDYTITVYARGYSKQGPYKPSPISINYRT;

(SEQ ID NO: 3)
VSSVPTELEVVAATPTSLLISWDAPAVTVFFYVITYGETGHGVGAFQAFA

VPGSRSTATISGLEPGVDYTITVYARGYSKQGPYKPSPISINYRT;

(SEQ ID NO: 4)
VSSVPTKLEVVAATPTSLLISWDAPAVTVFFYIIAYGETGHGVGAFQAFR

VPGSKSTATISGLKPGVDYTITVYARGYSKQGPYKPSPISINYRT;

(SEQ ID NO: 5)
VSSVPTKLEVVAATPTSLLISWDAPAVTVAFYVITYGETGHGVGAFQAFK

VPGSKSTATISGLKPGVDYTITVYARGYSKQGPYKPSPISINYRT;

(SEQ ID NO: 6)
VSSVPTKLEVVAATPTSLLISWDAPAVTVFAYVITYGETGHGVGAFQAFK

VPGSKSTATISGLKPGVDYTITVYARGYSKQGPYKPSPISINYRT;

(SEQ ID NO: 7)
VSSVPTKLEVVAATPTSLLISWDAPAVTVFFYAITYGETGHGVGAFQAFK

VPGSKSTATISGLKPGVDYTITVYARGYSKQGPYKPSPISINYRT;

(SEQ ID NO: 8)
VSSVPTKLEVVAATPTSLLISWDAPAVTVFFYVIAYGETGHGVGAFQAFK

VPGSKSTATISGLKPGVDYTITVYARGYSKQGPYKPSPISINYRT;

(SEQ ID NO: 9)
VSSVPTKLEVVAATPTSLLISWDAPAVTVFFYVITYGETGHGAGAFQAFK

VPGSKSTATISGLKPGVDYTITVYARGYSKQGPYKPSPISINYRT;

(SEQ ID NO: 10)
VSSVPTKLEVVAATPTSLLISWDAPAVTVFFYVITYGETGHGVGAAQAFK

VPGSKSTATISGLKPGVDYTITVYARGYSKQGPYKPSPISINYRT;

(SEQ ID NO: 11)
VSSVPTKLEVVAATPTSLLISWDAPAVTVFFYVITYGETGHGVGAFAAFK

VPGSKSTATISGLKPGVDYTITVYARGYSKQGPYKPSPISINYRT;

(SEQ ID NO: 12)
VSSVPTKLEVVAATPTSLLISWDAPAVTVFFYVITYGETGHGVGAFQAAK

VPGSKSTATISGLKPGVDYTITVYARGYSKQGPYKPSPISINYRT;

(SEQ ID NO: 13)
VSSVPTKLEVVAATPTSLLISWDAPAVTVFFYVITYGETGHGVGAFQAFA

VPGSKSTATISGLKPGVDYTITVYARGYSKQGPYKPSPISINYRT;

(SEQ ID NO: 14)
VSSVPTKLEVVAATPTSLLISWDAPAVTVFFYVITYGETGHGVGAFQAFK

VAGSKSTATISGLKPGVDYTITVYARGYSKQGPYKPSPISINYRT;

(SEQ ID NO: 15)
VSSVPTKLEVVAATPTSLLISWDAPAVTVFFYVITYGETGHGVGAFQAFK

VPASKSTATISGLKPGVDYTITVYARGYSKQGPYKPSPISINYRT;

(SEQ ID NO: 16)
VSSVPTKLEVVAATPTSLLISWDAPAVTVFFYVITYGETGHGVGAFQAFK

VPGSKSTATISGLKPGVDYTITVYARAYSKQGPYKPSPISINYRT;

(SEQ ID NO: 17)
VSSVPTKLEVVAATPTSLLISWDAPAVTVFFYVITYGETGHGVGAFQAFK

VPGSKSTATISGLKPGVDYTITVYARGASKQGPYKPSPISINYRT;

(SEQ ID NO: 18)
VSSVPTKLEVVAATPTSLLISWDAPAVTVFFYVITYGETGHGVGAFQAFK

VPGSKSTATISGLKPGVDYTITVYARGYSKQGAYKPSPISINYR;

(SEQ ID NO: 19)
VSSVPTKLEVVAATPTSLLISWDAPAVTVFFYVITYGETGHGVGAFQAFK

VPGSKSTATISGLKPGVDYTITVYARGYSKQGPAKPSPISINYRT;

(SEQ ID NO: 20)
VSSVPTKLEVVAATPTSLLISWDAPAVTVFFYVITYGETGHGVGAFQAFK

VPGSKSTATISGLKPGVDYTITVYARGYSKQGPYAPSPISINYRT;

or truncated variant thereof.

Statement 25. A protein or peptide according to any one of Statements 20-24, wherein the protein or peptide is modified at a sidechain of one or more amino acid residue(s), the C-terminus, the N-terminus, or a combination thereof.

Statement 26. A fusion protein or proteolysis targeting chimera (PROTAC) comprising the protein or peptide according to any one of Statements 20-25.

Statement 27. A fusion protein or PROTAC according to Statement 26, further comprising an E3 ligase subunit or fragment of an E3 subunit.

Statement 28. A fusion protein or PROTAC according to Statement 27, wherein the E3 ligase is Von Hippel-Lindau tumor suppressor (VHL), cereblon (CRBN), mouse double minute 2 (MDM2), cellular inhibitor of apoptosis (cIAP), and speckle-type POZ protein (SPOP).

Statement 29. A composition comprising a protein or peptide according to any one of Statements 20-25 and a pharmaceutically acceptable carrier.

Statement 30. A composition comprising a fusion protein or PROTAC according to any one of Statements 26-28 and a pharmaceutically acceptable carrier.

Statement 31. A method for treating an individual having or suspected of having KRAS(G12V), KRAS(G12S), KRAS(G12A) and/or KRAS(G12C)-associated cancers and/or inhibiting ERK activation and/or proliferation of KRAS(G12V), KRAS(G12S), KRAS(G12A) and/or KRAS(G12C)-associated cancers comprising: administering to a subject who has been diagnosed with or is suspected of having KRAS(G12V), KRAS (G12S), KRAS(G12A) and/or KRAS(G12C)-associated cancers a therapeutically effective amount of:
i) a protein or peptide according to any one of Statements 20-25, and optionally a carrier protein; ii) an mRNA capable of encoding a protein or peptide according to any one of Statements 20-25; iii) a DNA capable of encoding a protein or peptide according to any one of Statements 20-25; iv) a microorganism that carries the gene for a protein or peptide according to any one of Statements 20-25; v) a fusion protein or PROTAC comprising a protein or peptide according to any one of Statements 20-25 (e.g., according to any one of Statements 26-28); vi) an mRNA capable of encoding a fusion protein or PROTAC comprising a protein or peptide according to claim 1; vii) a DNA capable of encoding a fusion protein or PROTAC comprising a protein or peptide according to any one of Statements 20-25 (e.g., according to any one of Statements 26-28); or viii) a microorganism that carries the gene for a fusion protein or PROTAC comprising a protein or peptide according to any one of Statements 20-25 (e.g., according to any one of Statements 26-28), wherein the subject's cancer is treated and/or the activation and/or proliferation is inhibited.

Statement 32. A method according to Statement 31, wherein the cancer is non-small cell lung cancer (NSCLC), colorectal cancer (CRC), pancreatic cancer (PDAC), uterine cancer, or gastric cancer.

Statement 33. A method according to Statement 31 or Statement 32, wherein levels of endogenous RAS mutants are reduced.

Statement 34. A protein or peptide comprising the following sequence or a truncated variant thereof, or having the following sequence or truncated variant thereof:

```
                                         (SEQ ID NO: 26)
XXXVPTXLEVVAATXXSLLISWDAPAVTVXFYVIXYGETGHGVGAFXAFX

VXXXXSTATISGLXPGVDYTITVYARXXSKQGXYXPSPISINYRT,
``` wherein each X is a canonical or non-canonical amino acid.

Statement 35. The protein or peptide according to Statement 34, wherein the sequence is:

```
                                         (SEQ ID NO: 27)
VSSVPTKLEVVAATPTSLLISWDAPAVTVXFYVIXYGETGHGVGAFXAFX

VXXSKSTATISGLKPGVDYTITVYARXXSKQGXYXPSPISINYRT or a truncated variant thereof, or (SEQ ID NO: 28)
XXXVPTXLEVVAATXXSLLISWDAPAVTVFFYVITYGETGHGVGAFQAFK

VPGXXSTATISGLXPGVDYTITVYARGYSKQGPYKPSPISINYRT, or a truncated variant thereof
```

Statement 36. The protein or peptide according to Statement 34 or Statement 35, wherein each X is individually chosen from alanine, serine, arginine, glutamine, asparagine, threonine, and tyrosine.

Statement 37. A method for treating an individual having or suspected of having KRAS(G12V), KRAS(G12S), KRAS(G12A) and/or KRAS(G12C)-associated cancers and/or inhibiting ERK activation and/or proliferation of KRAS(G12V), KRAS(G12S), KRAS(G12A) and/or KRAS(G12C)-associated cancers comprising: administering to a subject who has been diagnosed with or is suspected of having KRAS(G12V), KRAS (G12S), KRAS(G12A) and/or KRAS(G12C)-associated cancers a therapeutically effective amount of:
i) a protein or peptide according to any one of Statements 34-36, and optionally a carrier protein; ii) an mRNA capable of encoding a protein or peptide according to any one of Statements 34-36; iii) a DNA capable of encoding a protein or peptide according to any one of Statements 34-36; iv) a microorganism that carries the gene for a protein or peptide according to any one of Statements 34-36; v) a fusion protein or PROTAC comprising a protein or peptide according to any one of Statements 34-36; vi) an mRNA capable of encoding a fusion protein or PROTAC comprising a protein or peptide according to any one of Statements 34-36; vii) a DNA capable of encoding a fusion protein or PROTAC comprising a protein or peptide according to any one of Statements 34-36; or viii) a microorganism that carries the gene for a fusion protein or PROTAC comprising a protein or peptide according to any one of Statements 34-36, wherein the subject's cancer is treated and/or the activation and/or proliferation is inhibited.

The following example is presented to illustrate the present disclosure. It is not intended to be limiting in any matter.

EXAMPLE

This example provides a description of a peptide of the present disclosure.

Presented herein is a monobody, termed 12VC1, that selectively recognizes the active state of KRAS(G12V) and KRAS(G12C). This monobody bound noncovalently to these KRAS mutants by up to 400-fold more tightly than to wild type KRAS, exhibiting a high level of selectivity. The crystal structure of an HRAS-12VC1 complex revealed that 12VC1 presents a shallow pocket that selectively recognized the mutations and it targets the Switch I and II regions of RAS, thereby directly inhibiting RAS-effector interactions. When expressed intracellularly, 12VC1 potently inhibited ERK activation and the proliferation of KRAS(G12V)- and KRAS(G12C)-driven cancer cell lines in vitro and in a mouse xenograft model. The selectivity of 12VC1 was used for selective degradation of endogenous RAS mutants, resulting in more sustained signaling inhibition than direct inhibition. This shows selective and non-covalent inhibition and degradation of the active state of oncogenic KRAS mutants is achievable and potentially therapeutically effective.

Figure 5:
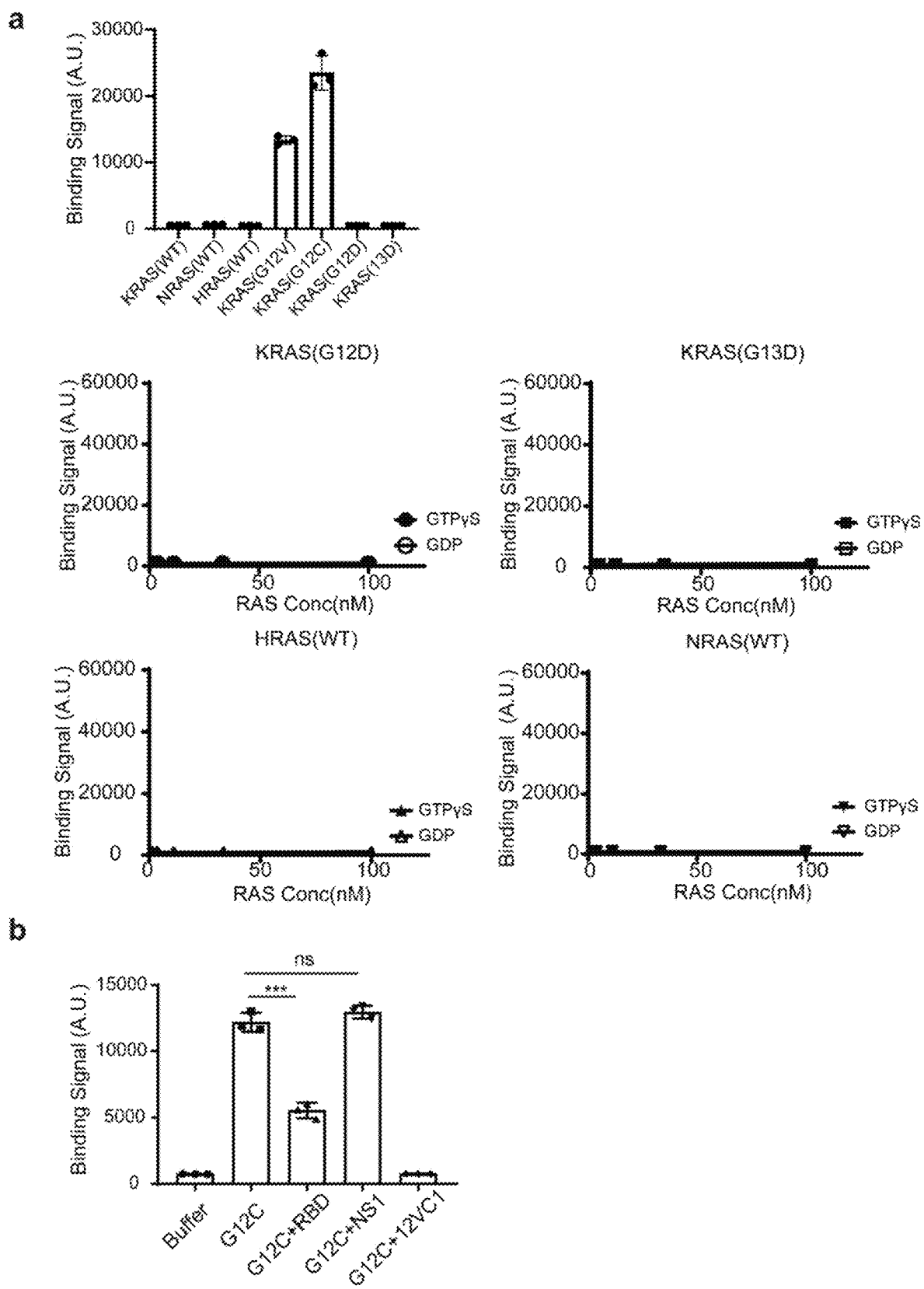
FIG. 5. Binding of 12VC1 to RAS mutants and isoforms in the yeast display format. a, Binding measurements of 12VC1 to 50 nM of wild-type RAS isoforms and mutants (n=3) (top). Titration of KRAS(G12D), KRAS(G13D), HRAS(WT) and NRAS(WT) in GTPγS and GDP bound nucleotide states showed no binding. b, Competitive binding assay of 12VC1 against known interaction partners of RAS. KRAS(G12C) (20 nM) was preincubated with excess concentrations (3.875 µM) of purified RAF1-RBD, monobody NS1 or monobody 12VC1, and then their binding to 12VC1 displayed on the yeast surface was measured. Median fluorescence intensity (MFI) and standard deviation are plotted (n=3). KRAS(G12C) preincubated with RAF1-RBD showed significant decrease in binding signal, which suggested that it competed with 12VC1 for binding (n=3, one-way ANOVA, p<0.001). No significant decrease in binding signal was observed when RAS was preincubated with NS1 which binds to the α4-β6-α5 interface away from the switch regions (technical replicates, n=3, one-way ANOVA, p=0.21).

Monobody technology, a synthetic binding protein platform that has produced potent and selective binders to diverse protein targets, was employed. The developed monobody, termed 12VC1, demonstrated exceptionally high selectivity for KRAS(G12V) and KRAS(G12C) (FIG. 1a). Affinity measurements in the yeast display format revealed that 12VC1 bound selectively to the GTPγS-bound form, over the GDP-bound form, of KRAS mutants. Importantly, it did not detectably bind to wild-type K, N, or HRAS in either nucleotide-bound form (FIG. 5a). Furthermore, 12VC1 competed with RAS-binding domain of RAF-1 (RAF1-RBD) for binding to RAS (FIG. 5b). Bio-layer Interferometry (BLI) using purified 12VC1 (FIG. 1b, Table 1) further demonstrated the high selectivity of 12VC1, with up to a 400-fold difference in affinity, to mutants with a small side chain (Affinity; G12C>G12V>>G12A and G12S) over wild type. These mutations collectively account for a large fraction of the KRAS mutations found in cancers with poor five-year survival rates including non-small cell lung cancer (NSCLC), colorectal cancer (CRC) and pancreatic cancer (PDAC).

Figure 6:
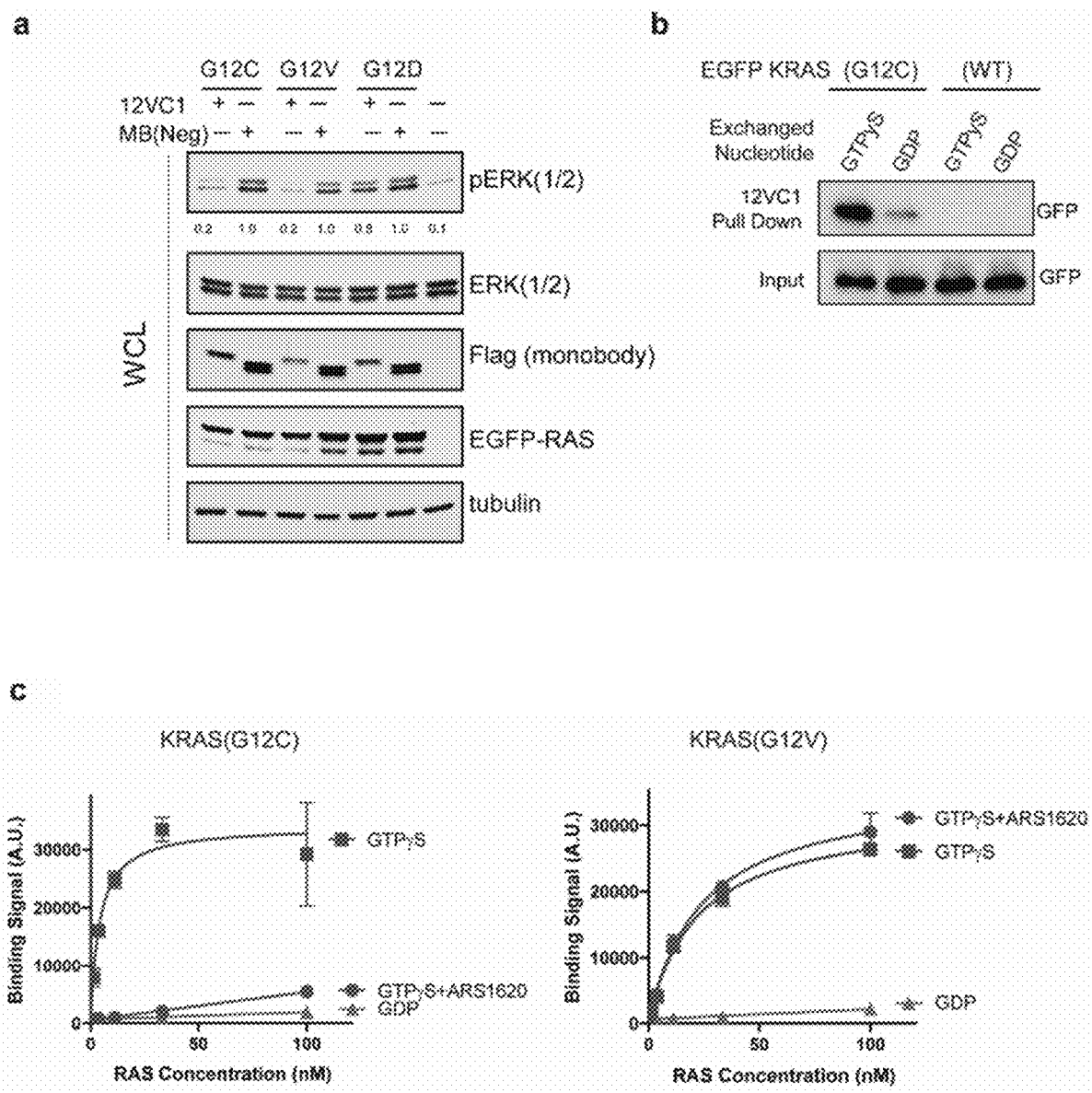
FIG. 6. 12VC1 is selective to KRAS mutants. a, ERK activation in HEK293T cells co-expressing monobody and RAS mutants. HEK293T cells were transiently co-transfected with plasmids encoding EGFP fused to full length KRAS mutants and mCherry fused to flag-tagged monobodies. Whole cell lysates (WCL) were probed for level of phospho-ERK (pERK), total ERK (ERK1/2), EGFP-RAS and monobodies (Flag). MB(Neg) is a non-binding monobody control. Representative data from n=3 are shown. b, Nucleotide and mutant specificity of 12VC1 tested in a pull-down assay. HEK293T cells were transiently transfected with plasmid encoding EGFP-KRAS(G12C) or EGFP-KRAS(WT) and lysed after allowing protein expression overnight. Lysates (500 µg) were subjected to nucleotide exchange by adding EDTA and excess specified nucleotide. Biotinylated 12VC1 bound to M280 magnetic beads was used to pull down RAS from the lysates. Bound proteins released from beads and the inputs were visualized by immunoblotting with an anti-GFP antibody to determine the abundance of captured EGFP-KRAS. c, Binding of 12VC1 to purified KRAS(G12C) and (G12V) with and without covalent inhibitor ARS1620 tested in the yeast display format. ARS1620 was added to purified KRAS(G12C) and (G12V) during the nucleotide exchange reaction. Binding titration of 12VC1 displayed on yeast was performed. Note that reaction with ARS1620 abolished the binding of 12VC1 to KRAS(G12C) but not to KRAS(G12V).
Figure 7:
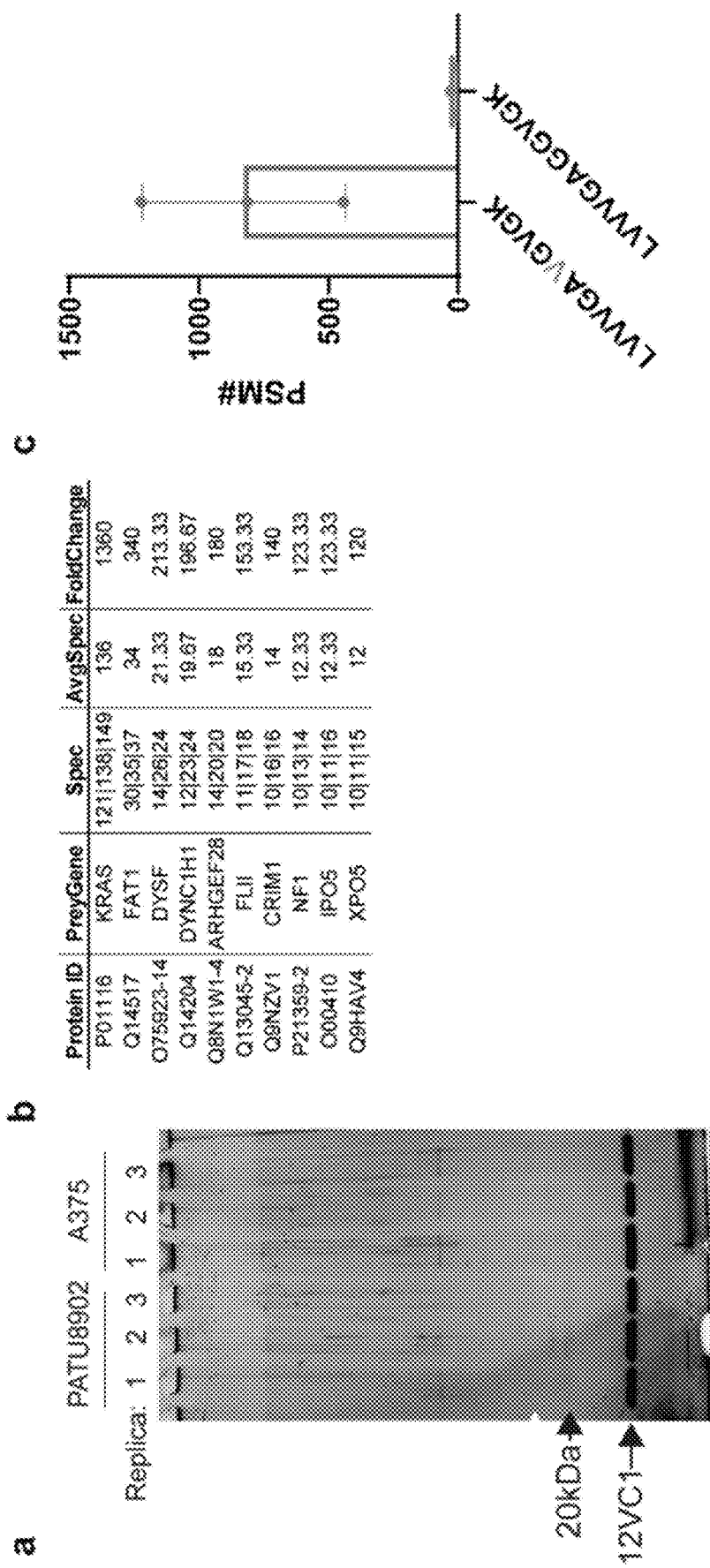
FIG. 7. Assessment of the selectivity of 12VC1 to endogenous RAS mutants by proteomics analysis. RAS pull-down experiments were performed with lysates of PATU8902 that contained endogenous KRAS(G12V) and lysates of A375 cells that contained RAS(WT) using 12VC1 as a bait. a, SDS-PAGE of affinity-purified samples stained with the Krypton staining reagent. b, List of proteins that were unique in the lysate of PATU8902 as identified using LC/MS/MS based proteomics (n=3). The identities and spectral counts of the top 10 most abundant proteins that were uniquely captured from the lysate of PATU8902 are listed. Fold change is defined as the ratio of spectral counts recorded from PATU8902 lysate over the spectral counts recorded from the control (A375) lysate for the listed protein. c, Spectral counts of a KRAS(G12V)-specific peptide, LVVVGAVGVGK (SEQ ID NO:21), and that of the counterpart specific to wild-type RAS, LVVVGAGGVGK (SEQ ID NO:22), in pull-down samples of PATU8902, demonstrating that the captured RAS is overwhelmingly KRAS(G12V).

KRAS(G12C), respectively, but not from growth factor stimulated HEK293T cells containing only wild-type RAS (FIG. 1d). Furthermore, treatment of H358 cells with ARS1620, a covalent inhibitor that traps KRAS(G12C) in the GDP-bound state abrogated detectable binding of RAS to 12VC1 (FIG. 1d, FIG. 6c). Proteomics analysis showed that 12VC1 selectively captured endogenous KRAS(G12V) from PATU8902 cell lysates over wild-type RAS (FIG. 1e, FIG. 7a, b, c). These results showed desirable selectivity of 12VC1 to both G12V and G12C mutants and its ability to directly inhibit RAS-mediated signaling.

Figure 2:
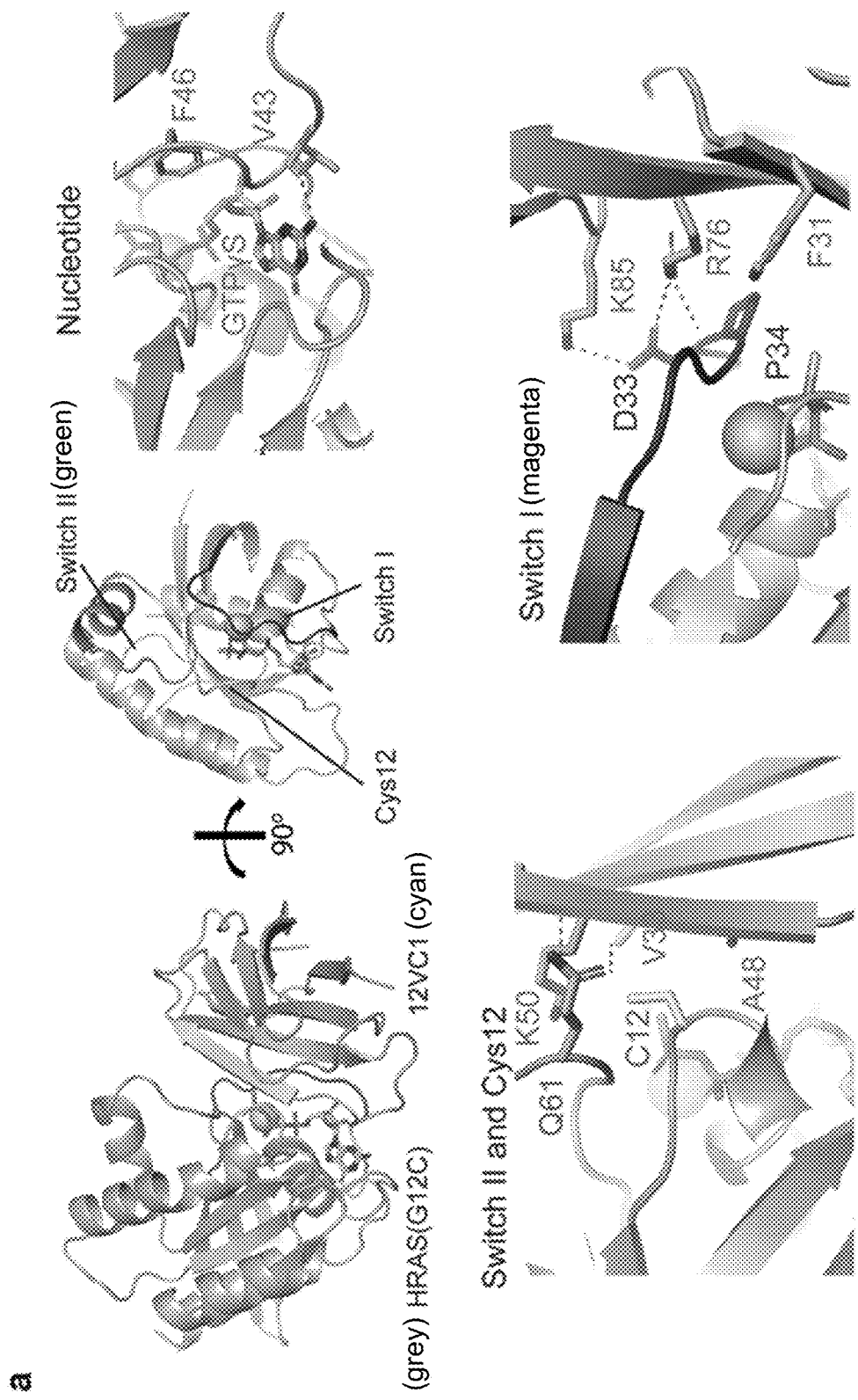
FIG. 2. Structural basis for mutant-selective recognition of RAS by 12VC1 monobody. a, Crystal structure of 12VC1 (cyan) bound to HRAS(G12C) (grey). Critical interactions between 12VC1 and HRAS G12C occur at the switch I (magenta) and switch II (green) regions. Interactions at these regions are expanded for detailed views in separate panels. Residue V43 of 12VC1 forms a hydrogen bound with the nucleotide. Mutated position, Cys12 of RAS, is accommodated by a pocket that consists of residues V33, A48, and K50 of 12VC1. Residues R76 and K85 on 12VC1 form hydrogen bond and salt bridges with Switch I residue D33. Residue F31 on 12VC1 forms hydrophobic interactions with Switch I. b, An open book view of the HRAS(G12C):12VC1 complex. Effects of alanine mutation of 12VC1 residues located within 4 Å of HRAS are shown in the bar graph. Asterisks denotes that $\Delta\Delta G$ is beyond the measurable limit of experiments and thus the values shown represent the lower limit. The error bars indicate s.d., n=3, technical replicates. The mutated residues in alanine scanning are shown as spheres in the cartoon model, and those for critical residues ($\Delta\Delta G > 2$ kcal/mol) are labeled (middle panel).
Figure 2:
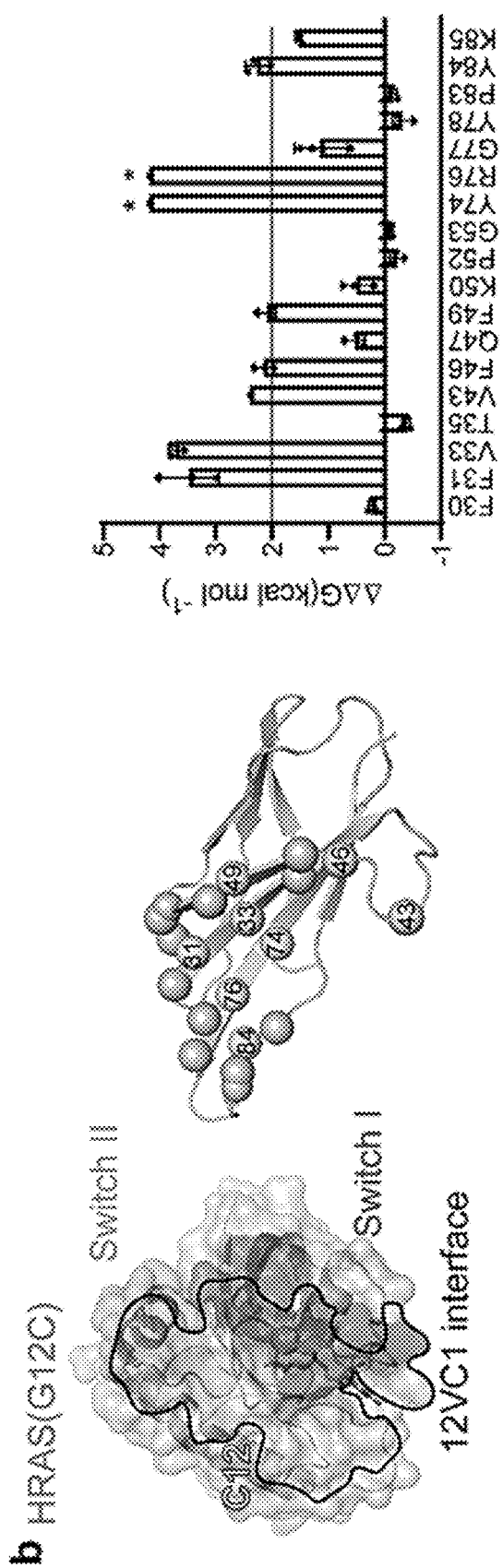
Figure 8:
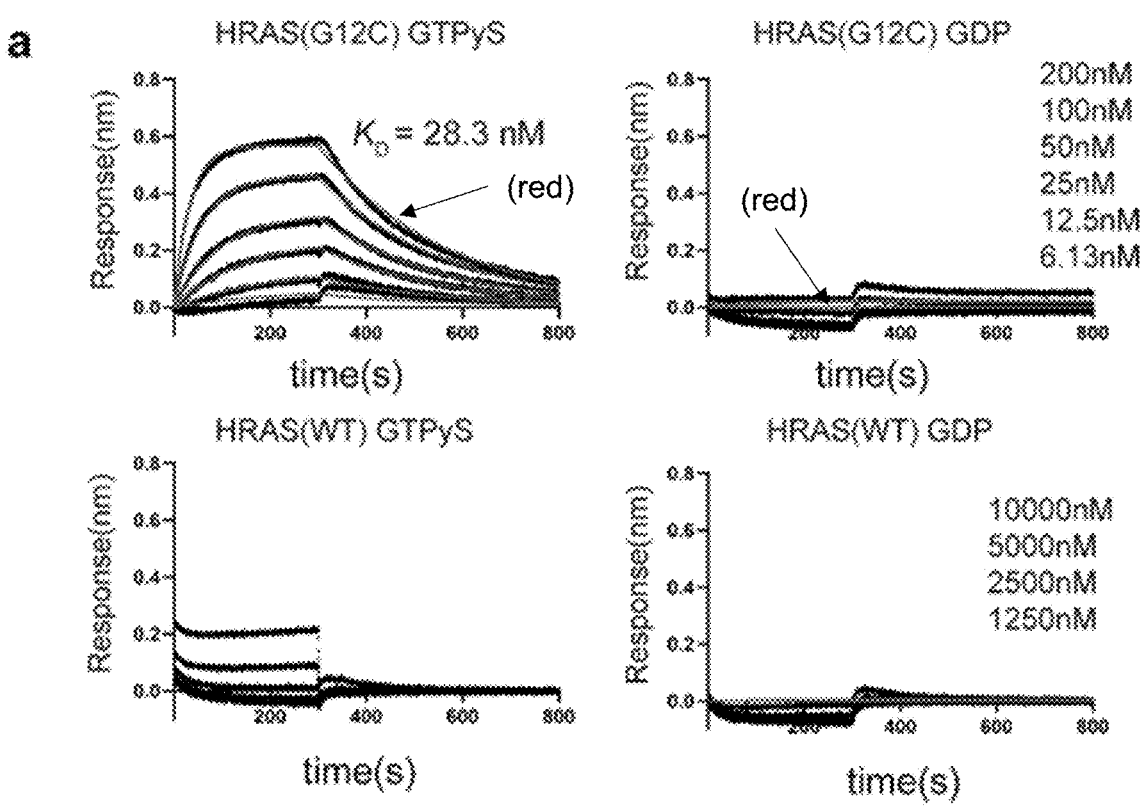
FIG. 8. Crystal structure of HRAS(G12C) bound to 12VC1. a, Selectivity and affinity of 12VC1 to HRAS constructs used in crystallization. BLI binding kinetic measurements of 12VC1 against HRAS(G12C) 1-166 and HRAS(WT) 1-166 in GTPγS and GDP bound state. BLI data was fitted globally (red). The $K_D$ values of 12VC1 against HRAS(G12C) were 28.3 and 35.9 nM when measured in duplicate. The $K_D$ values against GDP-bound HRAS(G12C) and HRAS(WT) were too high to be determined from the collected data. b, Overlay of HRAS bound to 12VC1 and RAF1-RBD (PDB: 4g0n). 12VC1 and RAF1-RBD both binds to Switch I region (purple) on RAS. The binding epitope of 12VC1 (black outline) overlaps with the binding epitope of RAF1-RBD (red). c, Analysis of interacting residues between HRAS(G12C) and 12VC1. The crystal structure of 12VC1 in cartoon representation and HRAS (G12C) in surface representation (top). Residues of HRAS (G12C) that are within 4 Å of 12VC1 are highlighted in the sequence. Residue C12 of HRAS(G12C) is highlighted in red. 12VC1 interacted with numerous residues in the Switch I and II regions (bold). On the monobody side (right panel), the residues that interact with RAS are located in multiple strands and loops. Presented is SEQ ID NO:23 (MTEYKLVVVGACGVGKSALTIQLIQNHFVDEYDP-TIED SYRKQVVIDGETCLLDILDTAGQEEYSAMRD-QYMRTGEGFLCVFAINNTKSFEDIHQ YREQIKRVK-DSDDVPMVLVGNKCDLAARTVESRQAQDLARSY-GIPYIETSAKTRQG VEDAFYTLVREIRQH).
Figure 8:
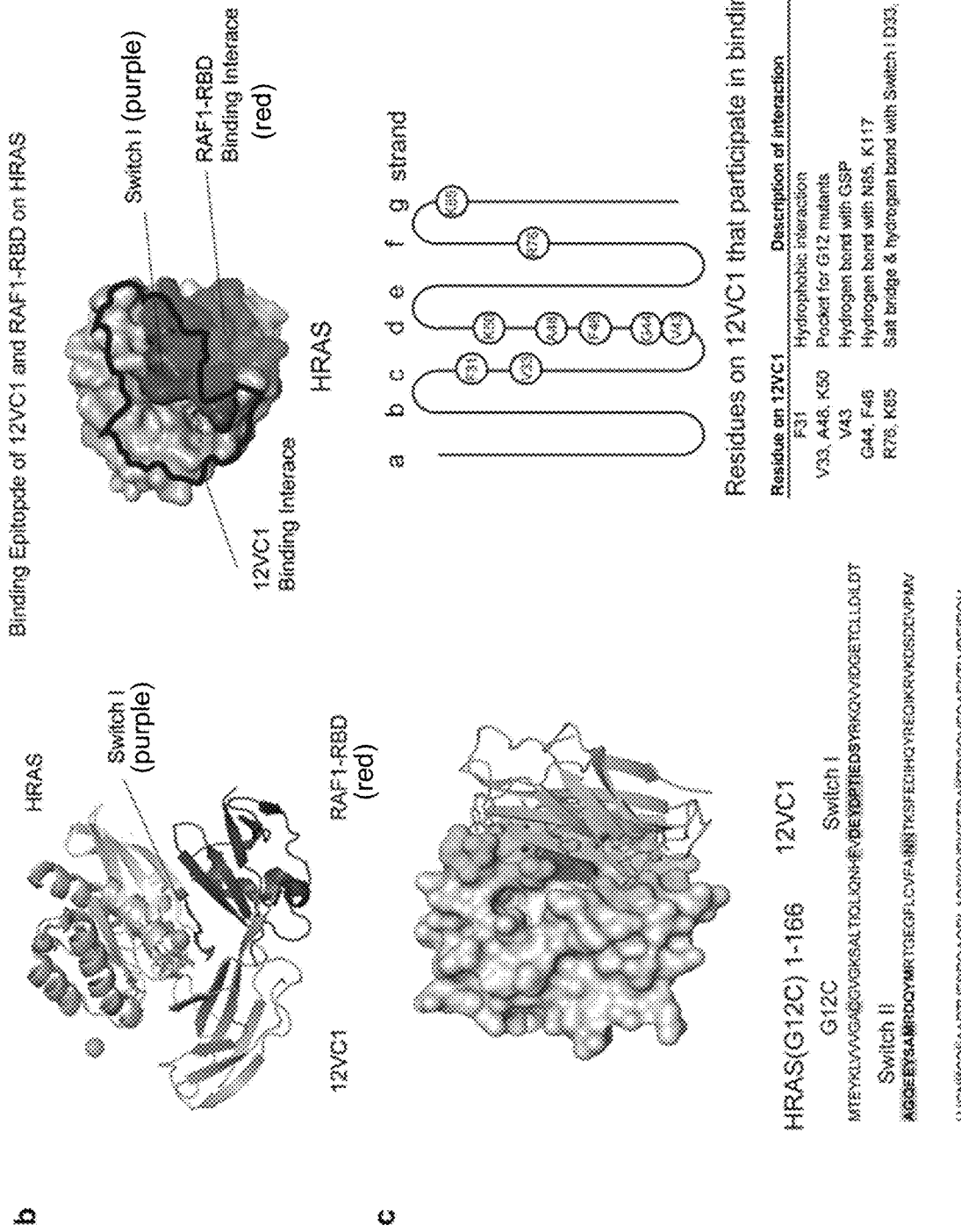

The crystal structure of 12VC1 bound to HRAS(G12C) with GTPγS (Table 2) was determined. We used HRAS because it crystallizes more readily than KRAS. The binding interface of this structure should be relevant to how 12VC1 recognizes KRAS mutants, because HRAS and KRAS have the identical amino acid sequence in the effector lobe to which 12VC1 binds, and the binding data confirmed that 12VC1 maintained selectivity toward the G12C mutation in HRAS (FIG. 8a). The crystal structure revealed that 12VC1 bound to RAS through both Switch I and II regions, as well as through the bound nucleotide, occupying 853 Å$^2$ of the surface of RAS (FIG. 2a). A comparison of the epitopes between HRAS bound to 12VC1 and RAF1-RBD showed an overlap at the Switch I region (FIG. 8b), which further confirmed that 12VC1 is a direct competitor of RAF1-RBD. The selectivity of 12VC1 to the active, GTP-bound form of RAS is likely due to the interactions of several residues of

TABLE 1

Kinetic and equilibrium parameters for 12VC1 binding determined from BLI measurements

| Target | Nucleotide State | $K_D$ (nM) | S.D. | $k_{on}$ (M s$^{-1}$) | S.D. | $k_{off}$ (s$^{-1}$) | S.D. |
|---|---|---|---|---|---|---|---|
| KRAS(G12C) | GTPγS | 24.7 | 1.0 | 1.1E+05 | 2.2E+04 | 2.7E−03 | 5.3E−04 |
| KRAS(G12V) | GTPγS | 101.1 | 38.7 | 7.2E+04 | 8.3E+03 | 7.0E−03 | 1.9E−03 |
| KRAS(G12A) | GTPγS | 718.1 | 98.7 | NA | NA | NA | NA |
| KRAS(G12S) | GTPγS | 686.1 | 56.7 | NA | NA | NA | NA |
| KRAS(WT) | GTPγS | 9600 | 800 | NA | NA | NA | NA |
| KRAS(G12C) | GDP | ND | ND | ND | ND | ND | ND |
| KRAS(G12V) | GDP | ND | ND | ND | ND | ND | ND |
| KRAS(G12A) | GDP | ND | ND | ND | ND | ND | ND |
| KRAS(G12S) | GDP | ND | ND | ND | ND | ND | ND |
| KRAS(WT) | GDP | ND | ND | ND | ND | ND | ND |

NA, parameter not available, because data were analyzed in the equilibrium mode.
ND, parameter not determined, because binding signals were too low for curve fitting.

12VC1 selectively engaged KRAS mutants and potently inhibited RAS-mediated signaling, when expressed intracellularly as a genetically encoded reagent (FIG. 1c; FIG. 6a). "Pull-down" assays further confirmed its selectivity towards the GTP-bound state of RAS mutants (FIG. 6b). 12VC1 selectively captured endogenous KRAS from cancer cell lines PATU8902 and H358 that contain KRAS(G12V) and 12VC1 with residues of Switch I (FIG. 2a). Cys12 is the only residue in the P-loop that is in direct contact (within 4 Å) with 12VC1. Alanine scanning analysis of 12VC1 revealed numerous binding hot-spot residues distributed across the expansive binding interface including those located in beta-strands and two loops (FIG. 2b, FIG. 8c).

TABLE 2

Data collection and refinement statistics.

| | HRAS(G12C)/12VC1 (7L0G)$^a$ | HRAS(WT)/12VC3 (7L0F)$^a$ |
|---|---|---|
| | Data Collection | |
| Space group | P1 21 1 | P1 21 1 |
| Cell Dimensions | | |
| a, b, c (Å) | 71.83, 62.60, 123.40 | 73.01, 64.82, 127.12 |
| α, β, γ (°) | 90, 101.22, 90 | 90, 102.37, 90 |

TABLE 2-continued

Data collection and refinement statistics.

| | HRAS(G12C)/12VC1 (7L0G)[a] | HRAS(WT)/12VC3 (7L0F)[a] |
|---|---|---|
| Resolution (Å) | 50.00-2.54 (2.58-2.54)* | 50.00-1.98 (2.01-1.98)* |
| $R_{merge}$ | 0.152 (0.501) | 0.115 (0.767) |
| I/σI | 8.62 (3.21) | 14.35 (2.78) |
| Completeness(%) | 98.9 (99.9) | 96.0 (95.3) |
| Redundancy | 4.9 (5.2) | 5.0 (4.9) |
| Refinement | | |
| Resolution (Å) | 41.87-2.54 | 44.84-1.98 |
| No. reflections | 35,157 | 77,312 |
| $R_{work}/R_{free}$ | 0.199/0.228 | 0.159/0.191 |
| No. atoms | | |
| Protein | 8084 | 8102 |
| Ligand/ion | 132 | 132 |
| Water | 53 | 641 |
| B-factors | | |
| Protein | 55.38 | 35.55 |
| Ligand/ion | 41.63 | 23.98 |
| Water | 40.01 | 39.13 |
| R.m.s deviations | | |
| Bond lengths (Å) | 0.01 | 0.02 |
| Bond angles (°) | 1.27 | 1.85 |
| Interface analysis | | |
| Interface area (Å$^2$)[c] | | |
| HRAS-monobody | 853 | 861 |
| Monobody-HRAS | 794 | 829 |

*Highest-resolution shell is shown in parentheses.

Figure 9:
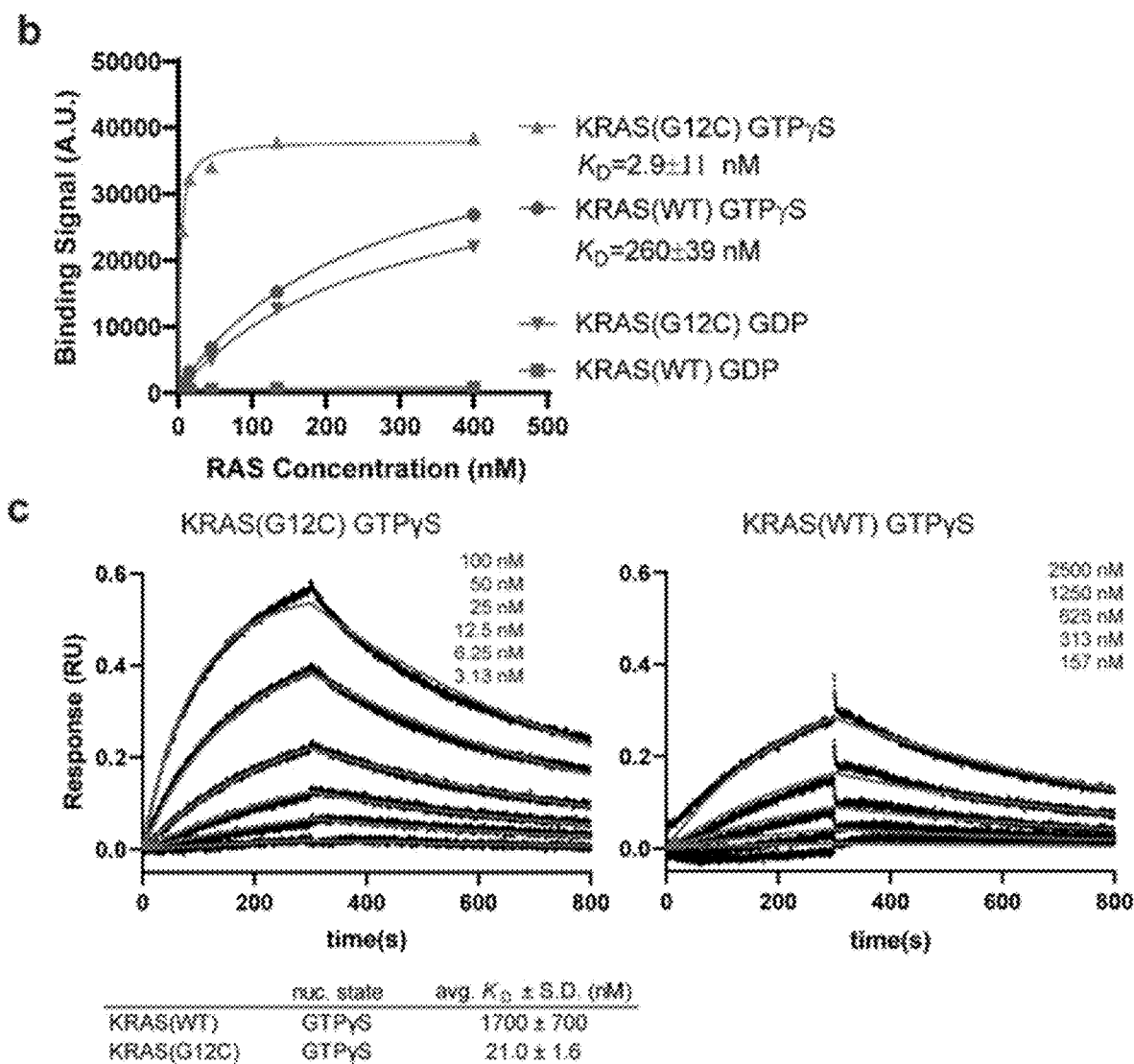
FIG. 9. A surface pocket on 12VC1 provides selectivity to mutant. a, pocket analysis of RAS-monobody complex. We detected a series of hot-spot binding pockets in the concave surface of monobody 12VC1 using AlphaSpace. The top-scored pocket, which is occupied by Cys12 of RAS, is highlighted. Lower panel: Results of molecular dynamics simulations (MD) of monobody complexed with different RAS mutants. MD revealed that RAS(G12C) and RAS (G12V) formed stable complex with 12VC1, whereas 12VC1 complexes with wild type, G12D, G13D and Q61L mutants were unstable, which are consistent with experimental results. b, 12VC3, a mutant of 12VC1 that binds to RAS(WT). Yeast display binding titration of 12VC3 against KRAS(WT) and KRAS(G12C) in GTPγS and GDP bound states. The uncertainties shown represents errors from non-linear least-squares fitting of a 1:1 binding model. c, BLI sensorgrams of 12VC3 bound to KRAS(G12C) and KRAS (WT). The $K_D$ values are 21.0±1.6 nM for G12C and 1776.7±747.7 nM for WT (n=3). Errors represent the standard deviation.
Figure 10:
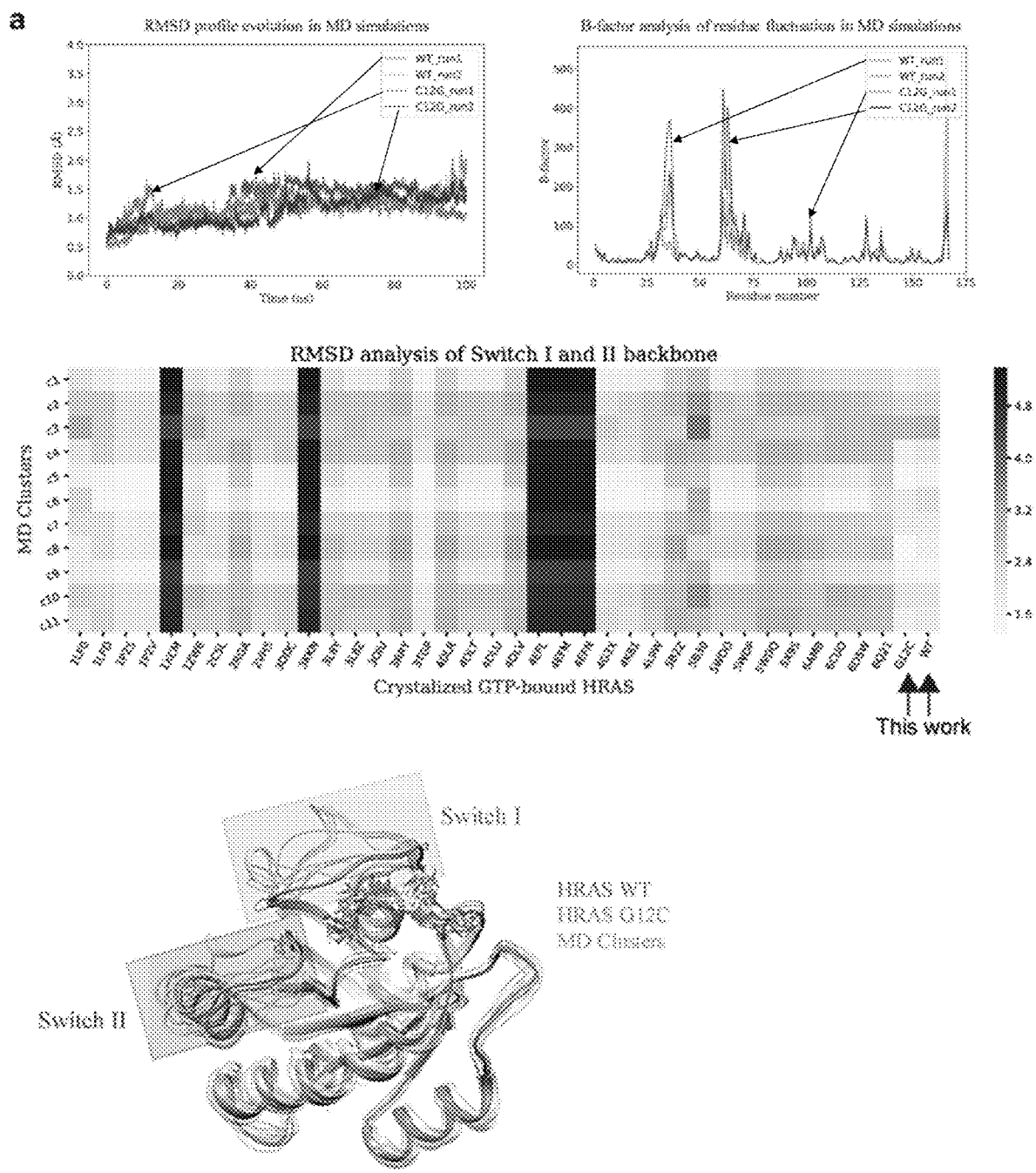
FIG. 10. Analysis of crystal structures of 12VC1 HRAS (G12C) and 12VC3 HRAS(WT). a, To validate the conformations captured by 12VC1 and 12VC3 monobodies, the crystal structures of HRAS(G12C) and HRAS(WT) were relaxed in a MD simulation after removing the bound monobodies in the models. The RMSD analysis of HRAS (G12C) and (WT) showed that these two HRAS conformations were relatively stable and no drastic structural changes were observed in MD simulations (top left panel). The most dynamic regions in these two RAS structures were Switch I and Switch II (top right panel). Classification of MD trajectories based on similarity of the switch I and II conformations to crystal structures of RAS bound to GTP analogue. The HRAS(G12C) and (WT) structures captured by monobodies 12VC1 and 12VC3, respectively, belonged to the same "MD cluster", which suggest that the captured HRAS structures have energetically similar conformation (bottom panel). b, Crystal structures of 12VC1-bound HRAS(G12C) and 12VC3-bound HRAS(WT) were aligned in ribbon representation, showing that they have nearly identical backbone conformations. Side chains of residues in the Switch II region of HRAS(G12C) (magenta) and HRAS (WT) (teal) showing that Q61, E62, and E63 are in vastly different orientation in the two structures. c, Comparing the orientation of Q61 in 12VC3 and 12VC1 bound HRAS(WT) and (G12C) respectively with other crystal structures of HRAS. 12VC3 bound to a state where Q61 is pointed towards the interior of RAS. This side chain conformation is found in the structures of GTP-bound RAS in the state 1 conformation. Q61 in 12VC1 bound HRAS(G12C) is found in the state 2 conformation. State 1 and 2 are both observed in HRAS(WT) structures, therefore the free energy difference for the transition between these two states is probably small and is not likely to be a major contributor of mutant selectivity.
Figure 10:
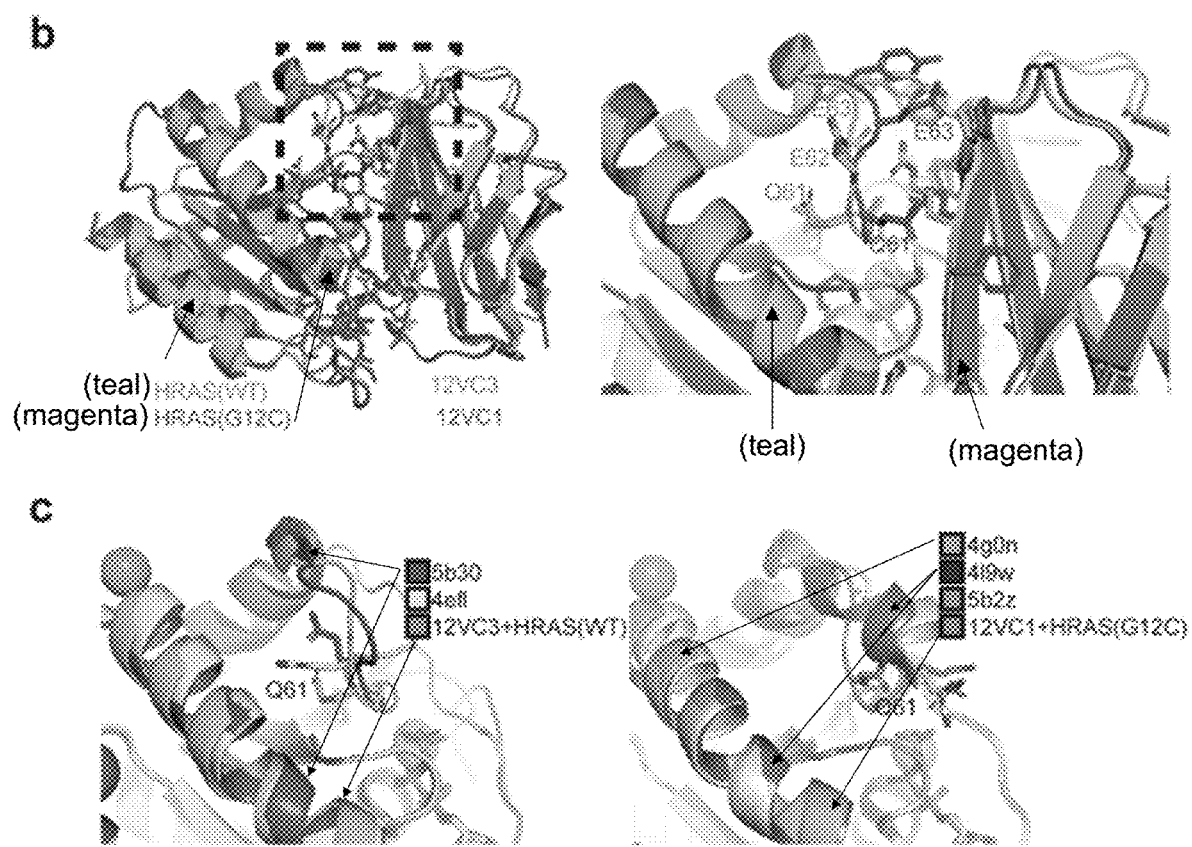

The structure and the interface energetics suggested two possible mechanisms for the high selectivity of 12VC1: first, the monobody directly discriminates the mutated residue at position 12, and second it recognizes a conformation of the epitope that is unique to RAS mutants. To examine the first possibility, computational structural analysis was utilized, which revealed a shallow pocket, comprising residues V33, A48 and K50, that accommodates the Cys12 side chain (FIG. 2a, FIG. 9a). This observation suggested that this pocket directly recognizes small and uncharged side chains at residue 12; by contrast an unfilled pocked, which would occur with wild-type Gly, is energetically unfavorable. Bulky and charged side chain such as that of G12D would be too large to fit into the pocket, thus destabilize the complex. The selectivity of 12VC1 to G12V, G12C, G12A and G12S (FIG. 1b, Table 1) supports this view. A direct comparison to the structure of 12VC1 bound to HRAS(WT) would allow the ability to conclusively differentiate the two possibilities, however, crystals of 12VC1-HRAS(WT) complex were not obtained, probably due to a low affinity interaction. Thus, the affinity of 12VC1 to the wild type was improved by mutating the residues that formed the pocket that "sensed" G12C (V33, A48 and K50) and by incorporating the T35A mutation that improved the overall affinity to RAS (FIG. 2b). The resulting clone, termed 12VC3, had improved affinity to wild-type RAS (FIG. 9b,c) and enabled the determination of the crystal structure of its complex with HRAS(WT). Overlay of the two structures and molecular dynamics (MD) simulations revealed that there are no significant differences in the backbone conformation between HRAS(WT) and HRAS(G12C) captured by the respective monobodies. (FIG. 10a, b, c). Differences were restricted to the orientations of a few side chains in Switch II, an inherently flexible region. Similar degrees of differences in side chain orientations were also observed in other crystal structures of HRAS(WT), thus eliminating side chain orientation as a main contributor of exceptional selectivity for the mutant (FIG. 10c). Taken together, these findings demonstrated that RAS mutations at position 12 can be selectively recognized in a non-covalent manner by a small pocket within a binding protein and potentially other types of molecules.

Figure 3:
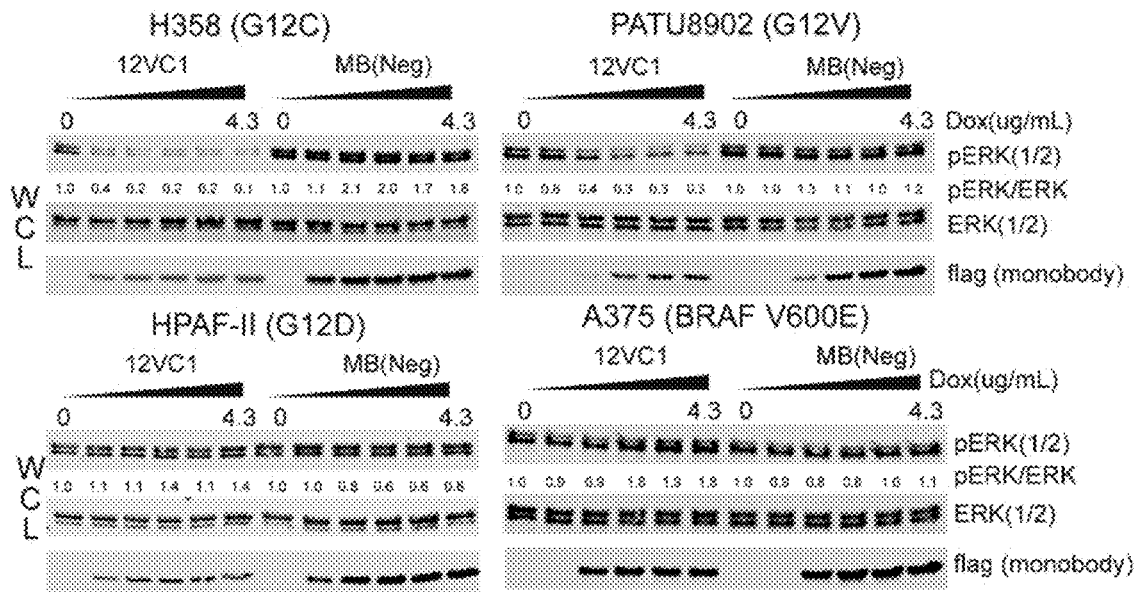
FIG. 3. Inhibition by intracellularly expressed 12VC1 monobody of signaling and proliferation of RAS mutant-driven cancer cells. a, Effects of 12VC1 expression on ERK activation (24 hrs. induction with 4.3 µg/mL dox in quarter decrements). The numbers under the pERK panel indicate the ratio of pERK signal to the total ERK signal normalized to the no dox sample. b, Percent-change of monobody expressing population after 72 hours of dox induction relative to 24 hours of induction. A negative percentage signifies a decrease in population. The p values for the differences between 12VC1 and MB(Neg) expression, as determined with t-test for H358, H23, PATU8902, H441, HPAF-II, A375, and HEK293T are 0.002, <0.001, <0.001, <0.001, 0.9, 0.006, and 0.55 respectively. Error bars represent s.d.; biological replicates, n=4 for H358 and HEK293T and n=3 for the other cell lines. c, The effects of monobody expression on tumor growth in a mouse xenograft model. Tumors were developed from subcutaneously injected PATU8902 cells that express 12VC1 or MB(Neg) under a dox-inducible promotor. Monobody expression was induced on the day indicated with the black arrow. Plots show the effect on average tumor sizes over time (n=5, biological replicates, mean±s.e.). Extracted tumor weights at the end of the experiment are also shown (n=5, biological replicates, mean±s.e.), average tumor sizes were compared using t-test, p-value=0.03, 0.71, respectively for 12VC1 and MB(Neg) tumors with and without doxycycline. d, Lysates from each tumor (#1-5) at the end of the experiment were compared with pre-injected cells (P) by immunoblotting for monobody expression and ERK activation.
Figure 3:
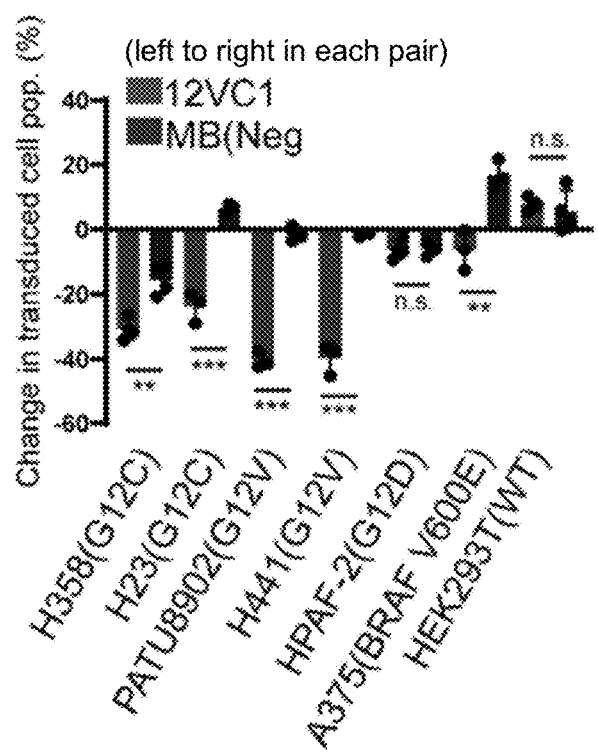
Figure 3:
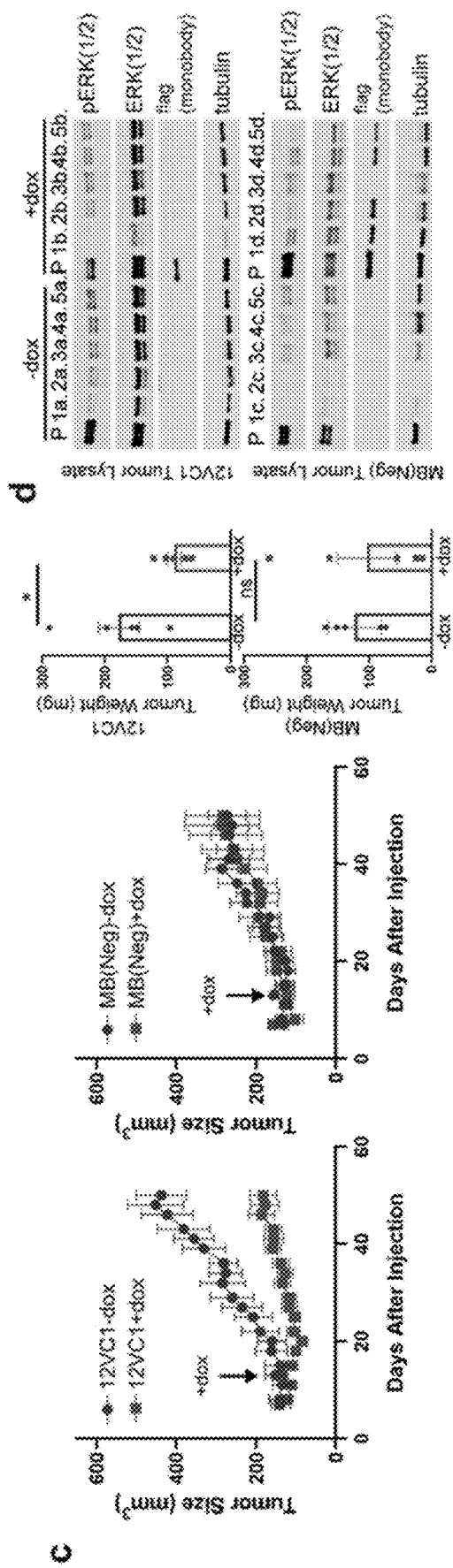
Figure 11:
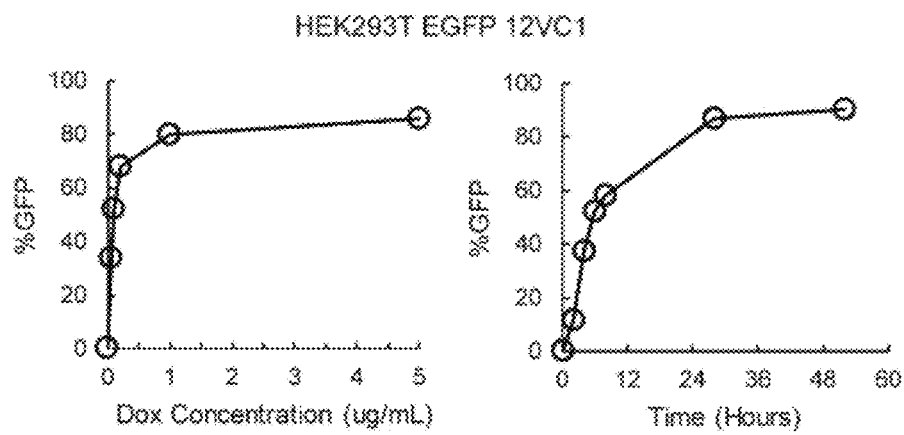
FIG. 11. Generation of a panel of dox-inducible monobody-expressing cell lines. a, A table of cell lines used for generating dox-inducible stable cell lines. b, Percentage of HEK293T cells expressing EGFP fused 12VC1 as a function of doxycycline concentration and time. In the presence of 1 μg/mL of doxycycline, 48 hours is enough to reach the maximal induction of monobody. c, Inducibility of a panel of dox-inducible FP-flag-monobody expressing cell lines generated from parental cell lines listed in Extended Data Table 2. In some cell lines mVenus were used instead of EGFP to reduce the toxicity associated with high expression levels of EGFP. Both mVenus and EGFP were detected through GFP channel on the flow cytometer. Without doxycycline in the media there was very low basal expression of the monobodies (blue). After 48 hours of induction with 1 μg/mL of doxycycline, greater than 75% of the cell population became GFP positive (red) for all cell lines.
Figure 11:
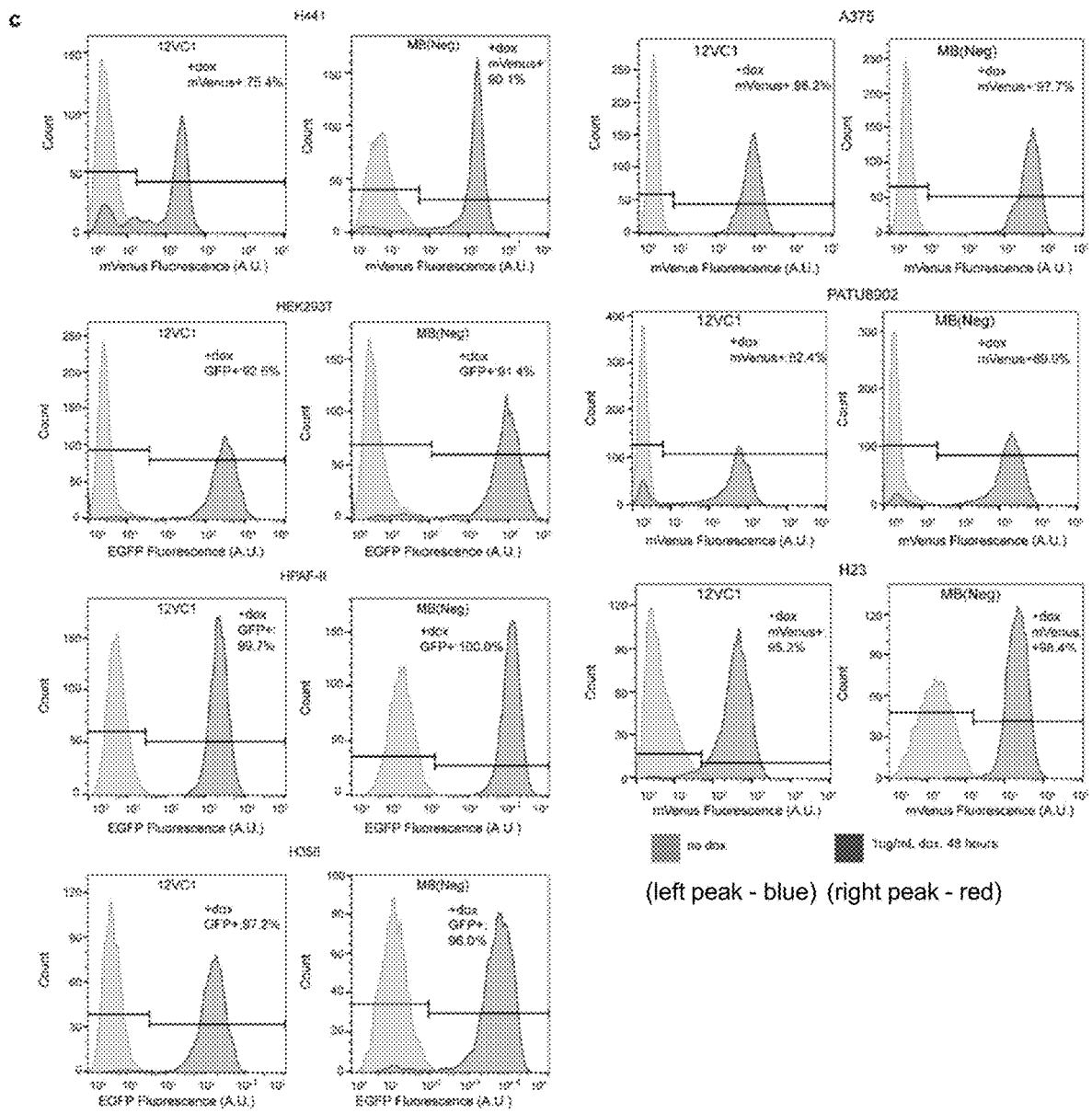
Figure 12:
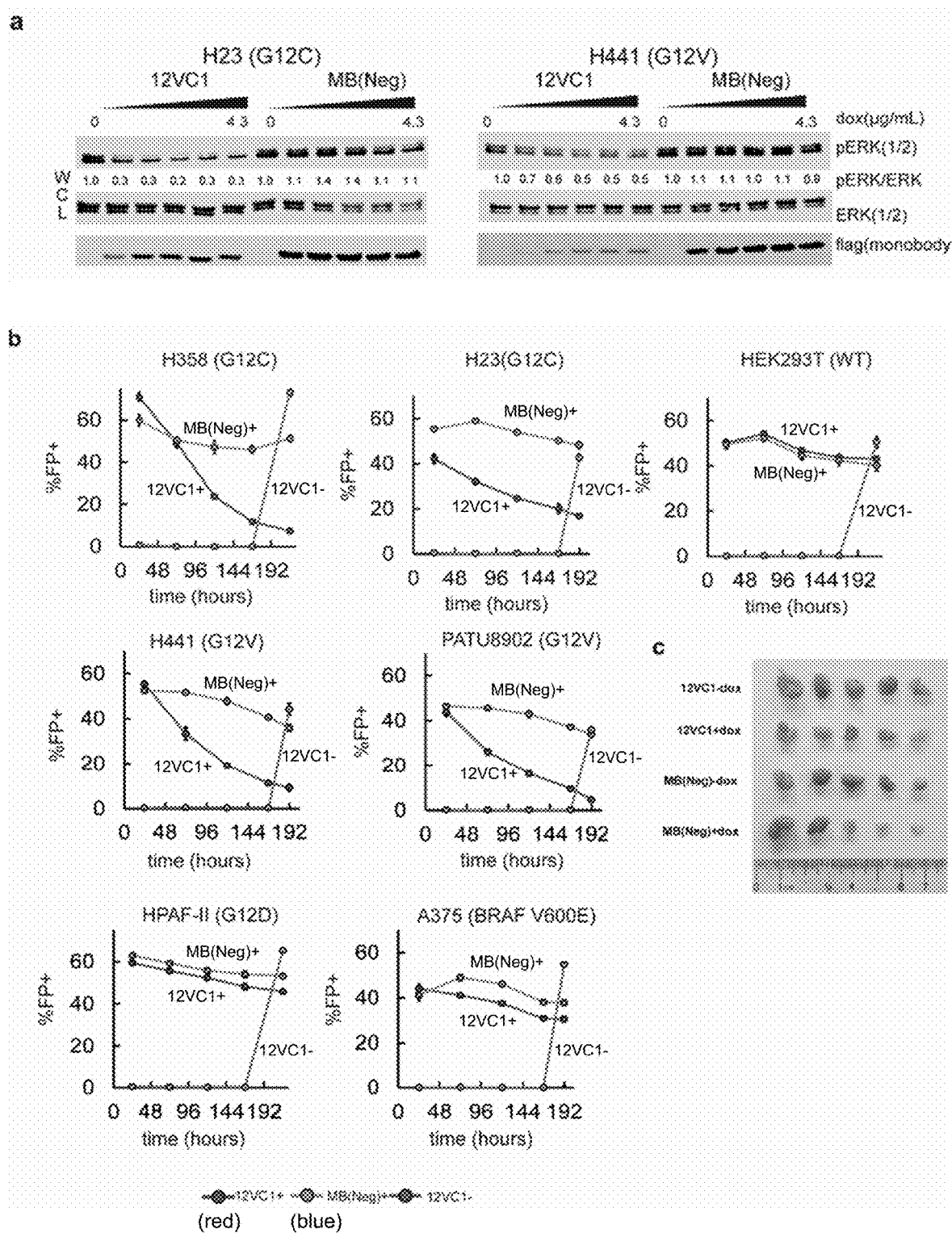
FIG. 12. Effects of 12VC1 expression on mutant RAS-driven cancer cells and solid tumor. a, Effects of monobody on ERK activation in additional cancer cell lines. b, Effects of 12VC1 expression on proliferation. Dox-inducible cell lines expressing fluorescent protein-fused 12VC1 (red) or a nonbinding control monobody, MB(Neg), (blue) were mixed with respective parental cells at an approximately 1:1 ratio. The fluorescence positive (FP+) cell populations were monitored over time in the presence of 1 μg/mL dox for the duration of entire experimental period (red and blue) or just 24 hours before the last time point (gray), a control that eliminates the possibility of growth inhibition due to viral transduction. Growth inhibition results in a reduction of the FP population. Error bars represents s.d. (n=3). For most data points, error bars are within the size of the symbols. c, Tumors extracted from PATU8902 xenografts at the end of the experiment. Tumors were much smaller across the board for 12VC1+dox compared with 12VC1-dox. Tumors are ranked from largest to the smallest. Dox appeared to have minimal effect on tumor growth in for a majority of the PATU8902 tumors expressing MB(Neg). Expression of the monobody MB(Neg) was not detected in the smallest tumor of the MB(Neg)+dox group, indicating that the tumor failed to engraft in this particular mouse.
Figure 13:
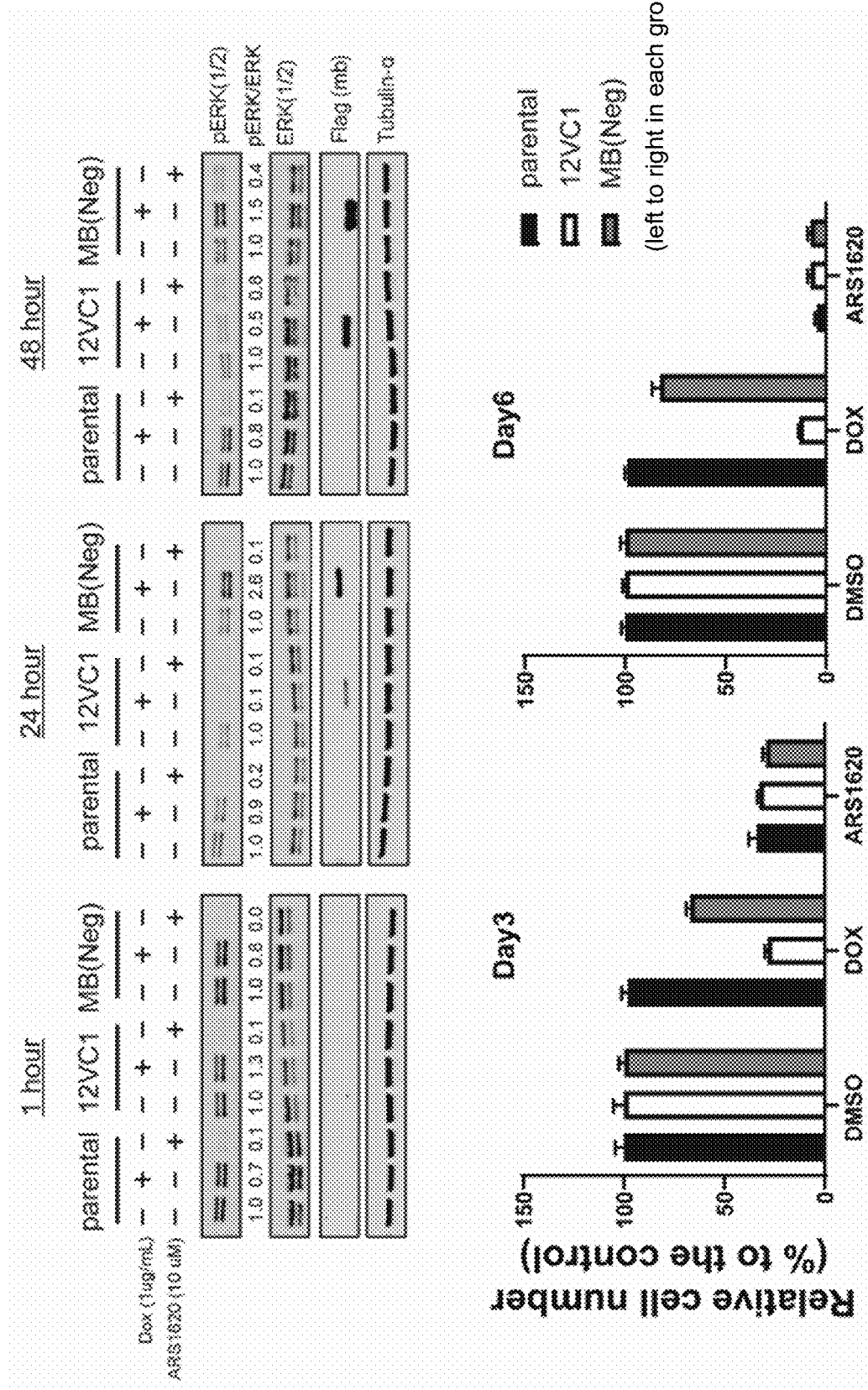
FIG. 13. ERK activation and viability of H358 cells under doxycycline-induced monobody expression or in the presence of the covalent RAS inhibitor ARS1620. 12VC1 expression and ARS1620 treatment each effectively inhibited ERK activation in H358 cells after 24 and 48 hours. Both inhibitors led to similar decreases in viability after 3 and 6 days, respectively. The mean and s.d. (n=8) are shown.

The selectivity and potency of 12VC1 allowed proof-of-concept evaluation on whether a mutant-selective, non-covalent reagent can effectively inhibit the growth of cancer cells driven by endogenous KRAS mutants by using monobodies as genetically encoded, intracellular reagents. Several stable cancer cell lines that express 12VC1 or MB(Neg), a non-binding monobody, were generated under the control of a Dox-inducible promotor (FIG. 11a, b, c), and tested the effects of 12VC1 expression. 12VC1 potently inhibited ERK activation and proliferation of cell lines harboring KRAS (G12C) (H358 and H23) and KRAS(G12V) (PATU8902 and H441), but not those with KRAS(G12D) (HPAF-II) and BRAF(V600E) (A375) or WT RAS (HEK293T) cell lines (FIG. 3a,b, FIG. 12a, b). Sustained expression of 12VC1 was compared with sustained administration of the covalent inhibitor ARS1620 (FIG. 13). Both 12VC1 and ARS1620 achieved similar levels of inhibition of RAS-mediated signaling and viability. These results show that a mutant-selective noncovalent inhibitor can be as effective as a covalent inhibitor, even though non-covalent inhibitors are subjected to reversible binding kinetics and under constant competition with RAS effectors. These results also suggest the importance of high selectivity in achieving efficient inhibition of mutant RAS, which is also underscored by the effectiveness of 12VC1 toward KRAS(G12V) mutant in inhibiting RAS-mediated signaling (FIG. 3a and FIG. 6a)

despite having only moderate affinity to the active state of KRAS(G12V) ($K_D$~100 nM).

Next, the anti-tumor activity of 12VC1 was evaluated using a mouse xenograft model. Two separate derivatives of PATU8902, a cancer cell line of pancreatic origin, that express 12VC1 or MB(Neg) under control of a dox-inducible promoter were prepared and injected them subcutaneously into nude mice. Expression of each monobody was induced after the average tumor size exceeded 100 mm$^3$. 12VC1 expression significantly reduced tumor growth, whereas expression of MB(Neg) had no impact (FIG. 3c, FIG. 12c). Expression of 12VC1 was not detected from these tumors at the end of the xenograft experiment, indicating that the proliferated tumor cells either lost expression due to silencing, or they did not express monobody to begin with, which is a probable scenario, given that a small fraction of cells without monobody expression were present in the polyclonal population of stable cell line (FIG. 11c). By contrast, MB(Neg) was still readily detected from the control tumors, indicating that only 12VC1 expressing cancer cells were eliminated (FIG. 3d). Overall, these results demonstrate that mutant-selective inhibition by a noncovalent inhibitor can effectively suppress the growth of solid tumor in a mouse xenograft model.

Figure 4:
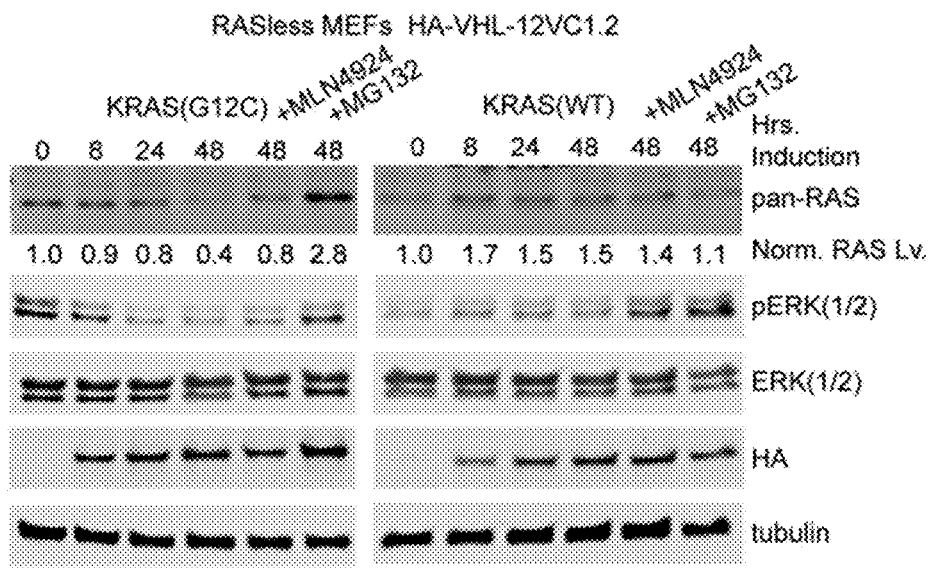
FIG. 4. Selective degradation of RAS mutants with a VHL-monobody fusion protein. a, Degradation of KRAS mutants in RASless MEFs after 0, 8, 24, and 48 hours of dox-induced HA-VHL-12VC1.2 expression. In addition, samples induced for 48 hours were treated with either MLN4924 (1 µM) or MG132 (5 µM) for 24 hours. Total RAS was quantified and normalized relative to t=0. b, Degradation of endogenous RAS by monobody degraders (VHL fusion of 12VC1.1 and 12VC1.2) and its effect on ERK activity in PATU8902 and H23 cell lines containing KRAS(G12V) and KRAS(G12C), respectively. The graphs show the quantification of the total RAS levels in the immunoblots (technical replica, n=2). c, Effects of inhibition (blue) versus degradation (red) of RAS on ERK signaling of H23 cells as a function of intracellular inhibitor and degrader concentration and time (biological replica, n=3, representative results shown). Flag-tagged mVenus-12VC1 fusion (inhibitor) and HA-tagged VHL-12VC1.2 fusion (degrader) were expressed upon addition of doxycycline (1 µg/mL). The expression levels of the inhibitor or degrader were quantified using known amount of protein containing both Flag and HA tags (ctrl) as references. After 72 hours of induction (black arrow), the media were replaced with serum- and doxycycline-free media to examine the persistence effect of intracellular inhibitors or degraders. Graphs show quantification versus time. d, Mouse xenograft experiments with H23 cell line expressing VHL-monobody fusions. Three mice (1 for MB(Neg) and 2 for 12VC1.2) were subcutaneously injected with dox-inducible monobody expressing H23 cell lines at the right and left flanks, and were given dox-containing feed when tumor sizes were roughly 100 mm$^3$ (black arrow). The sizes the tumors expressing MB(Neg) (red, individual) and 12VC1.2 (blue, mean±S.D.) were plotted as a function of time after cell injection. e, Tumors were extracted at the end of experiment and their weights were compared (2 tumors for MB(Neg) and 4 tumors for 12VC1.2, t-test, p-value=0.3). f, Immunoblotting of tumor lysates shows the total amount of monobody, RAS, and pERK at the end of experiment. P denotes the cell line used for xenograft experiment prior to implantation. Tumors were assigned a number (1-4) for identification.
Figure 4:
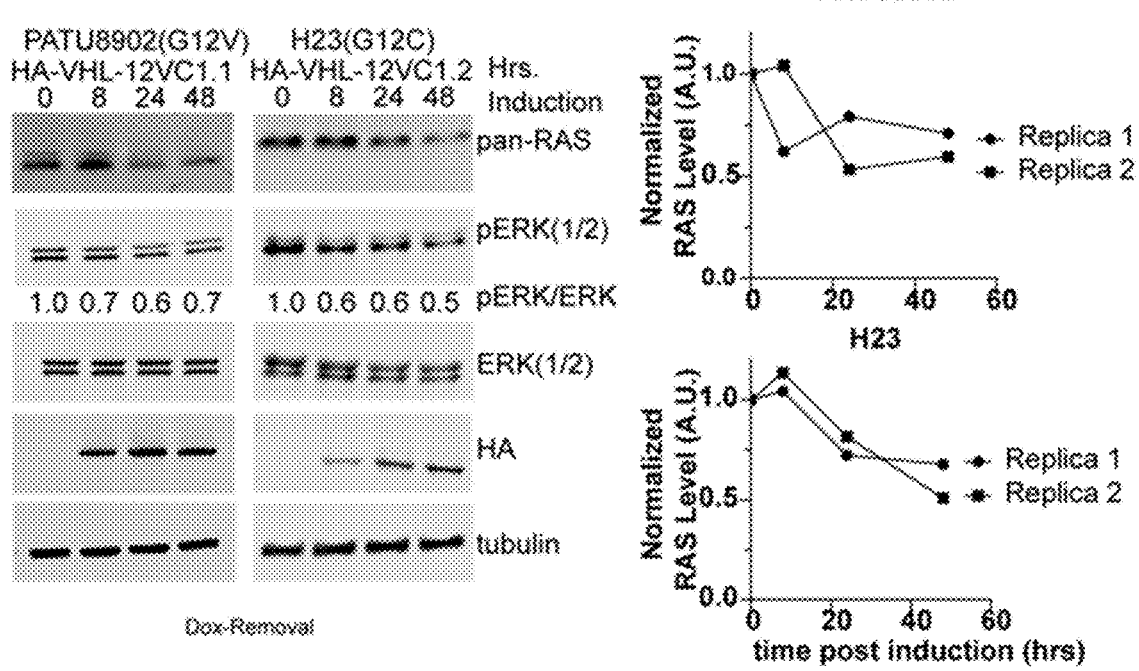
Figure 4:
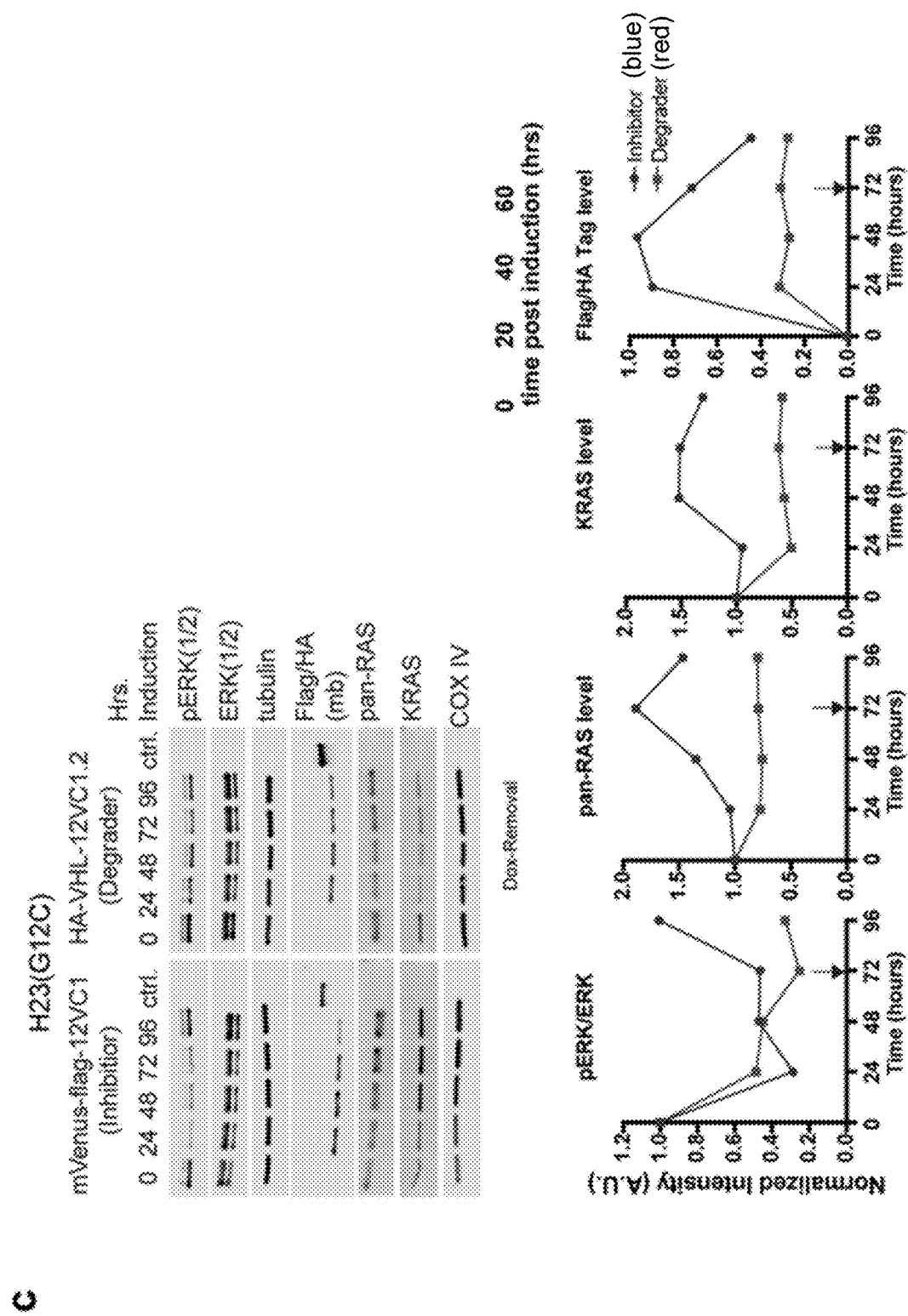
Figure 4:
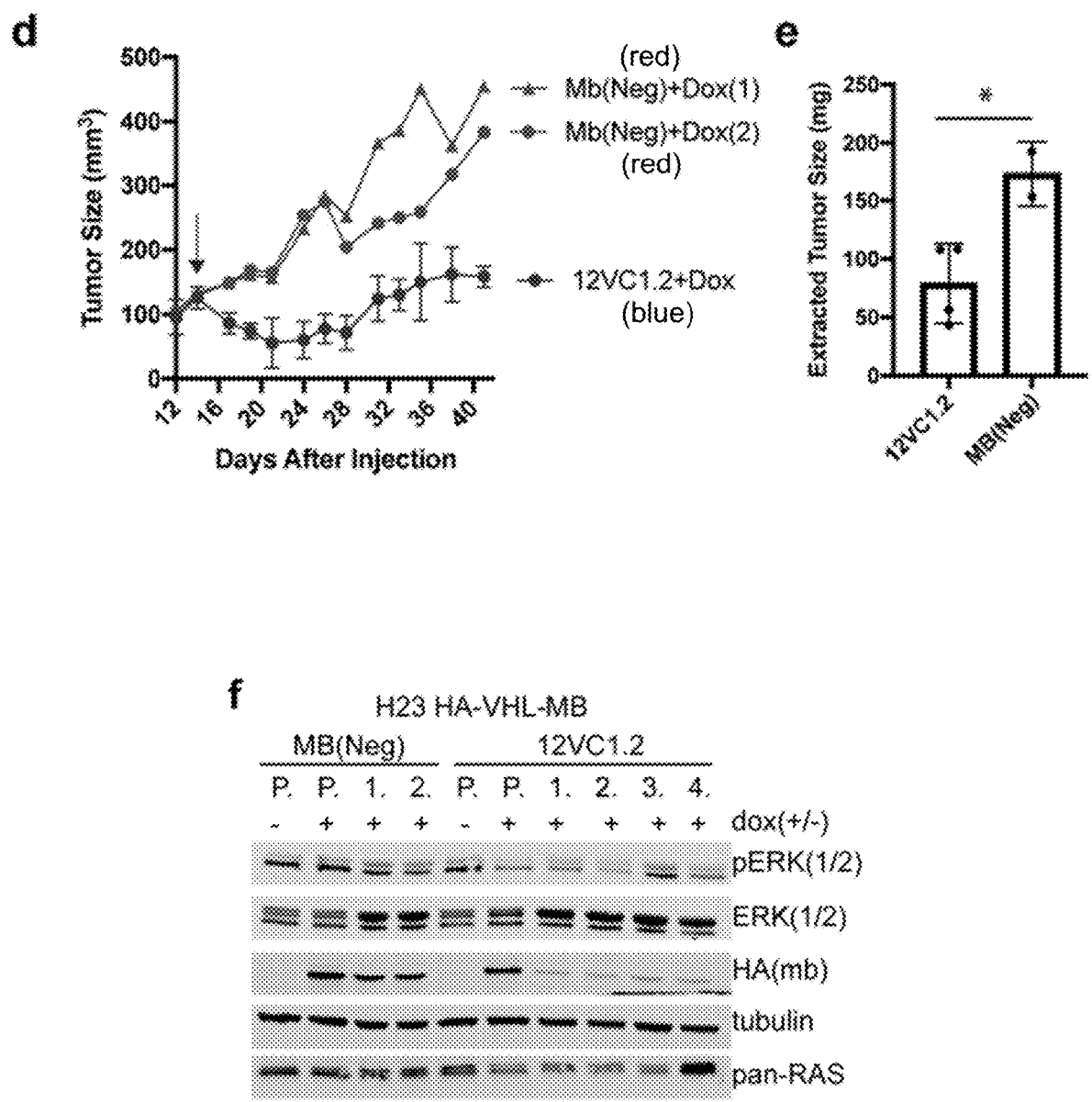
Figure 14:
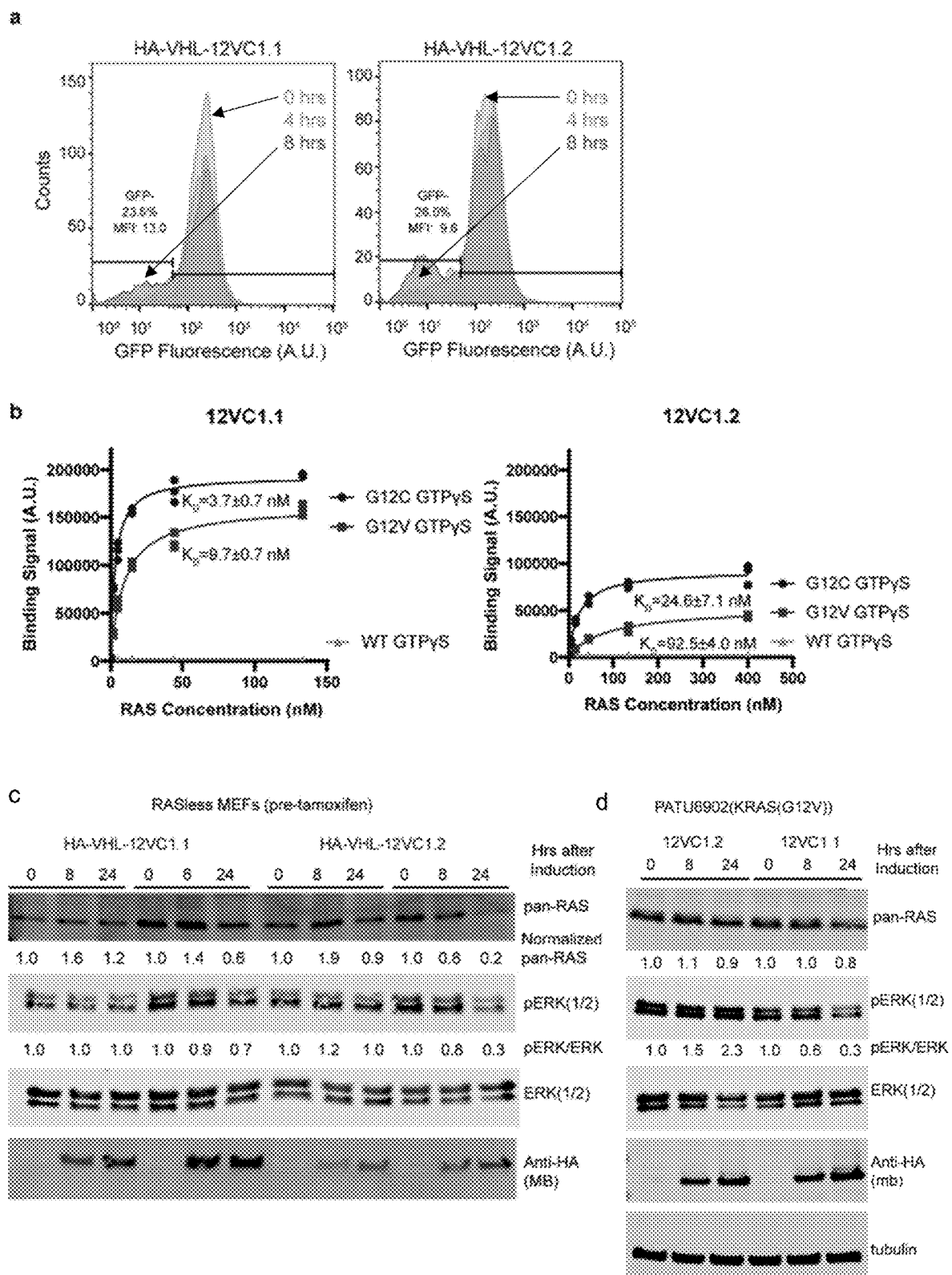
FIG. 14. Mutant-selective RAS degraders using monobody warheads. a, Detection of EGFP-KRAS(G12C) by flow cytometry in Flp293 cells expressing HA-VHL-12VC1.1 or 12VC1.2 under a doxycycline-controlled expression system. Monobody clones, 12VC1.1 and 12VC1.2, were generated by replacing lysine residues of 12VC1 with glutamic acid with the goal of minimizing ubiquitination of the monobody moiety in the fusion protein. The level of KRAS was monitored at 0, 4, and 8 hours after dox induction. 12VC1.2 appeared to degrade EGFP fused KRAS(G12C) more efficiently than 12VC1.1, resulting in lower GFP fluorescence from GFP-population. b, Yeast display binding titration of 12VC1.1 and 1.2 against KRAS (G12C), G12V, and WT bound to GTPγS. $K_D$ values of 12VC1.1 are 3.7±0.7 nM and 9.7±0.7 nM against G12C and G12V, respectively, and those of 12VC1.2 are 24.6±7.1 nM and 92.5±4.0 nM, respectively (mean and s.d. from n=3). c, To evaluate the specificity and efficiency of monobody degraders, RASless MEFs (KRAS$^{flox/flox}$, HRAS$^{-/-}$, NRAS$^{-/-}$, with human KRAS(G12C) or KRAS(WT)) were retrovirally transduced with a dox-inducible expression vector for HA-VHL-12VC1.1 or 12VC1.2. The abundance of KRAS and pERK level were monitored at 0, 8, and 24 hours after induction with dox at 1 µg/mL. Note that 12VC1.1, which has a stronger affinity to KRAS(G12C), is less effective at degrading KRAS compared with 12VC1.2. d, To examine whether monobody degraders can efficiently degrade endogenous KRAS(G12V) and inhibit downstream signaling, PATU8902 cell lines were transduced with the retroviral vectors encoding for HA tagged VHL monobodies. Total RAS and ERK activation were evaluated as a function of time. 12VC1.1, which has a stronger affinity to KRAS(G12V) more effectively degraded KRAS. e, H23 cells expressing mVenus-flag-12VC1 fusion or mVenus-flag-MB(Neg) under a dox-inducible promoter were treated with either doxycycline or ARS1620 to examine the effects of covalent versus non-covalent inhibition on the amount of total RAS (representative data shown, n=2). An increase in the total RAS amount was observed after 48 hours under both covalent and non-covalent inhibition, demonstrating that this increase is not exclusively observed under the inhibition of 12VC1. An increase in pERK levels was be observed from 24 to 48 hours after inhibition, which correlated with the increase in total RAS level. By contrast, expressing MB(Neg) did not impact the level of RAS in cells, as expected. After 48 hours, media containing inhibitors and doxycycline were replaced with serum-free and dox-free media to remove ARS620 and suppress 12VC1 production. However, RAS continued to stay at an elevated level 24 hours after the removal of the inhibitors, revealing the long-term effect of direct inhibition on total RAS level.
Figure 14:
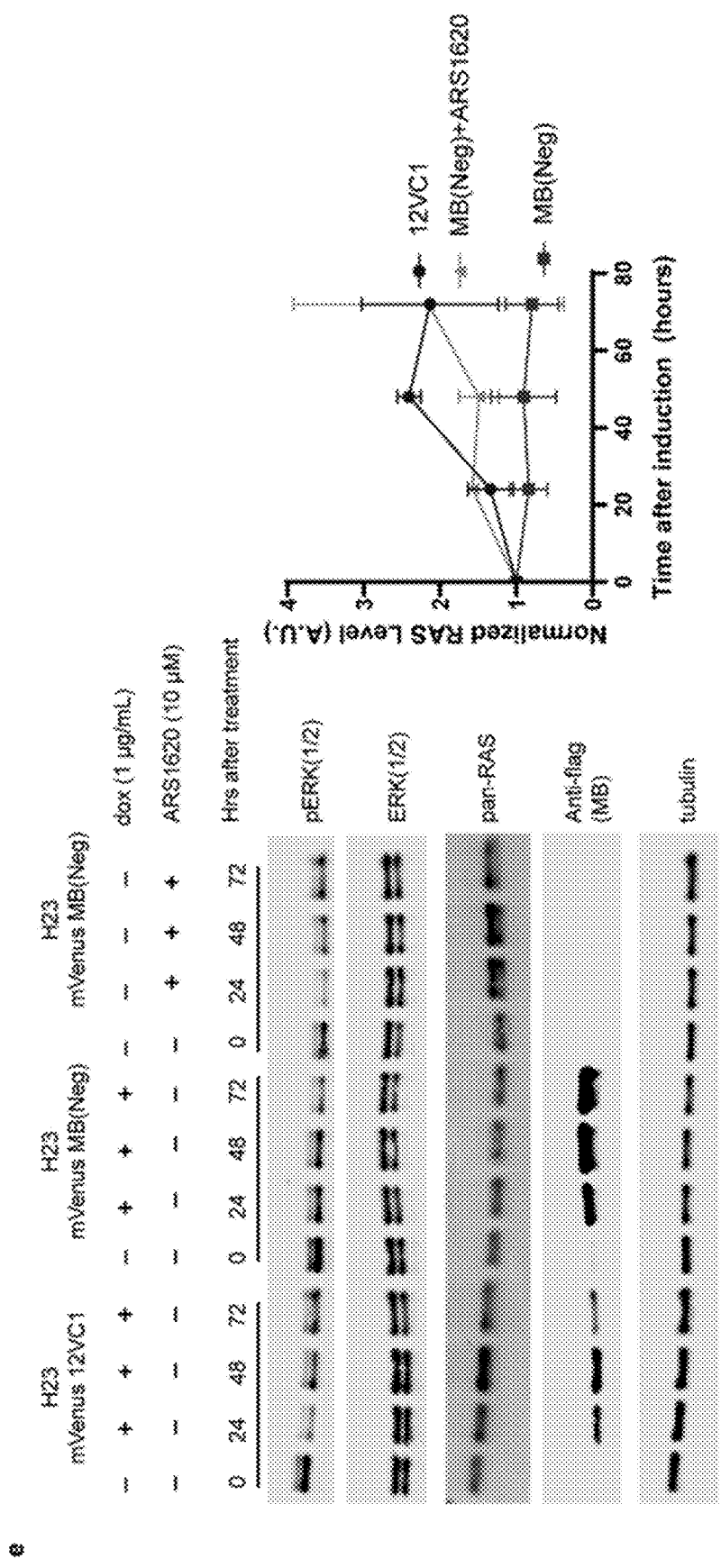

To answer another major question in RAS drug discovery as to whether one can selectively degrade an endogenous RAS mutant, which should offer advantage over inhibition by occupancy, we engineered a proteolysis targeting chimera (PROTAC)-like fusion protein based on 12VC1. Although RAS has been shown to undergo ubiquitination via E3 ligases and degradation, targeted degradation of endogenous KRAS(G12C) was deemed not feasible using PROTAC derivatives of a covalent inhibitor. Furthermore, the covalent inhibitors are not ideal warheads for designing degraders, as their irreversible nature excludes the possibility of multiple cycles of target degradation, an important factor potentiating degraders. Due to a lack of suitable noncovalent ligands, no PROTAC molecules have been developed that are selective to other RAS mutants. We developed variants of 12VC1 termed 12VC1.1 and 12VC1.2 that contained fewer Lys resides and fused them to VHL (FIG. 14a,b). These VHL monobody fusions selectively and efficiently degraded KRAS(G12C) in RASless MEFs (FIG. 4a, FIG. 14c), as well as endogenous RAS in PATU8902 and H23 cancer cell lines (FIG. 4b, FIG. 14d). Treating the cells with MLN4924, a neddylation inhibitor, or MG132, a proteasome inhibitor, rescued the RASless MEFs from RAS degradation, supporting proteasome-dependent degradation. The contribution of direct inhibition by the monobody warheads of these degraders to the reduction of RAS-mediated signaling is negligible, as evident from the correlation between the extent of signal inhibition and the level of total RAS, rather than the abundance of monobody (FIG. 4a, FIG. 14c,d). A decrease of roughly 40% of total RAS was observed, which is consistent with estimations of the fraction of RAS mutant in cells (15-40%) of total RAS, which is comparable to that was observed here. However, the amount of RAS that remained in a cell line after degradation would likely vary depending on factors such as the allele frequency of KRAS mutation of the given cell line. Interestingly, 12VC1.2, which had the weaker affinity to KRAS(G12C) was the more efficient warhead at degradation than 12VC1.1 (FIG. 14c). In contrast, 12VC1.1, which has the stronger affinity of the two to KRAS(G12V), appeared to degrade RAS(G12V) more efficiently in PATU8902 (FIG. 14d). These results suggest the presence of an optimal range of affinity for efficient RAS degradation and the utility of protein-based tools with readily tunable affinity in optimizing PROTAC design.

The development of a selective degrader for a KRAS mutant made it possible to compare effects of selective inhibition and degradation of a KRAS mutant in a signaling assay. Treatment with the covalent inhibitor, ARS1620, or non-covalent 12VC1 inhibitor was initially effective but the pERK level quickly rebounded within 24 hours after the withdrawal of ARS1620 and dox, respectively (FIG. 14e). In contrast, the degrader suppressed the pERK level for a more extended period after the withdrawal of dox (FIG. 4c). The extended efficacy of the degrader is probably due to its ability to suppress the RAS level throughout the experimental period, whereas elevated endogenous RAS levels were observed within 48 hours of treatment with the inhibitors. Similar increases of endogenous RAS after prolonged treatment with covalent inhibitors have been reported, and increased synthesis of RAS has been proposed as a mechanism of adaptation against covalent inhibitors. Thus, these results highlight the potential advantage of selective degradation over direct inhibition.

Finally, the effectiveness of mutant-selective degradation was examined in a mouse xenograft model using the H23 cell line (FIG. 4d). Tumors expressing VHL fused 12VC1.2 were significantly smaller than tumors expressing the VHL-MB(Neg) fusion (FIG. 4d, e), even though the recovered tumor cells contained a greatly reduced amount of VHL-12VC1.2 compared with that in the injected cells and that of the negative control degrader in the recovered tumor cells (FIG. 4f). These results suggest that most of the cells expressing VHL-12VC1.2 fusions did not proliferate. This success of monobody-based PROTAC not only establishes the feasibility of selectively degrading endogenous RAS mutants, but also suggest a new approach to enhance the potency of intracellular biologics and thus reduce the required level of intracellular delivery.

Using monobodies as "tool biologics," the present disclosure describes that oncogenic RAS mutants can be selectively recognized and inhibited using non-covalent approaches. Furthermore, it was demonstrated that a single inhibitor that possesses an appropriate pocket in the binding interface is capable of selectively recognizing multiple oncogenic RAS mutants. This broad spectrum may be therapeutically important in light of reports describing the presence of multiple RAS mutations in a single patient. The structure of the monobody-RAS interface will guide the design of non-covalent inhibitors. Furthermore, these results conclusively establish that endogenous RAS mutants can be selectively degraded, which strongly support the potential of mutant RAS degraders as an effective therapeutic strategy. 12VC1 itself has substantial potential to aid the future drug development effort against RAS mutants, either through protein or gene delivery technologies.

Methods.

Protein expression and purification. All proteins used for monobody development and binding assays, including RAS constructs (KRAS4B residues 1-174 containing G12C, G12V, G12D, G13D, Q61L, WT, NRAS(WT), and HRAS (WT)), Monobodies, and RAF-1 RBD (residues 51-131) were produced with an N-terminal tag containing His6, Avi-tag for biotinylation and a TEV protease recognition site using the pHBT vector. The proteins were produced in *E. coli* BL21(DE3). To produce biotinylated proteins, *E. coli* BL21(DE3) with the pBirA plasmid was used as the host and grown in the presence of 50 µM of biotin. Expressed proteins were purified using Ni-Sepharose columns (GE Healthcare) via gravitational flow, followed by dialysis in Tris buffered saline (TBS, 50 mM Tris-Cl pH7.5 containing 150 mM NaCl) for non-RAS proteins. TBS containing 20 mM $MgCl_2$ and 0.5 mM DTT was used for RAS proteins. Samples were further purified using a Superdex 75 size exclusion column on AKTA Pure systems (GE Healthcare). HRAS(WT) and HRAS(G12C) (residues 1-166) used for crystallization was produced as a fusion protein with His6 and yeast SUMO at the N terminus using an in-house vector described previously. The tag was removed with SUMO hydrolase, followed by overnight dialysis in RAS buffer (50 mM Tris-Cl pH 7.5, 150 mM NaCl, 20 mM $MgCl_2$, 5 mM BME). For monobodies (12VC1 and 12VC3) used in crystallization and RAS used in BLI experiments, proteins were cleaved with TEV-protease in the presence of 0.5 mM EDTA and 1 mM DTT after the Nickel column purification step. Cleaved tags and His-tagged ySUMO hydrolase or TEV-proteases were removed by passing samples through a Ni-Sepharose column, followed by size-exclusion chromatography as described above.

Nucleotide exchange of RAS. Purified RAS proteins used in binding experiment and crystallization were prepared by diluting stock protein (typically containing 20-250 µM RAS) 25 times with 20 mM Tris-Cl buffer pH 7.5 containing 5 mM EDTA, 0.1 mM DTT and 1 mM final concentration of a nucleotide (GDP or GTPγS). Samples were incubated at 30° C. for 30 minutes. $MgCl_2$ was then added to the sample at a final concentration of 20 mM and the solution was further incubated on ice for at least 5 minutes prior to use.

Monobody development. General procedures for the development of monobodies against purified protein targets have been described previously. After four rounds of phage display library selection using biotinylated KRAS(G12C) at concentrations of 100 nM, 100 nM, 50 nM and 50 nM, the genes encoding monobodies from the enriched phage pool were transferred to a yeast display vector, which was used to construct yeast-display libraries. The yeast display libraries were sorted using a Bio-Rad S3e fluorescence-activated cell sorter or a FACSARIA II cell sorter (BD Biosciences). The first round of sorting recovered clones that bound to KRAS (G12C); the second round recovered clones that did not bind to KRAS(WT); and the third round recovered clones that bound to KRAS(G12C). Single clones were then screened for selective binding to RAS mutants. The expression of monobodies on the surface of yeast cells were detected using mouse anti-VS and anti-mouse IgG-FITC conjugate. Target binding was detected with neutravidin Dylight650. Yeast cells were analyzed using an iQue flow cytometer (Sartorius). The median of the signal intensity in the Dylight650 channel for the 75-95$^{th}$ percentile population was taken as representative signal. This sampling method of flow cytometry events minimizes erroneous contributions from events with anomalously high signals while retaining events with high signals. For degradation experiment, monobody degraders were developed by fusing Monobodies 12VC1.1 and 12VC1.2 C-terminal to the VHL domain (1-213) with a SSSSG (SEQ ID NO:24) linker and N-terminal HA tag (YPYDVPDYA (SEQ ID NO:25)) following a published design.

Biolayer interferometry (BLI) analysis. BLI experiments were performed on an Octet Red96 instrument (Molecular Devices). Biotinylated monobodies were immobilized on streptavidin biosensor tips. Samples were diluted in 20 mM HEPES-NaOH buffer (pH 7.4) containing 150 mM NaCl, 5 mM $MgCl_2$, 0.2 mM TCEP and 0.005% Tween-20. BLI signals were analyzed using Octet Data Analysis software (Molecular Devices).

Cell culture. All cell line used in the study were either directly purchased from ATCC (HEK293T, A375, HPAF-II) or validated externally via IDEXX (PATU8902, H23, H358). HEK293T, Flp293, PATU8902, A375, and HPAF-II cells were maintained in DMEM high glucose with L-glutamine (Hyclone) supplemented with 10% FBS (Gemini Bio-products) and antibiotics-antimycotics (Gibco). H358, H23, and H441 cells were maintained in RPMI-1640 high glucose with sodium pyruvate, L-glutamine (Thermo), supplemented with 10% FBS and antibiotic-antimycotic. The absence of *mycoplasma* contamination was periodically confirmed using a PCR-based *mycoplasma* testing kit (Li-LIF).

Transient expression of KRAS and monobody for confocal imaging and signaling experiments. HEK293T cells were cultured in glass-bottom 8-well chambers (ibidi GmbH) for colocalization assays or in a 12-well plate for signaling assays for one day prior to transfection. On the day of transfection at 70-90% confluency, media were replaced with antibiotics-free complete media (DMEM supplemented with 10% FBS). Transfection of pEGFP vectors encoding the appropriate mCherry fused monobodies and EGFP fused KRAS4B constructs was performed with lipofectamine 3000 (Thermo Fisher Scientific) and according to the manufacturer's recommended protocol. On the following day, transfected cells were imaged with a LSM710 confocal microscope (Zeiss) for colocalization experiment or harvested for Western blot analysis.

Pull-down assays. H358, PATU8902, and HEK293T cells were cultured in 10 cm plates (Corning, #430167). H358 and PATU8902 cells were treated with and without ARS1620 (SelleckChem, 58707) at a final concentration of 10 µM for 1.5 hours, and HEK293T cells were treated with EGF (PeproTech; AF-100-15) at a final concentration of 50 ng/mL for 4 minutes. Cells were lysed by incubating them on ice for 15 minutes in GTPase lysis buffer (25 mM Tris-Cl pH 7.2, 150 mM NaCl, 5 mM $MgCl_2$, 1% NP-40 and 5% glycerol supplemented with protease tablet (Roche, 5892991001) and phosphatase inhibitors (1 mM sodium orthovanadate, 10 mM NAF, 54 mM β-glycerol phosphate)) immediately before analysis. After centrifugation for 15 minutes at 15,000 g, the supernatants were collected and incubated with SA agarose resins (Thermo Fisher Scientific) for 1 hour at 4° C. to remove non-specific binders to the resins. After the removal of resins via centrifugation, the pre-cleared lysates were then incubated with biotinylated monobodies bound to SA agarose resins for 3 hours at 4° C. while rotating. The agarose resins were then washed twice with the GTPase lysis buffer and boiled in 1×SDS buffer with 37.5 mM β-mercaptoethanol and processed for Western blotting using a pan-RAS antibody (Santa Cruz Biotechnology, C-4).

Cell signaling assay and quantification of immunoblots. Cells were lysed in RIPA buffer (50 mM Tris-Cl pH 8, 150 mM NaCl, 5 mM EDTA pH8, 0.1% SDS, 1% NP40) supplemented with protease inhibitors (Roche; 5892991001) and phosphatase inhibitors (54 mM β-glycerophosphate, 10 mM NaF, 1 mM sodium vanadate) for 15 minutes on ice, and centrifuged at 15,000 g for 15 minutes. The supernatant was collected and measured for total protein amount using BCA assay (Thermo Scientific; 23227). Lysate (7-20 µg per well) was loaded onto a pre-cast SDS gel (BioRad; 456-1096) followed by electrophoresis. The proteins were then transferred from the gel to a low fluorescence background PVDF membrane (Millipore; IPFL00010) or regular PVDF membrane (Millipore; ISEQ00010) depending on whether fluorescence or chemiluminescence detection was performed.

Phospho-ERK was detected using a rabbit anti-pERK antibody (Cell Signaling; 9101S) and total ERK was detected using a rabbit anti-ERK antibody (Cell Signaling; 9102S). Monobody expression was detected using mouse anti-Flag antibody (Sigma; F3165) or anti-HA tag antibody (BioLegend; 901516). Loading control was detected with primary antibody against tubulin-alpha (Thermo Scientific, 62204) or against cytochrome oxidase (COX IV) (Li-Cor, 926-42214). The total RAS level was detected using a pan-RAS antibody (SCBT, sc-166691). The KRAS level was determined using a KRAS-specific antibody (Sigma, WH0003845M1). For fluorescence detection of immunoblots, the membranes were imaged with a Licor Odyssey Clx imager (Li-Cor Bioscience) using IRDye anti-Rabbit 800CW and anti-Mouse 680LT (Li-Cor Bioscience, 926-32211 and 926-68020, respectively) as secondary antibodies. For chemiluminescence detection, the membrane was imaged with a ChemiDoc imager (BioRad) using anti-Mouse or anti-Rabbit secondary antibody conjugated to HRP (Pierce; 31432 and 31462, respectively). Band intensities of western blot were analyzed with Image Studio Lite version 5.2 (Li-Cor Bioscience). To quantify protein abundance in the degradation experiment, the intensities of pERK, RAS, KRAS, and Flag/HA tag bands were first normalized against the loading control of the perspective blot, which were either tubulin-α, COX IV or total ERK, followed by subsequent normalization to the zero time point. The relative concentrations of intracellular FLAG-tagged monobody inhibitor or HA-tagged monobodies were determined by comparing the intensity of protein bands with the intensity of the bands from equal amounts of loading control proteins (GenScript, M0101) containing both FLAG and HA tag.

Proteomics analysis. Protein samples captured by monobody pull-down, as described above, were digested on beads using trypsin. An aliquot was loaded onto an Acclaim PepMap trap column (2 cm) in line with an EASY-Spray analytical column (50 cm) using the auto sampler with either a data dependent mode on an Easy-nLC 1000 interfaced to a Thermo Fisher Scientific Q Exactive mass spectrometer or a targeted analysis on an Easy-nLC 1200 interfaced to a Thermo Fisher Scientific Q Exactive HF-X mass spectrometer for peptides specific to either the KRAS G12V mutant or KRAS/KRAS 2B. All Acquired MS2 spectra were searched against the Uniprot Homo sapiens reference database containing common contaminant proteins and the mutant KRAS4B G12V using Sequest within Proteome Discoverer 1.4 for the data dependent analysis and using Byonic for the targeted analysis search.

Crystallization and x-ray structure determination. Purified and tag-cleaved H-RAS(G12C) or H-RAS(WT) bound to GTPγS were incubated with purified monobody 12VC1 or 12VC3 at a 1:1.1 molar ratio. The complexes were purified with a Superdex 75 10/300 SEC column (GE Healthcare) in 20 mM Tris-Cl buffer pH 8 containing 100 mM NaCl, 20 mM $MgCl_2$ and 0.2 mM TCEP and concentrated to approximately 10 mg/mL. Both complexes (12CS1:H-RAS(G12C) and 12VC3:H-RAS(WT)) were crystallized in 0.225 M sodium tartrate and 20% PEG3350 when mixed 1:1 in a total volume of 200 nl dispensed by a Mosquito crystallization robot (TTP Labtech) using the hanging drop vapor diffusion method. Crystals were preserved in the mother liquid plus additional 10% (v/v) of PEG3350 for the H-RAS(G12C):12VC1 complex and mother liquid plus 20% glucose for the H-RAS(WT):12VC3 complex. X-ray diffraction data were collected at the Advance Photon Source at the Argonne National Laboratory using beam line 19ID. Diffraction data were processed using HKL3000 and the starting model was built by molecular replacement using PDB entry 4g0n as search models using Phaser. Refinement was performed by phenix refinement, Coot, and PDBredo.

Computational Analysis of Crystal Structures. Fragment-centric topographical mapping (FCTM) as well as molecular dynamics (MD) simulations were performed to investigate the underlying reasons for selective binding of monobody 12VC1 against different RAS mutants. FCTM was performed using AlphaSpace, which utilizes a geometric model based on Voronoi tessellation. Briefly, AlphaSpace identify and represent all concave interaction space across the protein-protein interface as a set of alpha-atom/alpha-space pairs, which are then clustered into discrete fragment-centric pockets. MD simulations were performed with Amber14 molecular dynamics package, employing the Amber14SB force field for the protein. The initial structures for each simulation system were constructed based on our crystal structure of the HRAS-12VC1 complex. The protonation states of charged residues were determined at constant pH 7 based on pKa calculations via the PDB2PQR server. Each system was neutralized with $Na^+$ counterions and solvated with explicit TIP3P water in a rectangular periodic box with 12.0 Å buffer. The Particle-Mesh Ewald (PME) method with 12.0 Å cutoff for the non-bonded interactions was used in the energy minimizations and MD simulations. After a series of minimizations and equilibrations, standard molecular dynamics simulations were performed on GPUs using PMEMD. For each system, MD simulation was carried out for 250-ns with periodic boundary condition and snapshots are saved every 10 ps. The SHAKE algorithm was applied to constrain all bonds involving hydrogen atoms and the Berendsen thermostat method has been used to control the system temperature at 300 K. All other parameters were default values. Saved snapshots were analyzed using cpptraj module in AmberTools 15. Based on the crystal structure of the HRAS(G12C)-12VC1 complex, we have carried out a series of molecular dynamics (MD) simulations to investigate how the monobody 12VC1 interacts with different single mutants of HRAS (G12C, G12V, G12D, G13D and Q61L) as well as its wild type. In addition, in order to investigate the stability of HRAS conformations captured by 12VC1 and 12VC3 monobodies, MD simulations of HRAS structures in absence of monobody binding have also been carried out, the resulted MD snapshots are clustered and representative snapshots were compared with the two HRAS conformations in the monobody complex crystal structures and other 36 GTP analogue-bound HRAS crystal structures obtained from PDB database. All MD simulations were carried out with Amber 16 package using Amber FF14SB force field. Each system was neutralized by adding counterions, and was solvated in explicit TIP3P water box. The GSP molecule was parametrized with general amber force field second version (GAFF2). AmberTools were used to prepare structures and analyze MD trajectories. DBSCAN method is used for MD snapshots clustering. AlphaSpace is employed for analysis of binding pockets on monobody 12VC1.

Stable cell line generation. Genes encoding fluorescent protein, EGFP or mVenus, and genes encoding Monobodies were cloned into pRetro-TetOne vector (CloneTech) with a flag tag spacer using In-Fusion cloning (Takara Bioscience). The mVenus gene was a gift from Steve Vogel (Addgene Plasmid #27793). For degradation studies, genes encoding N-terminally HA-tagged VHL-monobody fusion proteins were cloned into pRetro-TetOne vector using In-Fusion cloning. The VHL gene was a gift from William Kaelin (Addgene Plasmid #19999). Retroviruses were generated by co-transfecting the packaging cell line GP2-293 using Lipofectamine 3000 with the pRetro vector derivatives and the virus envelope vector pVSV-G. After six hours, the transfection mixture was replaced with fresh complete media. Retroviral supernatant was collected 48 hours post transfection and filtered using a 0.45 μm filter. Prior to retroviral transduction, cells of interest were plated in a 6-well cell culture plate (Thermo Scientific; 130184). Polybrene (final concentration of 4 μg/mL) was added to each well containing cells follow by viral transduction using 500 μL of filtered viral supernatant. After the addition of retroviruses, the 6-well plate was centrifuged at 1200 g for 1.5 hours to increase the transduction efficiency. After eight hours, viral supernatants were replaced with new complete media with Tet-Approved FBS (Takara Biosciences; 631367 or Gemini Biosciences, 100-800). Cells were sub-cultured in complete media containing 1 μg/mL puromycin for selection 48 hours post transduction. After puromycin resistance was established, cell lines expressing VHL monobody fusions were aliquoted and used for experiment at the lowest passage number possible. Cells expressing a fluorescent protein-fused monobody were sorted using FACS. Prior to sorting, expression of the monobody was induced by adding 0.1 μg/mL of doxycycline (Clonetech; 631311) for 6 hours. The short induction period and low doxycycline concentration were designed to alleviate potential stress caused by inhibition of RAS function by monobodies. Sorted cells were expanded and monobody expression upon induction was confirmed before they were used for experiments. Cells that express VHL-fused monobody were not sorted due to a lack of selection marker. Cells were maintained in media supplemented with Tet-Approved FBS.

For generating stable cell line that expresses EGFP fused KRAS, Flp293 cell line (Thermo Scientific) was cultured in complete DMEM supplemented with Zeocin (100 μg/mL) for at least 1 passage prior to co-transfection with pOG44 and pFRT vector derivatives (Thermo Scientific) contained cDNA encoding an EGFP fused KRAS construct of interest and hygromycin B resistance gene. 48 hours after transfection, cells were expanded into media containing Hygromycin B (200 μg/mL) for selection. Individual colonies were then screened or pooled and sorted. The resulting cells were verified via flow cytometry for tightly distributed levels of EGFP expression.

Cell proliferation assay. Dox-inducible stable cell lines expressing 12VC1 or MB(Neg) were mixed with the parental cell line at an approximately 1:1 ratio and seeded in a 12 well or 24 well plate. Cells were then cultured in the presence of 1 μg/mL doxycycline for the entire duration of experiment (7-8 days) and subcultured into a new 12 well or 24 well plate every 2 days. For a control experiment to eliminate the possibility that the growth bias is caused by retroviral transduction but not by monobody expression, cells transduced with the 12VC1 vector were grown in the absence of Dox and then induced 24 hours prior to the last measurement. The mixed culture was sampled periodically and the ratio between monobody expressing cells (mVenus and GFP positive) and non-expressing cells was determined using flow cytometry analysis (FIG. 11).

Cell viability assay. A total of 3000 cells were seeded in the well of a 96-well flat-bottom plate with clear window. Cells were either treated with 15 μM of ARS1620 or 1 μg/mL doxycycline. Fresh reagents were added every three days. To measure cell viability the presto blue reagent (Thermo Fisher) was added at 10% of the culture volume. After two hours of incubation at 37° C., the fluorescence intensity of the wells was measured (ex:560 nm/em:590 nm) with a FlexStation 3 multi-mode plate reader (Molecular Devices).

Mouse xenograft experiments. Animal experiments were approved by NYU Langone Institutional Animal Care and Use Committee (IACUC, protocol 170602). PATU8902 or H23 cells expressing monobody under a dox-inducible promotor ($5 \times 10^6$) were subcutaneously injected into athymic nude mice (Charles River). Once the average tumor size exceeded 100 mm$^3$, the mice were given food containing doxycycline (Envigo; TD.01306). Tumor sizes were measured using a digital caliper thrice a week along with body weight to ensure that mice were healthy through the duration of doxycycline treatment.

Data Availability: Atomic coordinates for HRAS(G12C)-12VC1 and HRAS(WT)-12VC3 structures will be available in the Protein Data Bank. The data sets generated during and/or analyzed during the current study are available on reasonable request.

Although the present disclosure has been described with respect to one or more particular embodiments and/or examples, it will be understood that other embodiments and/or examples of the present disclosure may be made without departing from the scope of the present disclosure.

The invention claimed is:

1. A protein or peptide comprising:
   i) the following sequence:
   VSSVPTKLEVVAATPTSLLISWDAPAVTVFFYVITY-GETGHGVGAFQAFKVPGSKSTATIS GLKPGVDYTITVYARGYSKQGPYKPSPISINYRT (12VC1) (SEQ ID NO:1) or a truncated variant thereof;
   or
   ii) a variant of SEQ ID NO:1 with at least 90% homology to SEQ ID NO:1 or a truncated variant thereof,
   wherein the truncated variant of i) or ii) has up to the first four residues at the N-terminus removed.

2. The protein or peptide according to claim 1, wherein one or more of the proteins or peptides are disposed on a bead or resin or membrane.

3. The protein or peptide according to claim 1, wherein one or more of the proteins or peptides are conjugated to a yeast display.

4. The protein or peptide according to claim 1, wherein the protein or peptide is non-covalently bound and/or covalently conjugated to one or more other proteins and peptides such that a dimer, trimer, or oligomer is formed.

5. The protein or peptide according to claim 1, wherein the protein or peptide is fused to a larger protein or peptide.

6. The protein or peptide according to claim 5, wherein the larger protein or peptide is GFP, a GFP variant, yeast Aga2, or an epitope tag.

7. The protein or peptide according to claim 1, wherein the variant is:

(SEQ ID NO: 2)
VSSVPTELEVVAATPTSLLISWDAPAVTVFFYVITYGETGHGVGAFQAFK
VPGSRSTATISGLEPGVDYTITVYARGYSKQGPYKPSPISINYRT;

(SEQ ID NO: 3)
VSSVPTELEVVAATPTSLLISWDAPAVTVFFYVITYGETGHGVGAFQAFA
VPGSRSTATISGLEPGVDYTITVYARGYSKQGPYKPSPISINYRT;

(SEQ ID NO: 4)
VSSVPTKLEVVAATPTSLLISWDAPAVTVFFYIIAYGETGHGVGAFQAFR
VPGSKSTATISGLKPGVDYTITVYARGYSKQGPYKPSPISINYRT;

(SEQ ID NO: 5)
VSSVPTKLEVVAATPTSLLISWDAPAVTVAFYVITYGETGHGVGAFQAFK
VPGSKSTATISGLKPGVDYTITVYARGYSKQGPYKPSPISINYRT;

(SEQ ID NO: 6)
VSSVPTKLEVVAATPTSLLISWDAPAVTVFAYVITYGETGHGVGAFQAFK
VPGSKSTATISGLKPGVDYTITVYARGYSKQGPYKPSPISINYRT;

(SEQ ID NO: 7)
VSSVPTKLEVVAATPTSLLISWDAPAVTVFFYAITYGETGHGVGAFQAFK
VPGSKSTATISGLKPGVDYTITVYARGYSKQGPYKPSPISINYRT;

(SEQ ID NO: 8)
VSSVPTKLEVVAATPTSLLISWDAPAVTVFFYVIAYGETGHGVGAFQAFK
VPGSKSTATISGLKPGVDYTITVYARGYSKQGPYKPSPISINYRT;

(SEQ ID NO: 9)
VSSVPTKLEVVAATPTSLLISWDAPAVTVFFYVITYGETGHGAGAFQAFK
VPGSKSTATISGLKPGVDYTITVYARGYSKQGPYKPSPISINYRT;

(SEQ ID NO: 10)
VSSVPTKLEVVAATPTSLLISWDAPAVTVFFYVITYGETGHGVGAAQAFK
VPGSKSTATISGLKPGVDYTITVYARGYSKQGPYKPSPISINYRT;

(SEQ ID NO: 11)
VSSVPTKLEVVAATPTSLLISWDAPAVTVFFYVITYGETGHGVGAFAAFK
VPGSKSTATISGLKPGVDYTITVYARGYSKQGPYKPSPISINYRT;

(SEQ ID NO: 12)
VSSVPTKLEVVAATPTSLLISWDAPAVTVFFYVITYGETGHGVGAFQAAK
VPGSKSTATISGLKPGVDYTITVYARGYSKQGPYKPSPISINYRT;

-continued (SEQ ID NO: 13)
VSSVPTKLEVVAATPTSLLISWDAPAVTVFFYVITYGETGHGVGAFQAFA

VPGSKSTATISGLKPGVDYTITVYARGYSKQGPYKPSPISINYRT;

(SEQ ID NO: 14)
VSSVPTKLEVVAATPTSLLISWDAPAVTVFFYVITYGETGHGVGAFQAFK

VAGSKSTATISGLKPGVDYTITVYARGYSKQGPYKPSPISINYRT;

(SEQ ID NO: 15)
VSSVPTKLEVVAATPTSLLISWDAPAVTVFFYVITYGETGHGVGAFQAFK

VPASKSTATISGLKPGVDYTITVYARGYSKQGPYKPSPISINYRT;

(SEQ ID NO: 16)
VSSVPTKLEVVAATPTSLLISWDAPAVTVFFYVITYGETGHGVGAFQAFK

VPGSKSTATISGLKPGVDYTITVYARAYSKQGPYKPSPISINYRT;

(SEQ ID NO: 17)
VSSVPTKLEVVAATPTSLLISWDAPAVTVFFYVITYGETGHGVGAFQAFK

VPGSKSTATISGLKPGVDYTITVYARGASKQGPYKPSPISINYRT;

(SEQ ID NO: 18)
VSSVPTKLEVVAATPTSLLISWDAPAVTVFFYVITYGETGHGVGAFQAFK

VPGSKSTATISGLKPGVDYTITVYARGYSKQGAYKPSPISINYR;

(SEQ ID NO: 19)
VSSVPTKLEVVAATPTSLLISWDAPAVTVFFYVITYGETGHGVGAFQAFK

VPGSKSTATISGLKPGVDYTITVYARGYSKQGPAKPSPISINYRT;

(SEQ ID NO: 20)
VSSVPTKLEVVAATPTSLLISWDAPAVTVFFYVITYGETGHGVGAFQAFK

VPGSKSTATISGLKPGVDYTITVYARGYSKQGPYAPSPISINYRT;

or a truncated variant thereof, wherein the truncated variant has up to the first four residues at the N-terminus removed.

8. The protein or peptide according to claim 1, wherein the protein or peptide is modified at a sidechain of one or more amino acid residue(s), the C-terminus, the N-terminus, or a combination thereof.

9. The protein or peptide of claim 1, wherein the variant of SEQ ID NO:1 comprises a sequence where at least the following underlined amino acid residues of SEQ ID NO:1 are not replaced with a different amino acid residue:

(SEQ ID NO: 1)
VSSVPTKLEVVAATPTSLLISWDAPAVTVF<u>F</u>Y<u>V</u>ITYGETGHG<u>V</u>GA<u>F</u>QA<u>F</u>

KVPGSKSTATISGLKPGVDYTITV<u>YAR</u>GYSKQGP<u>Y</u>KPSPISINYRT (12VC1).

10. The protein or peptide of claim 1, wherein the variant of SEQ ID NO:1 comprises a sequence where at least the following underlined amino acid residues of SEQ ID NO:1 are not replaced with a different amino acid residue:

(SEQ ID NO: 1)
VSSVPTKLE<u>V</u>VAATPTSLL<u>I</u>S<u>W</u>DAPAVTVF<u>F</u>Y<u>V</u>ITYGETGHG<u>V</u>GA<u>F</u>QA<u>F</u>

K<u>V</u>P<u>G</u>S<u>T</u>A<u>TI</u>S<u>GL</u>KPGVD<u>Y</u>TITV<u>YAR</u>GYSKQGP<u>Y</u>K<u>P</u>SPISINYRT (12VC1).

11. The protein or peptide of claim 1, wherein the variant of SEQ ID NO: 1 conserves at least the following sequence from SEQ ID NO:1: VYARG.

12. The protein or peptide of claim 1, wherein the variant of SEQ ID NO: 1 has 91% homology to SEQ ID NO:1.

13. The protein or peptide of claim 1, wherein the variant of SEQ ID NO: 1 has 93% homology to SEQ ID NO:1.

14. The protein or peptide of claim 1, wherein the variant of SEQ ID NO:1 has 95% homology to SEQ ID NO:1.

15. A composition comprising a protein or peptide according to claim 1 and a pharmaceutically acceptable carrier.

16. A fusion protein or proteolysis targeting chimera (PROTAC) comprising the protein or peptide according to claim 1.

17. The fusion protein or PROTAC according to claim 16, further comprising an E3 ligase subunit or fragment of an E3 subunit.

18. The fusion protein or PROTAC according to claim 17, wherein the E3 ligase is Von Hippel-Lindau tumor suppressor (VHL), cereblon (CRBN), mouse double minute 2 (MDM2), cellular inhibitor of apoptosis (cIAP), and speckle-type POZ protein (SPOP).

19. A composition comprising a fusion protein or PROTAC according to claim 16 and a pharmaceutically acceptable carrier.

20. A protein or peptide comprising the following sequence or a truncated variant thereof, or having the following sequence or truncated variant thereof:

(SEQ ID NO: 26)
XXXVPTXLEVVAATXXSLLISWDAPAVTVXFYVIXYGETGHGVGAFXAF

XVXXXXSTATISGLXPGVDYTITVYARXXSKQGXYXPSPISINYRT, wherein each X is a canonical or non-canonical amino acid and the truncated variant of SEQ ID NO:26 has up to the first four residues at the N-terminus removed.

21. The protein or peptide according to claim 20, wherein the sequence is:

(SEQ ID NO: 27)
VSSVPTKLEVVAATPTSLLISWDAPAVTVXFYVIXYGETGHGVGAFXAFX

VXXSKSTATISGLKPGVDYTITVYARXXSKQGXYXPSPISINYRT or a truncated variant thereof, or (SEQ ID NO: 28)
XXXVPTXLEVVAATXXSLLISWDAPAVTVFFYVITYGETGHGVGAFQAFK

VPGXXSTATISGLXPGVDYTITVYARGYSKQGPYKPSPISINYRT or a truncated variant thereof, wherein the truncated variant of SEQ ID NO:27 or the truncated variant of SEQ ID NO:28 has up to the first four residues at the N-terminus removed.

22. The protein or peptide according to claim 20, wherein each X is individually chosen from alanine, serine, arginine, glutamine, asparagine, threonine, and tyrosine.

23. A protein or peptide comprising the following sequence:
VSSVPTKLEVVAATPTSLLISWDAPAVTVFFYVITY-GETGHGVGAFQAFKVPGSKSTATIS GLKPGVDYTITVYARGYSKQGPYKPSPISINYRT (12VC1) (SEQ ID NO:1) or a truncated variant thereof, wherein the truncated variant has up to the first four residues at the N-terminus removed.

* * * * *